(12) United States Patent
Poole et al.

(10) Patent No.: US 11,850,075 B2
(45) Date of Patent: *Dec. 26, 2023

(54) RADIO FREQUENCY COIL METHODS AND APPARATUS

(71) Applicant: Hyperfine Operations, Inc., Guilford, CT (US)

(72) Inventors: Michael Stephen Poole, Guilford, CT (US); Gregory L. Charvat, Guilford, CT (US); Todd Rearick, Cheshire, CT (US); Jonathan M. Rothberg, Guilford, CT (US)

(73) Assignee: Hyperfine Operations, Inc., Guilford, CT (US)

( * ) Notice: Subject to any disclaimer, the term of this patent is extended or adjusted under 35 U.S.C. 154(b) by 61 days.

This patent is subject to a terminal disclaimer.

(21) Appl. No.: 16/926,272

(22) Filed: Jul. 10, 2020

(65) Prior Publication Data
US 2020/0337644 A1    Oct. 29, 2020

Related U.S. Application Data

(63) Continuation of application No. 15/152,951, filed on May 12, 2016, now Pat. No. 10,709,387.
(Continued)

(51) Int. Cl.
*A61B 5/00* (2006.01)
*A61B 5/055* (2006.01)
(Continued)

(52) U.S. Cl.
CPC .......... *A61B 5/7203* (2013.01); *A61B 5/0042* (2013.01); *A61B 5/055* (2013.01);
(Continued)

(58) Field of Classification Search
CPC ........ G01R 33/34007; G01R 33/34046; G01R 33/3678; G01R 33/381; G01R 33/385;
(Continued)

(56) References Cited

U.S. PATENT DOCUMENTS 3,771,055 A   11/1973   Anderson
4,665,368 A    5/1987   Sugiyama et al.
(Continued)

FOREIGN PATENT DOCUMENTS

CN       1694730 A    11/2005
CN     101322646 A    12/2008
(Continued)

OTHER PUBLICATIONS

U.S. Appl. No. 15/152,951, filed May 12, 2016, Poole et al.
(Continued)

*Primary Examiner* — Dixomara Vargas
(74) *Attorney, Agent, or Firm* — Foley & Lardner LLP

(57) ABSTRACT

Aspects relate to providing radio frequency components responsive to magnetic resonance signals. According to some aspects, a radio frequency component comprises at least one coil having a conductor arranged in a plurality of turns oriented about a region of interest to respond to corresponding magnetic resonant signal components. According to some aspects, the radio frequency component comprises a plurality of coils oriented to respond to corresponding magnetic resonant signal components. According to some aspects, an optimization is used to determine a configuration for at least one radio frequency coil.

15 Claims, 30 Drawing Sheets

Related U.S. Application Data

(60) Provisional application No. 62/169,102, filed on Jun. 1, 2015, provisional application No. 62/160,036, filed on May 12, 2015.

(51) Int. Cl.
| | |
|---|---|
| *G01R 33/34* | (2006.01) |
| *G01R 33/36* | (2006.01) |
| *G01R 33/381* | (2006.01) |
| *G01R 33/385* | (2006.01) |

(52) U.S. Cl.
CPC .. *G01R 33/34007* (2013.01); *G01R 33/34046* (2013.01); *G01R 33/3678* (2013.01); *A61B 5/725* (2013.01); *G01R 33/381* (2013.01); *G01R 33/385* (2013.01)

(58) Field of Classification Search
CPC ..... A61B 5/7203; A61B 5/0042; A61B 5/055; A61B 5/725
See application file for complete search history.

(56) References Cited

U.S. PATENT DOCUMENTS

| | | | |
|---|---|---|---|
| 4,712,068 A * | 12/1987 | Savelainen | G01R 33/34046 324/318 |
| 4,766,383 A | 8/1988 | Fox et al. | |
| 4,774,468 A | 9/1988 | Bydder | |
| 5,038,104 A * | 8/1991 | Wikswo, Jr. | G01R 33/0358 324/258 |
| 5,050,605 A | 9/1991 | Eydelman et al. | |
| 5,256,960 A | 10/1993 | Novini | |
| 5,315,251 A | 5/1994 | Derby | |
| 5,323,111 A * | 6/1994 | Suzuki | G01R 33/4835 324/309 |
| 5,479,925 A | 1/1996 | Dumoulin et al. | |
| 5,500,594 A | 3/1996 | Leussler | |
| 5,539,315 A | 7/1996 | Cory et al. | |
| 5,603,320 A | 2/1997 | Dumoulin et al. | |
| 5,713,359 A | 2/1998 | Dumoulin et al. | |
| 5,804,968 A * | 9/1998 | Richard | G01R 33/385 324/318 |
| 6,023,166 A | 2/2000 | Eydelman | |
| 6,169,401 B1 * | 1/2001 | Fujita | G01R 33/3678 324/318 |
| 6,316,941 B1 * | 11/2001 | Fujita | G01R 33/34046 324/318 |
| 6,566,873 B1 | 5/2003 | Smith et al. | |
| 6,624,633 B1 | 9/2003 | Zou et al. | |
| 6,650,926 B1 | 11/2003 | Chan et al. | |
| 6,750,653 B1 | 6/2004 | Zou et al. | |
| 6,784,665 B1 | 8/2004 | Chan et al. | |
| 6,958,608 B2 | 10/2005 | Takagi et al. | |
| 7,047,059 B2 | 5/2006 | Avrin et al. | |
| 7,109,705 B2 | 9/2006 | Smith et al. | |
| 7,355,407 B1 * | 4/2008 | Zhang | G01R 33/5616 324/309 |
| 7,391,213 B2 | 6/2008 | Watkins et al. | |
| 7,884,609 B2 | 2/2011 | Soutome et al. | |
| 8,193,810 B2 | 6/2012 | Otake et al. | |
| 8,487,729 B2 * | 7/2013 | Bulatowicz | H01F 7/202 335/299 |
| 8,653,820 B2 | 2/2014 | Dohata et al. | |
| 8,710,843 B2 * | 4/2014 | Carlone | G01R 33/4812 324/318 |
| 8,884,617 B2 * | 11/2014 | Goodwill | G01R 33/1276 324/301 |
| 9,154,003 B2 | 10/2015 | Ichikawa | |
| 9,274,084 B2 * | 3/2016 | Goodwill | G01R 33/10 |
| 9,541,616 B2 | 1/2017 | Rothberg et al. | |
| 9,547,057 B2 | 1/2017 | Rearick et al. | |
| 9,585,594 B2 | 3/2017 | Martens et al. | |
| 9,625,543 B2 | 4/2017 | Rearick et al. | |
| 9,625,544 B2 | 4/2017 | Poole et al. | |
| 9,638,773 B2 | 5/2017 | Poole et al. | |
| 9,645,210 B2 | 5/2017 | McNulty et al. | |
| 9,733,325 B2 * | 8/2017 | Grenier | G01R 33/4831 |
| 9,763,594 B2 * | 9/2017 | Goodwill | A61B 5/0515 |
| 9,797,971 B2 | 10/2017 | Rearick et al. | |
| 9,817,093 B2 | 11/2017 | Rothberg et al. | |
| 10,050,474 B2 | 8/2018 | Ichikawa | |
| 10,139,464 B2 | 11/2018 | Rearick et al. | |
| 10,145,913 B2 | 12/2018 | Hugon et al. | |
| 10,145,922 B2 | 12/2018 | Rothberg et al. | |
| 10,222,434 B2 | 3/2019 | Poole et al. | |
| 10,222,435 B2 | 3/2019 | Mileski et al. | |
| 10,222,505 B2 | 3/2019 | Reiderman et al. | |
| 10,241,177 B2 | 3/2019 | Poole et al. | |
| 10,274,561 B2 | 4/2019 | Poole et al. | |
| 10,281,540 B2 | 5/2019 | Mileski et al. | |
| 10,281,541 B2 | 5/2019 | Poole et al. | |
| 10,295,628 B2 | 5/2019 | Mileski et al. | |
| 10,310,037 B2 | 6/2019 | McNulty et al. | |
| 10,324,147 B2 | 6/2019 | McNulty et al. | |
| 10,330,755 B2 | 6/2019 | Poole et al. | |
| 10,353,030 B2 | 7/2019 | Poole et al. | |
| 10,371,773 B2 | 8/2019 | Poole et al. | |
| 10,379,186 B2 | 8/2019 | Rothberg et al. | |
| 10,416,264 B2 | 9/2019 | Sofka et al. | |
| 10,444,310 B2 | 10/2019 | Poole et al. | |
| 10,466,327 B2 | 11/2019 | Rothberg et al. | |
| 10,488,482 B2 | 11/2019 | Rearick et al. | |
| 10,495,712 B2 | 12/2019 | Rothberg et al. | |
| 10,520,566 B2 | 12/2019 | Poole et al. | |
| 10,527,689 B2 | 1/2020 | Rosen et al. | |
| 10,527,692 B2 | 1/2020 | McNulty et al. | |
| 10,534,058 B2 | 1/2020 | Sofka et al. | |
| 10,539,637 B2 | 1/2020 | Poole et al. | |
| 10,545,207 B2 | 1/2020 | Poole et al. | |
| 10,551,452 B2 | 2/2020 | Rearick et al. | |
| 10,564,239 B2 | 2/2020 | Poole et al. | |
| 10,591,561 B2 | 3/2020 | Sacolick et al. | |
| 10,709,387 B2 | 7/2020 | Poole et al. | |
| 10,912,517 B2 * | 2/2021 | Poole | G01R 33/34007 |
| D912,822 S | 3/2021 | Hugon | |
| 2002/0057087 A1 | 5/2002 | Crozier et al. | |
| 2003/0095021 A1 * | 5/2003 | Schauwecker | H01F 6/00 335/216 |
| 2004/0251902 A1 | 12/2004 | Takagi et al. | |
| 2005/0073306 A1 | 4/2005 | Smith et al. | |
| 2005/0122106 A1 * | 6/2005 | Ham | G01R 33/385 324/318 |
| 2005/0253582 A1 | 11/2005 | Giaquinto et al. | |
| 2006/0052692 A1 | 3/2006 | Weiss | |
| 2006/0127313 A1 | 6/2006 | Goldman et al. | |
| 2006/0244449 A1 | 11/2006 | Muftuler et al. | |
| 2006/0273786 A1 | 12/2006 | Smith et al. | |
| 2007/0257670 A1 | 11/2007 | Giaquinto et al. | |
| 2007/0285096 A1 | 12/2007 | Soutome et al. | |
| 2009/0021256 A1 | 1/2009 | Soutome et al. | |
| 2009/0128155 A1 | 5/2009 | Otake et al. | |
| 2010/0033173 A1 | 2/2010 | Gleich et al. | |
| 2011/0221438 A1 * | 9/2011 | Goodwill | G01N 27/72 324/301 |
| 2011/0247414 A1 * | 10/2011 | Bulatowicz | G01R 33/381 73/504.02 |
| 2011/0260729 A1 * | 10/2011 | Carlone | A61N 5/1049 324/318 |
| 2013/0328562 A1 * | 12/2013 | Grenier | G01R 33/4831 324/309 |
| 2014/0145717 A1 | 5/2014 | Ozawa et al. | |
| 2014/0155732 A1 | 6/2014 | Patz et al. | |
| 2014/0159728 A1 | 6/2014 | Wirtz et al. | |
| 2015/0000112 A1 | 1/2015 | Martens et al. | |
| 2016/0022142 A1 | 1/2016 | Bradshaw | |
| 2016/0069968 A1 | 3/2016 | Rothberg et al. | |
| 2016/0069970 A1 | 3/2016 | Rearick et al. | |
| 2016/0069971 A1 | 3/2016 | McNulty et al. | |
| 2016/0069972 A1 | 3/2016 | Poole et al. | |
| 2016/0069975 A1 | 3/2016 | Rothberg et al. | |
| 2016/0128592 A1 | 5/2016 | Rosen et al. | |
| 2016/0131727 A1 | 5/2016 | Sacolick et al. | |

(56) References Cited

U.S. PATENT DOCUMENTS

| | | |
|---|---|---|
| 2016/0154075 A1 | 6/2016 | Song et al. |
| 2016/0169992 A1 | 6/2016 | Rothberg et al. |
| 2016/0169993 A1 | 6/2016 | Rearick et al. |
| 2016/0223631 A1 | 8/2016 | Poole et al. |
| 2016/0231399 A1 | 8/2016 | Rothberg et al. |
| 2016/0231402 A1 | 8/2016 | Rothberg et al. |
| 2016/0231403 A1 | 8/2016 | Rothberg et al. |
| 2016/0231404 A1 | 8/2016 | Rothberg et al. |
| 2016/0299203 A1 | 10/2016 | Mileski et al. |
| 2016/0334479 A1* | 11/2016 | Poole .................. A61B 5/7203 |
| 2017/0010339 A1 | 1/2017 | Rosen et al. |
| 2017/0102443 A1 | 4/2017 | Rearick et al. |
| 2017/0227616 A1 | 8/2017 | Poole et al. |
| 2017/0276747 A1 | 9/2017 | Hugon et al. |
| 2017/0276749 A1 | 9/2017 | Hugon et al. |
| 2018/0024208 A1 | 1/2018 | Rothberg et al. |
| 2018/0038931 A1 | 2/2018 | Rearick et al. |
| 2018/0088193 A1 | 3/2018 | Rearick et al. |
| 2018/0143274 A1 | 5/2018 | Poole et al. |
| 2018/0143275 A1 | 5/2018 | Sofka et al. |
| 2018/0143280 A1 | 5/2018 | Dyvorne et al. |
| 2018/0143281 A1 | 5/2018 | Sofka et al. |
| 2018/0144467 A1 | 5/2018 | Sofka et al. |
| 2018/0156881 A1 | 6/2018 | Poole et al. |
| 2018/0164390 A1 | 6/2018 | Poole et al. |
| 2018/0168527 A1 | 6/2018 | Poole et al. |
| 2018/0210047 A1 | 7/2018 | Poole et al. |
| 2018/0224512 A1 | 8/2018 | Poole et al. |
| 2018/0238978 A1 | 8/2018 | McNulty et al. |
| 2018/0238980 A1 | 8/2018 | Poole et al. |
| 2018/0238981 A1 | 8/2018 | Poole et al. |
| 2019/0004130 A1 | 1/2019 | Poole et al. |
| 2019/0011510 A1 | 1/2019 | Hugon et al. |
| 2019/0011513 A1 | 1/2019 | Poole et al. |
| 2019/0011514 A1 | 1/2019 | Poole et al. |
| 2019/0011521 A1 | 1/2019 | Sofka et al. |
| 2019/0018094 A1 | 1/2019 | Mileski et al. |
| 2019/0018095 A1 | 1/2019 | Mileski et al. |
| 2019/0018096 A1 | 1/2019 | Poole et al. |
| 2019/0025389 A1 | 1/2019 | McNulty et al. |
| 2019/0033402 A1 | 1/2019 | McNulty et al. |
| 2019/0033414 A1 | 1/2019 | Sofka et al. |
| 2019/0033415 A1 | 1/2019 | Sofka et al. |
| 2019/0033416 A1 | 1/2019 | Rothberg et al. |
| 2019/0038233 A1 | 2/2019 | Poole et al. |
| 2019/0086497 A1 | 3/2019 | Rearick et al. |
| 2019/0101607 A1 | 4/2019 | Rothberg et al. |
| 2019/0162806 A1 | 5/2019 | Poole et al. |
| 2019/0178962 A1 | 6/2019 | Poole et al. |
| 2019/0178963 A1 | 6/2019 | Poole et al. |
| 2019/0227136 A1 | 7/2019 | Mileski et al. |
| 2019/0227137 A1 | 7/2019 | Mileski et al. |
| 2019/0250227 A1 | 8/2019 | McNulty et al. |
| 2019/0250228 A1 | 8/2019 | McNulty et al. |
| 2019/0257903 A1 | 8/2019 | Poole et al. |
| 2019/0324098 A1 | 10/2019 | McNulty et al. |
| 2019/0353720 A1 | 11/2019 | Dyvorne et al. |
| 2019/0353723 A1 | 11/2019 | Dyvorne et al. |
| 2019/0353726 A1 | 11/2019 | Poole et al. |
| 2019/0353727 A1 | 11/2019 | Dyvorne et al. |
| 2020/0011952 A1 | 1/2020 | Rothberg et al. |
| 2020/0018806 A1 | 1/2020 | Rothberg et al. |
| 2020/0022611 A1 | 1/2020 | Nelson et al. |
| 2020/0022612 A1 | 1/2020 | McNulty et al. |
| 2020/0022613 A1 | 1/2020 | Nelson et al. |
| 2020/0025846 A1 | 1/2020 | Nelson et al. |
| 2020/0025851 A1 | 1/2020 | Rearick et al. |
| 2020/0033431 A1 | 1/2020 | Schlemper et al. |
| 2020/0034998 A1 | 1/2020 | Schlemper et al. |
| 2020/0041588 A1 | 2/2020 | O'Halloran et al. |
| 2020/0045112 A1 | 2/2020 | Sacolick et al. |
| 2020/0058106 A1 | 2/2020 | Lazarus et al. |
| 2020/0200844 A1 | 6/2020 | Boskamp et al. |
| 2020/0209334 A1 | 7/2020 | O'Halloran et al. |
| 2020/0289019 A1 | 9/2020 | Schlemper et al. |
| 2020/0289022 A1 | 9/2020 | Coumans et al. |
| 2020/0294229 A1 | 9/2020 | Schlemper et al. |
| 2020/0294282 A1 | 9/2020 | Schlemper et al. |
| 2020/0294287 A1 | 9/2020 | Schlemper et al. |
| 2020/0337587 A1 | 10/2020 | Sacolick et al. |
| 2020/0355765 A1 | 11/2020 | Chen et al. |
| 2021/0048498 A1 | 2/2021 | Dyvorne et al. |

FOREIGN PATENT DOCUMENTS

| | | |
|---|---|---|
| CN | 101563031 A | 10/2009 |
| CN | 102665543 A | 9/2012 |
| CN | 103703383 A | 4/2014 |
| CN | 103957786 A | 7/2014 |
| JP | S59-99239 A | 6/1984 |
| JP | S60-12044 A | 1/1985 |
| JP | H03-23842 A | 1/1991 |
| JP | H06-261878 A | 9/1994 |
| JP | 2010-029313 A | 2/2010 |

OTHER PUBLICATIONS

U.S. Appl. No. 16/151,221, filed Oct. 3, 2018, Poole et al.
Invitation to Pay Additional Fees for International Application No. PCT/US2016/32014 dated Jul. 13, 2016.
International Search Report and Written Opinion for International Application No. PCT/US2016/32014 dated Sep. 28, 2016.
Extended European Search Report for European Application No. 16793502.2 dated Nov. 30, 2018.
Communication pursuant to Article 94(3) EPC for European Application No. 16793502.2 dated Nov. 16, 2021.
Coffey et al., A Large vol. Double Channel 1H-X RF Probe for Hyperpolarized Magnetic Resonance at 0.0475 Tesla. J Magn Reson. 2012;220:1-18.
Lapierre et al., Parallel Imaging and Acceleration in the Johnson Noise Dominated Regime. Proceedings of the International Society for Magnetic Resonance in Medicine. ISMRM 21$^{st}$ Annual Meeting and Exhibition. 2013. 2772.

* cited by examiner

RADIO FREQUENCY COIL METHODS AND APPARATUS

CROSS-REFERENCE TO RELATED APPLICATIONS

This application claims the benefit under 35 U.S.C. § 120 and is a Continuation of U.S. application Ser. No. 15/152,951, filed May 12, 2016, entitled RADIO FREQUENCY COIL METHODS AND APPARATUS, which claims priority under 35 U.S.C. § 119 to U.S. Provisional Patent Application Ser. No. 62/160,036, filed May 12, 2015, titled RECEIVE COIL OPTIMIZATION METHODS AND APPARATUS, and U.S. Provisional Patent Application Ser. No. 62/169,102, filed Jun. 1, 2015, titled COIL OPTIMIZATION METHODS AND APPARATUS, each of which is hereby incorporated by reference in its entirety.

BACKGROUND

Magnetic resonance imaging (MRI) provides an important imaging modality for numerous applications and is widely utilized in clinical and research settings to produce images of the inside of the human body. As a generality, MRI is based on detecting magnetic resonance (MR) signals, which are electromagnetic waves emitted by atoms in response to state changes resulting from applied electromagnetic fields. For example, nuclear magnetic resonance (NMR) techniques involve detecting MR signals emitted from the nuclei of excited atoms upon the re-alignment or relaxation of the nuclear spin of atoms in an object being imaged (e.g., atoms in the tissue of the human body). Detected MR signals may be processed to produce images, which in the context of medical applications, allows for the investigation of internal structures and/or biological processes within the body for diagnostic, therapeutic and/or research purposes.

MRI provides an attractive imaging modality for biological imaging due to the ability to produce non-invasive images having relatively high resolution and contrast without the safety concerns of other modalities (e.g., without needing to expose the subject to ionizing radiation, e.g., x-rays, or introducing radioactive material to the body). Additionally, MRI is particularly well suited to provide soft tissue contrast, which can be exploited to image subject matter that other imaging modalities are incapable of satisfactorily imaging. Moreover, MR techniques are capable of capturing information about structures and/or biological processes that other modalities are incapable of acquiring. However, there are a number of drawbacks to MRI that, for a given imaging application, may involve the relatively high cost of the equipment, limited availability and/or difficulty in gaining access to clinical MRI scanners and/or the length of the image acquisition process.

The trend in clinical MRI has been to increase the field strength of MRI scanners to improve one or more of scan time, image resolution, and image contrast, which, in turn, continues to drive up costs. The vast majority of installed MRI scanners operate at 1.5 or 3 tesla (T), which refers to the field strength of the main magnetic field $B_0$. A rough cost estimate for a clinical MRI scanner is approximately one million dollars per tesla, which does not factor in the substantial operation, service, and maintenance costs involved in operating such MRI scanners.

Additionally, conventional high-field MRI systems typically require large superconducting magnets and associated electronics to generate a strong uniform static magnetic field ($B_0$) in which an object (e.g., a patient) is imaged. The size of such systems is considerable with a typical MRI installment including multiple rooms for the magnet, electronics, thermal management system, and control console areas. The size and expense of MRI systems generally limits their usage to facilities, such as hospitals and academic research centers, which have sufficient space and resources to purchase and maintain them. The high cost and substantial space requirements of high-field MRI systems results in limited availability of MRI scanners. As such, there are frequently clinical situations in which an MRI scan would be beneficial, but due to one or more of the limitations discussed above, is not practical or is impossible, as discussed in further detail below.

SUMMARY

The inventors have developed radio frequency components that, in some embodiments, are configured to improve magnetic resonance signal detection to, for example, facilitate image acquisition at low field strengths. Some embodiments include a radio frequency coil configured to be responsive to magnetic resonance signals, the radio frequency coil comprising at least one conductor arranged in a three dimensional geometry about a region of interest in a configuration optimized to increase sensitivity to magnetic resonance signals emitted within the region of interest.

Some embodiments include a radio frequency component configured to be responsive to magnetic resonance signals, the radio frequency component comprising a first coil, including a first conductor arranged in a plurality of turns, oriented to be responsive to first magnetic resonance signal components, and a second coil, including a second conductor arranged in a plurality of turns, oriented to be responsive to second magnetic resonance signal components.

Some embodiments include a radio frequency component configured to be responsive to magnetic resonance signals, the radio frequency component comprising a first coil including a first conductor arranged in a plurality of turns oriented to be responsive to magnetic resonance signal components along a first principal axis, and a second coil including a second conductor arranged in a plurality of turns oriented to be responsive to magnetic resonance signal components along a second principal axis oriented differently than the first principal axis.

Some embodiments include a radio frequency component configured to be responsive to magnetic resonance signals, the radio frequency component comprising a first coil including a first conductor having a plurality of turns arranged about a region of interest, and a second coil including a second conductor having a plurality of turns arranged about the region of interest and offset from the first coil away from the region of interest.

Some embodiments include a radio frequency coil configured to be responsive to magnetic resonance signals, the radio frequency coil comprising at least one conductor arranged in a three dimensional geometry about a region of interest, wherein a coil configuration of the at least one conductor in the three dimensional geometry is determined based, at least in part, on performing at least one optimization using a model of the radio frequency coil.

Some embodiments include a method of determining a configuration for a radio-frequency coil comprising generating a model of the radio-frequency coil, and performing an optimization to determine a model configuration that satisfies at least one constraint and that, when operation of the model is simulated, produces a magnetic field that satisfies a predetermined criteria.

Some embodiments include a radio frequency coil configured for a portion of a body of a patient, the radio frequency coil comprising at least one conductor arranged in a plurality of turns about a region of interest and oriented to be responsive to magnetic resonance signal components oriented substantially orthogonal to a longitudinal axis of the target anatomy of the patient.

Some embodiments include an apparatus for use in a magnetic resonance imaging system, the apparatus comprising a first coil, and at least one controller configured to operate the coil to generate a radio frequency magnetic field and a gradient field.

Some embodiments include a radio frequency coil configured for a portion of human anatomy, the radio frequency coil comprising at least one conductor arranged in a three dimensional geometry about a region of interest, the at least one conductor forming a plurality of turns, wherein spacing between the plurality of turns is non-uniform.

Some embodiments include a low-field magnetic resonance system comprising a B0 magnet configured to produce a low-field strength B0 magnetic field to provide a field of view, a first coil configured to be responsive to first magnetic resonance signal components emitted from the field of view, and a second coil configured to be responsive to second magnetic resonance signal components emitted from the field of view.

BRIEF DESCRIPTION OF THE DRAWINGS

Various aspects and embodiments of the disclosed technology will be described with reference to the following figures. It should be appreciated that the figures are not necessarily drawn to scale.

DETAILED DESCRIPTION

Figure 1:
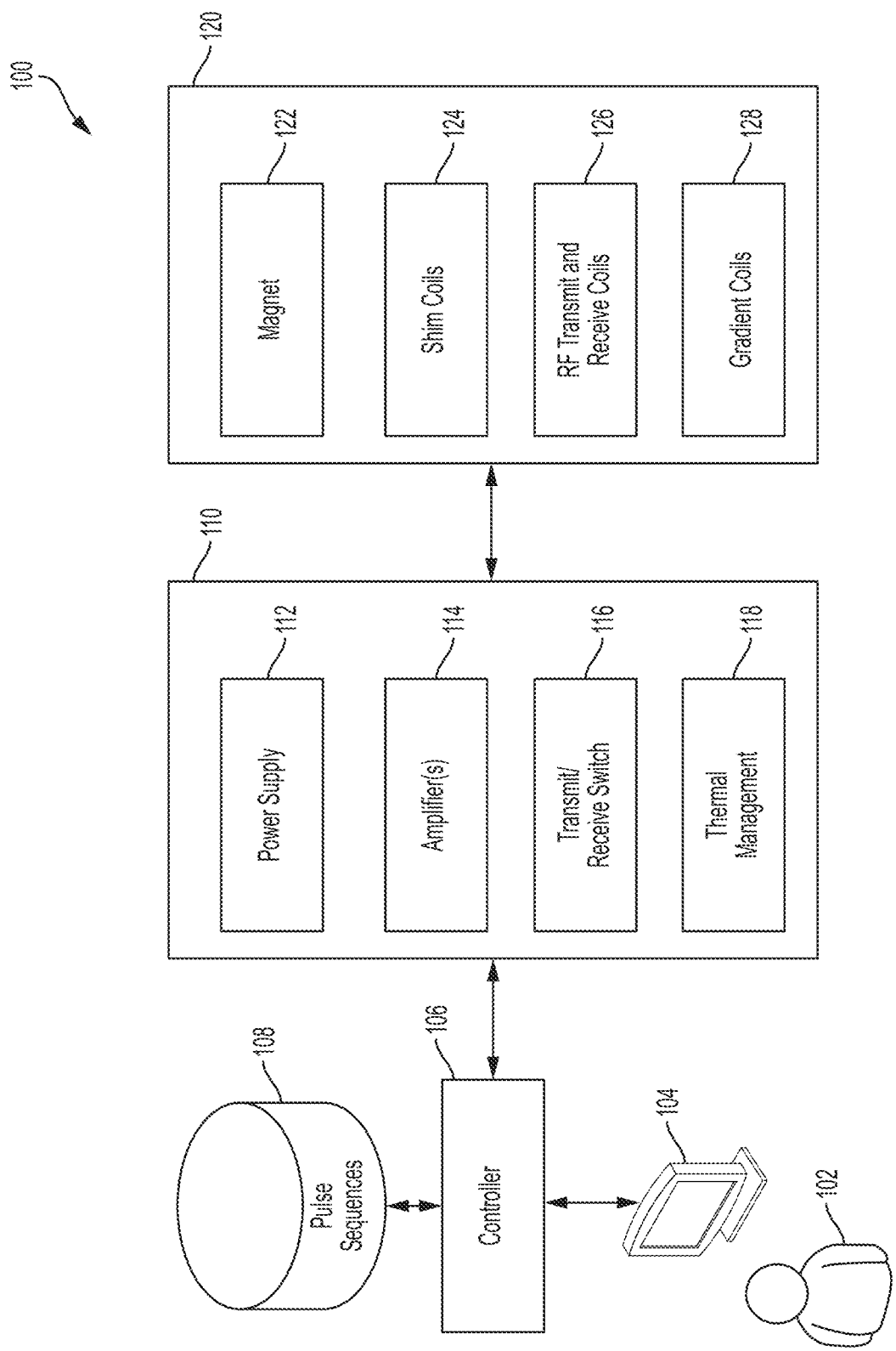
FIG. 1 illustrates a block diagram of an exemplary magnetic resonance imaging system, in accordance with some embodiments.

The MRI scanner market is overwhelmingly dominated by high-field systems, and particularly for medical or clinical MRI applications. As discussed above, the general trend in medical imaging has been to produce MRI scanners with increasingly greater field strengths, with the vast majority of clinical MRI scanners operating at 1.5 T or 3 T, with higher field strengths of 7 T and 9 T used in research settings. As used herein, "high-field" refers generally to MRI systems presently in use in a clinical setting and, more particularly, to MRI systems operating with a main magnetic field (i.e., a B0 field) at or above 1.5 T, though clinical systems operating between 0.5 T and 1.5 T are often also characterized as "high-field." By contrast, "low-field" refers generally to MRI systems operating with a B0 field of less than or equal to approximately 0.2 T, though systems having a B0 field of between 0.2 T and approximately 0.3 T have sometimes been characterized as low-field as field strengths have increased in the high-field regime.

Low-field MRI has been explored in limited contexts for non-imaging research purposes and narrow and specific contrast-enhanced imaging applications, but is conventionally regarded as being unsuitable for producing clinically useful images, particularly at field strengths substantially below 0.2 T (e.g., 100 mT or less). For example, the resolution, contrast, and/or image acquisition time is generally not regarded as being suitable for clinical purposes such as, but not limited to, tissue differentiation, blood flow or perfusion imaging, diffusion-weighted (DW) or diffusion tensor (DT) imaging, functional MRI (fMRI), etc. The inventors have developed techniques for producing improved quality, portable and/or lower-cost low-field MRI systems that can improve the wide-scale deployability of MRI technology in a variety of environments beyond the large MRI installments at hospitals and research facilities.

A challenge in low-field MRI is the relatively low signal-to-noise ratio. In particular, the signal-to-noise ratio of an MR signal is related to the strength of the main magnetic field B0, and is one of the factors driving clinical systems to operate in the high-field regime. Thus, the MR signal strength is relatively weak in the low-field context due to the low field strengths, increasing the importance of being able to detect as much signal as possible. Some aspects of the inventors' contribution derive from their recognition that performance of a low-field MRI system may be improved by optimizing the configuration of radio frequency (RF) transmit and/or receive coils (referred to herein as RF transmit/receive coils or simply RF coils) to improve the ability of the RF transmit/receive coils to transmit magnetic fields and detect emitted MR signals. As discussed above, low-field MRI systems produce weaker MR signals than their high-field counterparts, making it more important that RF transmit/receive coils operate optimally (e.g., by both transmitting optimal magnetic pulses and detecting as much of the emitted MR signals with as much fidelity as possible) in view of the lower signal-to-noise ratio (SNR).

Briefly, MRI involves placing a subject to be imaged (e.g., all or a portion of a patient) in a static, homogenous magnetic field B0 to align a subject's atomic net magnetization (often represented by a net magnetization vector) in the direction of the B0 field. One or more transmit coils are then used to generate a pulsed magnetic field B1 having a frequency related to the rate of precession of atomic spins of the atoms in the magnetic field B0 to cause the net magnetization of the atoms to develop a component in a direction transverse to the direction of the B0 field. After the B1 field is turned off, the transverse component of the net magnetization vector precesses, its magnitude decaying over time until the net magnetization re-aligns with the direction of the B0 field if allowed to do so. This process produces MR signals that can be detected, for example, by electrical signals induced in one or more receive coils of the MRI system that are tuned to resonate at the frequency of the MR signals.

MR signals are rotating magnetic fields, often referred to as circularly polarized magnetic fields that can be viewed as comprising linearly polarized components along orthogonal axes. That is, an MR signal is composed of a first sinusoidal component that oscillates along a first axis and a second sinusoidal component that oscillates along a second axis orthogonal to the first axis. The first sinusoidal component and the second sinusoidal component oscillate 90° out-of-phase with each other. An appropriately arranged coil tuned to the resonant frequency of the MR signals can detect a linearly polarized component along one of the orthogonal axes. In particular, an electrical response may be induced in a tuned receive coil by the linearly polarized component of an MR signal that is oriented along an axis approximately orthogonal to the current loop of the coil, referred to herein as the principal axis of the coil.

Accordingly, MRI is performed by exciting and detecting emitted MR signals using transmit/receive coils (also referred to interchangeably as radio-frequency (RF) coils or Tx/Rx coils), which may include separate coils for transmitting and receiving, multiple coils for transmitting and/or receiving, or the same coils for transmitting and receiving. To transmit excitation pulse sequences and to detect emitted MR signals, transmit/receive coils must resonate at a frequency dependent on the strength of the B0 field. Accordingly, transmit/receive coils in the high-field regime must resonate at significantly higher frequencies (shorter wavelengths) than their low-field counterparts. The length of a conducting path of a resonant coil is constrained by the frequency at which the resonant coil is intended to resonate. In particular, the higher the frequency, the shorter the conductive path must be for the resonant coil to operate satisfactorily. Thus, the conducting paths of high-field transmit/receive coils are required to be very short. To meet this requirement, high-field transmit/receive coils are frequently single turn conductive loops formed by etching, cutting or milling conductive sheets (e.g., copper sheets). Typical conducting paths for high-field transmit/receive coils are limited in length to tens of centimeters.

The low frequencies involved in low-field MRI permit the conducting paths of transmit/receive coils to be quite long, allowing for coil designs that are not suitable (or useable) for high-field MRI due to the constraints on conductive path length imposed by the high frequencies involved in high-field MRI. According to some embodiments, a transmit/receive coil may be formed using a single conducting path provided over a three-dimensional surface corresponding to a region of interest. Due, in part, to relaxation of the constraint on conductor length, the conducting path of the transmit/receive may be arranged over the three-dimensional surface in a plurality of turns or loops. As used herein, a "turn" refers to a conductive path provided 360° or substantially 360° about a reference axis (e.g., the principal axis of the coil, as discussed in further detail below). It should be appreciated that a turn need not form a closed loop provided the conductive path is formed substantially 360° about the reference axis. For example, a conductor arranged in a spiral geometry may comprise multiple turns, though each turn does not form a closed loop. Exemplary coils having conductors arranged in a plurality of turns are discussed in further detail below. By providing a coil having multiple turns (e.g., 5, 10, 15, 20, 30, 50 turns or more), the sensitivity of the coil in responding to MR signals can be improved.

The increase in allowable conductor length also allows for coils having a single conductor arranged to cover an arbitrary geometry to facilitate transmit/receive coils configured for desired portions of the anatomy. To image the head, for example, a low-field transmit/receive head coil may be produced by winding a conductor about a substrate manufactured to be worn by a person as a helmet. The conductor may be arranged, for example, by positioning (e.g., winding) the conductor in a spiral geometry about the surface of the helmet to provide coverage sufficient to provide transmit pulses to a region of interest (e.g., the brain or a portion thereof) and/or to detect MR signals emitted from the region of interest. As another example, to image the torso or an appendage (e.g., a leg or a portion thereof, such as the knee), a conductor may be similarly arranged in a spiral geometry about a surface configured to accommodate the desired anatomy.

The above describe transmit/receive coil geometry is made possible by aspects of the low-field regime. As discussed above, the low field strengths allow for significantly longer conductive paths to be utilized. In addition, clinical high-field MRI systems typically generate a B0 field via a solenoid coil wound about a cylindrical bore into which the patient being imaged is inserted. As such, the B0 field is oriented along the longitudinal axis of the bore and the body inserted therein. To perform MRI, transmit/receive coils produce a B1 field perpendicular to the B0 field and detect emitted MR signals in this transverse direction. This places restrictions on the geometry for transmit/receive coils designed for high-field MRI. Low-field MRI facilitates the design of "open" systems in which the B0 field is generated using, for example, bi-planar magnets between which a patient being imaged is placed such that the B0 field is substantially oriented perpendicular to the longitudinal axis of the body. For example, any of the low-field systems described in U.S. application Ser. No. 14/845,652 ('652 Application), titled "Low-field Magnetic Resonance Imaging Methods and Apparatus," and filed Sep. 4, 2015, or U.S. application Ser. No. 14/846,255 ('255 Application), titled "Ferromagnetic Augmentation for Magnetic Resonance Imaging," and filed Sep. 4, 2015, each of which is herein incorporated by reference in its entirety.

Accordingly, transmit/receive coils are arranged to produce and/or detect magnetic fields transverse to this B0 field, allowing for geometries not possible in traditional high-field MRI systems. As a result, B0 magnets configured in arrangements that produce a B0 field that is transverse to the axis of the body (e.g., bi-planar B0 magnets) allow for the design of transmit/receive coils that produce/detect magnetic fields in the axial direction of the body, some examples of which are described in further detail below. Transmit/receive coils configured to respond to MR signal components oriented substantially along the longitudinal axis of the body or specific target anatomy (i.e., coils configured with a principal axis substantially aligned with the longitudinal axis of the body) are generally not useable with B0 coils that produce magnetic fields aligned with the axis of the body, such as those commonly used in high-field MRI. However, it should be appreciated that transmit/receive coils may also be configured to perform MR signal detection in conjunction with MRI systems having a B0 magnet that produces a B0 field in a direction aligned with the longitudinal axis of the body (e.g., B0 magnet having a solenoid geometry). In particular, according to some embodiments, an RF coil is provided having a conductor with a plurality of turns configured to respond to MR signal components oriented orthogonal to the longitudinal axis of the body, some examples of which are described in further detail below.

The inventors have appreciated that one or more of the different factors regarding transmit/receive coils in the high-field and low-field context facilitate optimizing the design for transmit/receive coils for use in low-field MRI. To this end, the inventors have developed techniques for optimizing the configuration of RF coils to improve the performance of the coils for use with a low-field MRI system.

The inventors have appreciated that factors arising from the low-field context facilitate the use of magnetic field synthesis techniques to produce generally optimal coil designs for RF coils. Magnetic field synthesis is a technique for modeling coil(s) and simulating the magnetic fields generated by the modeled coil(s) when energized. Parameters of the coil models may then be adjusted to find a set of parameters that generate a desired magnetic field according to some criteria given one or more constraints on the coil models and/or parameters of the coil models. Due to several factors, magnetic field synthesis techniques were heretofore generally inapplicable to designing RF coils for high-field MRI systems. In particular, such magnetic field synthesis techniques were not effective in designing RF coils for use with high-field MRI systems due in part to the relatively high frequencies at which such coils are required to resonate when used in the high-field regime. Specifically, the higher the frequency of operation, the shorter the current paths required to transmit and receive. As a result, known magnetic field synthesis techniques were not useful in designing receive coils with the short current paths needed, for example, to detect MR signals in the high-field context. For example, magnetic synthesis techniques may not be useful and/or or needed to configure a single turn conductor with a short current path typically used in high-field MRI.

As discussed above, the significantly lower operation frequencies for transmit and receive in low-field MRI (i.e., the significantly lower frequencies of transmit pulses and of emitted MR signals) allow for substantially longer current paths than for high-field MRI, which has led to innovative new designs for RF coils for use in low-field MRI systems. For example, a general rule of thumb is that the length of the conductor in a resonant coil should not exceed one tenth of the wavelength at the resonant frequency. Thus, a high-field MRI system with a B0 magnetic field of 3 T operates at approximately 128 MHz and so has a wavelength of approximately 2.3 meters. Thus, the length of the conductors in the transmit/receive coils for such a high-field system should not exceed 23 centimeters. By contrast, a low-field MRI system with a B0 field of 0.1 T operates at approximately 4.3 MHz and so has a wavelength of approximately 70 meters and therefore transmit/receive coils can include conductors having lengths up to approximately 7 meters. A low-field MRI system with a B0 field of 0.05 T operates at approximately 2.15 MHz (~140 meter wavelength) and corresponding transmit/receive coils can utilize conductors having lengths up to 14 meters, and so on. The inventors have recognized that the significantly longer conductor lengths permitted in the low-field regime allow for transmit/receive coil configurations not possible in the high-field regime. In addition, the increased conductor lengths facilitate the use of magnetic field synthesis to determine optimal transmit/receive coil configurations.

The inventors have recognized that magnetic field synthesis techniques may be used to design RF coils for low-field MRI, and have developed techniques to optimize the configuration of RF coil(s) to improve transmission efficiency and/or improve efficacy in detecting MR signals emitted in a low-field MRI environment. The inventors have developed RF coil configurations that increase the sensitivity of MR signal detection, thus improving the SNR of the system.

As discussed above, MR signals are rotating or circularly polarized magnetic fields. The inventors have developed RF coil designs configured for the low-field regime comprising a plurality of coils having respective different principal axes to respond to differently oriented magnetic field components of MR signals (herein referred to as MR signal components) to improve the SNR of MR signal detection. For example, a first coil and a second coil may be arranged to have respective principal axes that are orthogonal or substantially orthogonal to one another (i.e., quadrature coils) to respond to orthogonal components of emitted MR signals (e.g., to detect orthogonal linearly polarized components of a circularly polarized MR signal). In this manner, the pair of coils obtain dual measurements of an MR signal shifted in phase by 90°, which measurements may be used to improve the SNR of MR signal detection by, for example, combining the dual measurements, as discussed in further detail below.

It should be appreciated that the respective principal axes of a plurality of coils may be oriented with respect to each other in other relationships (e.g., non-orthogonal relationships). For example, orthogonality of the principal axes of a pair of coils for a given surface may be difficult to achieve. In general, the improvement in SNR increases the closer the principal axes of a pair of coils are to orthogonal, up to an improvement of the square root of two. Additionally, coils for which the principal axes are not orthogonal may exhibit mutual inductance and may require configuring the respective coils in a manner to mitigate mutual inductance, some techniques of which are described in further detail below.

According to some embodiments, an RF transmit/receive component configured to respond to MR signals comprises a first coil formed by at least one conductor arranged in a plurality of turns or loops according to a first coil configuration having a first principal axis and a second coil formed by at least one conductor arranged in a plurality of turns or loops according to a second coil configuration having a second principal axis different from the first principal axis. For example, the first coil configuration and the second coil configuration may be such that the first principal axis and the second principal axis are substantially orthogonal to one another, although other relationships between the respective principal axes may be used as well. In this manner, the first and second coils can detect different components of an MR signal (e.g., orthogonal linearly polarized components of a circularly polarized MR signal) to improve the SNR of MR signal detection. According to some embodiments, the first and second coil configurations for the first and second coils, respectively, are determined using magnetic synthesis techniques, though the coil configurations may be determined using other techniques (e.g., human intuition, empirically, etc.), as the aspects are not limited in this respect. According to some embodiments, the first coil and the second coil are arranged on separate layers of a support structure to provide an RF transmit/receive component having improved SNR, some examples of which are described in further detail below.

The inventors have further appreciated that an optimal configuration for a receive coil may differ from one individual to another. For example, the size and shape of an individual's head may impact the optimal configuration for an RF coil for that individual. To address this variability, the inventors have developed techniques for optimizing one or more receive coils for a specific individual. According to some embodiments, measurements of a target anatomy (e.g., head measurements, torso measurements, appendage measurements, etc.) of the specific individual are obtained and the optimization techniques described herein are performed using the obtained measurements. As a result, an optimal configuration for receive coil(s) may be obtained for a specific individual. According to some embodiments, a support for the receive coils for the target anatomy (e.g., a helmet) is fabricated (e.g., via three-dimensional (3D) printing) in accordance with the optimal configuration determined. As a result, an optimal RF coil can be quickly and cost effectively produced and may be customized for a particular individual and/or portion of the anatomy.

The techniques described herein enable radio frequency components having improved sensitivity to MR signals, thus increasing the signal-to-noise ratio of MR signal detection. As discussed above, relatively weak MR signals are a challenge of low-field MRI. Thus, transmit/receive components produced using one or more techniques described herein facilitate low-field MRI systems capable of acquiring clinically useful images (e.g., images having resolutions suitable for clinical purposes, for example, diagnostic, therapeutic and/or research purposes). In this respect, some embodiments include a low-field MRI system comprising a radio frequency coil having at least one conductor arranged in a three dimensional geometry about a region of interest in a configuration optimized to increase sensitivity to MR signals emitted within the region of interest. For example, the low-field MRI system may comprise a B0 magnet configured to produce a low-field strength (e.g., between 0.2 T and 0.1 T, between 0.1 T and 50 mT, between 50 mT and 20 mT, between 20 mT and 10 mT, etc.) B0 magnetic field having a field of view, wherein the radio frequency coil is optimized to provide radio frequency pulses to the field of view to cause an MR response and/or to detect MR signals emitted therefrom with improved efficacy.

Some embodiments include a dual coil radio frequency component having a pair of coils configured for the low-field regime and oriented to respond to different MR signal components to improve the signal-to-noise ratio of MR signal detection. For example, some embodiments include a low-field magnetic resonance system comprising a B0 magnet configured to produce a low-field strength (e.g., between 0.2 T and 0.1 T, between 0.1 T and 50 mT, between 50 mT and 20 mT, between 20 mT and 10 mT, etc.) B0 magnetic field having a field of view suitable for imaging, a first coil configured to be responsive to first MR signal components emitted from the field of view, and a second coil configured to be responsive to second MR signal components emitted from the field of view. In this respect, to respond to MR signals emitted from the field of view of the low-field strength B0 magnetic field, the first coil and the second coil are configured to detect MR signals at frequencies corresponding to the B0 magnetic field (i.e., in the low-field regime).

According to some embodiments, the first coil and second coil are arranged to respond to orthogonal MR signal components (e.g., the principal axes of the first coil and the second coil are substantially orthogonal to one another) to maximize the boost in SNR, although other arrangements can be used as well. According to some embodiments, the first coil and the second coil are offset from one another relative to the field of view. According to some embodiments, the respective configurations of the first coil and the second coil are optimized, for example, using magnetic synthesis techniques, though the respective configurations may be determined using other techniques (e.g., intuition, empirically, etc.).

According to some embodiments, the B0 magnet of a low-field MRI system is arranged in a planar geometry (e.g., a single-sided or a bi-planar geometry) and in other embodiments the B0 magnet is arranged in a cylindrical geometry (e.g., a solenoid geometry), and the one or more radio frequency coils are configured to transmit radio frequency pulses and/or detect MR signals in accordance with the geometry of the B0 magnet.

Following below are more detailed descriptions of various concepts related to, and embodiments of, methods and apparatus for producing RF coils, for example, for use in low-field MRI. It should be appreciated that the embodiments described herein may be implemented in any of numerous ways. Examples of specific implementations are provided below for illustrative purposes only. It should be appreciated that the embodiments and the features/capabilities provided may be used individually, all together, or in any combination of two or more, as aspects of the technology described herein are not limited in this respect.

FIG. 1 is a block diagram of exemplary components of a MRI system 100 (e.g., a low-field MRI system). In the illustrative example of FIG. 1, MRI system 100 comprises computing device 104, controller 106, pulse sequences store 108, power management system 110, and magnetics components 120. It should be appreciated that system 100 is illustrative and that a MRI system may have one or more other components of any suitable type in addition to or instead of the components illustrated in FIG. 1.

As illustrated in FIG. 1, magnetics components 120 comprise $B_0$ magnet 122, shim coils 124, RF transmit and receive coils 126, and gradient coils 128. Magnet 122 may be used to generate the main magnetic field $B_0$. Magnet 122 may be any suitable type or combination of magnetics components that can generate a desired main magnetic $B_0$ field (e.g., any one or combination of electromagnet(s), printed magnetics, permanent magnet(s), etc.). Thus, a $B_0$ magnet refers herein to any one or combination of magnetics components of any type configured to produce a $B_0$ field. According to some embodiments, $B_0$ magnet 122 may produce or contribute to a B0 field greater than or equal to approximately 20 mT and less than or equal to approximately 50 mT, greater than or equal to approximately 50 mT and less than or equal to approximately 0.1 T, greater than or equal to approximately 0.1 T and less than or equal to approximately 0.2 T, greater than or equal to approximately 0.2 T and less than or equal to approximately 0.3 T, greater than 0.3 T and less than or equal to approximately 0.5 T, etc. Shim coils 124 may be used to contribute magnetic field(s) to improve the homogeneity of the $B_0$ field generated by magnet 122.

Gradient coils 128 may be arranged to provide gradient fields and, for example, may be arranged to generate gradients in the B0 field in three substantially orthogonal directions (X, Y, Z). Gradient coils 128 may be configured to encode emitted MR signals by systematically varying the B0 field (the B0 field generated by magnet 122 and/or shim coils 124) to encode the spatial location of received MR signals as a function of frequency or phase. For example, gradient coils 128 may be configured to vary frequency or phase as a linear function of spatial location along a particular direction, although more complex spatial encoding profiles may also be provided by using nonlinear gradient coils. For example, a first gradient coil may be configured to selectively vary the B0 field in a first (X) direction to perform frequency encoding in that direction, a second gradient coil may be configured to selectively vary the B0 field in a second (Y) direction substantially orthogonal to the first direction to perform phase encoding, and a third gradient coil may be configured to selectively vary the B0 field in a third (Z) direction substantially orthogonal to the first and second directions to enable slice selection for volumetric imaging applications.

As discussed above, MRI is performed by exciting and detecting emitted MR signals using transmit and receive coils, respectively (often referred to as radio frequency (RF) coils). Transmit/receive coils may include separate coils for transmitting and receiving, multiple coils for transmitting and/or receiving, or the same coils for transmitting and receiving. Thus, a transmit/receive component may include one or more coils for transmitting, one or more coils for receiving and/or one or more coils for transmitting and receiving. Transmit/receive coils are also often referred to as Tx/Rx or Tx/Rx coils to generically refer to the various configurations for the transmit and receive magnetics component of an MRI system. These terms are used interchangeably herein. In FIG. 1, RF transmit and receive coils 126 comprise one or more transmit coils that may be used to generate RF pulses to induce an oscillating magnetic field B1. The transmit coil(s) may be configured to generate any suitable types of RF pulses. For example, the transmit coil(s) may be configured to generate any of the pulse sequences described in U.S. patent application Ser. No. 14/938,430 ('430 application), titled "Pulse Sequences for Low Field Magnetic Resonance," filed Nov. 11, 2015, which is herein incorporated by reference in its entirety.

Each of magnetics components 120 may be constructed in any suitable way. For example, in some embodiments, one or more (e.g., all) of magnetics components 120 may be fabricated, constructed or manufactured using techniques described in U.S. patent application Ser. No. 14/845,652 ('652 application), titled "Low-field Magnetic Resonance Imaging Methods and Apparatus," and filed Sep. 4, 2015, which is herein incorporated by reference in its entirety. However, the techniques described herein are not limited in this respect, as any suitable technique may be used to provide the magnetics components 120.

Power management system 110 includes electronics to provide operating power to one or more components of the low-field MRI system 100. For example, as discussed in more detail below, power management system 110 may include one or more power supplies, gradient power components, transmit coil components, and/or any other suitable power electronics needed to provide suitable operating power to energize and operate components of the low-field MRI system 100.

As illustrated in FIG. 1, power management system 110 comprises power supply 112, power component(s) 114, transmit/receive switch 116, and thermal management components 118. Power supply 112 includes electronics to provide operating power to magnetic components 120 of the MRI system 100. For example, power supply 112 may include electronics to provide operating power to one or more $B_0$ coils (e.g., $B_0$ magnet 122) to produce the main magnetic field for the low-field MRI system. In some embodiments, power supply 112 is a unipolar, continuous wave (CW) power supply, however, any suitable power supply may be used. Transmit/receive switch 116 may be used to select whether RF transmit coils or RF receive coils are being operated.

Power component(s) 114 may include one or more RF receive (Rx) pre-amplifiers that amplify MR signals detected by one or more RF receive coils (e.g., coils 126), one or more RF transmit (Tx) power components configured to provide power to one or more RF transmit coils (e.g., coils 126), one or more gradient power components configured to provide power to one or more gradient coils (e.g., gradient coils 128), and one or more shim power components configured to provide power to one or more shim coils (e.g., shim coils 124).

Thermal management components 118 provide cooling for components of low-field MRI system 100 and may be configured to do so by facilitating the transfer of thermal energy generated by one or more components of the low-field MRI system 100 away from those components. Thermal management components 118 may include, without limitation, components to perform water-based or air-based cooling, which may be integrated with or arranged in close proximity to MRI components that generate heat including, but not limited to, $B_0$ coils, gradient coils, shim coils, and/or transmit/receive coils. Thermal management components 118 may include any suitable heat transfer medium including, but not limited to, air and liquid coolant (e.g., water), to transfer heat away from components of the low-field MRI system 100.

As illustrated in FIG. 1, MRI system 100 includes controller 106 (also referred to as a console) having control electronics to send instructions to and receive information from power management system 110. Controller 106 may be configured to implement one or more pulse sequences, which are used to determine the instructions sent to power management system 110 to operate the magnetic components 120 in a desired sequence. For example, for embodiments wherein MRI system 100 operates at low-fields, controller 106 may be configured to control power management system 110 to operate the magnetic components 120 in accordance with a zero echo time (ZTE) pulse sequence, a balanced steady-state free precession pulse sequence (bSSFP), a gradient echo pulse sequence, a spin echo pulse sequence, an inversion recovery pulse sequence, arterial spin labeling, diffusion weighted imaging (DWI), and/or any other pulse sequence specified for operation in the low-field context. Pulse sequences for low-field MRI may be applied for different contrast types such as T1-weighted and T2-weighted imaging, diffusion-weighted imaging, arterial spin labeling (perfusion imaging), Overhauser imaging, etc. However, any pulse sequence may be used, as the aspects are not limited in this respect. Controller 106 may be implemented as hardware, software, or any suitable combination of hardware and software, as aspects of the disclosure provided herein are not limited in this respect.

In some embodiments, controller 106 may be configured to implement a pulse sequence by obtaining information about the pulse sequence from pulse sequences repository 108, which stores information for each of one or more pulse sequences. Information stored by pulse sequences repository 108 for a particular pulse sequence may be any suitable information that allows controller 106 to implement the particular pulse sequence. For example, information stored in pulse sequences repository 108 for a pulse sequence may include one or more parameters for operating magnetics components 120 in accordance with the pulse sequence (e.g., parameters for operating the RF transmit and receive coils 126, parameters for operating gradient coils 128, etc.), one or more parameters for operating power management system 110 in accordance with the pulse sequence, one or more programs comprising instructions that, when executed by controller 106, cause controller 106 to control system 100 to operate in accordance with the pulse sequence, and/or any other suitable information. Information stored in pulse sequences repository 108 may be stored on one or more non-transitory storage media.

As illustrated in FIG. 1, controller 106 also interacts with computing device 104 programmed to process received MR data. For example, computing device 104 may process received MR data to generate one or more MR images using any suitable image reconstruction process(es). Controller 106 may provide information about one or more pulse sequences to computing device 104 for the processing of data by the computing device. For example, controller 106 may provide information about one or more pulse sequences to computing device 104 and the computing device may perform an image reconstruction process based, at least in part, on the provided information.

Computing device 104 may be any electronic device that may process acquired MR data and generate one or more images of the subject being imaged. In some embodiments, computing device 104 may be a fixed electronic device such as a desktop computer, a server, a rack-mounted computer, a workstation, or any other suitable fixed electronic device that may be configured to process MR data and generate one or more images of the subject being imaged. Alternatively, computing device 104 may be a portable device such as a smart phone, a personal digital assistant, a laptop computer, a tablet computer, or any other portable device that may be configured to process MR data and generate one or images of the subject being imaged. In some embodiments, computing device 104 may comprise multiple computing devices of any suitable type, as aspects of the disclosure provided herein are not limited in this respect. A user 102 may interact with computing device 104 to control aspects of the low-field MR system 100 (e.g., program the system 100 to operate in accordance with a particular pulse sequence, adjust one or more parameters of the system 100, etc.) and/or view images obtained by the low-field MRI system 100.

Figure 2A:
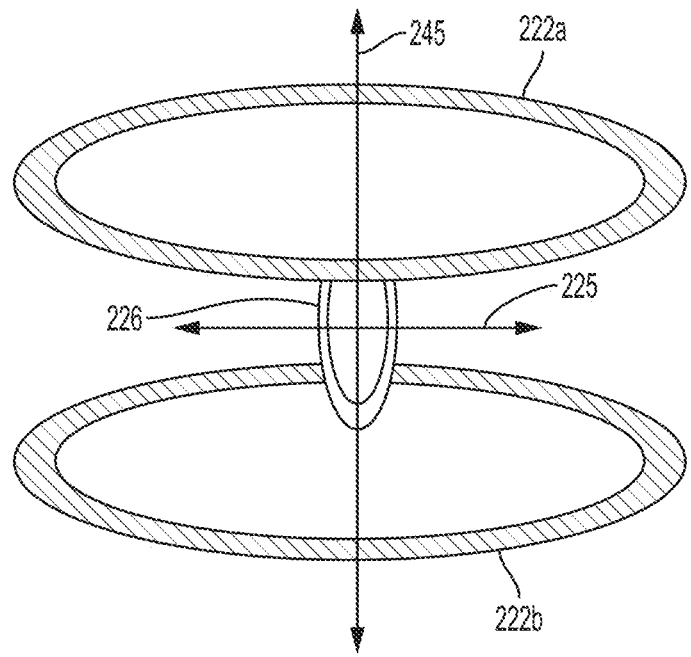
FIGS. 2A and 2B illustrate bi-planar magnet geometries, in accordance with some embodiments.
Figure 2B:
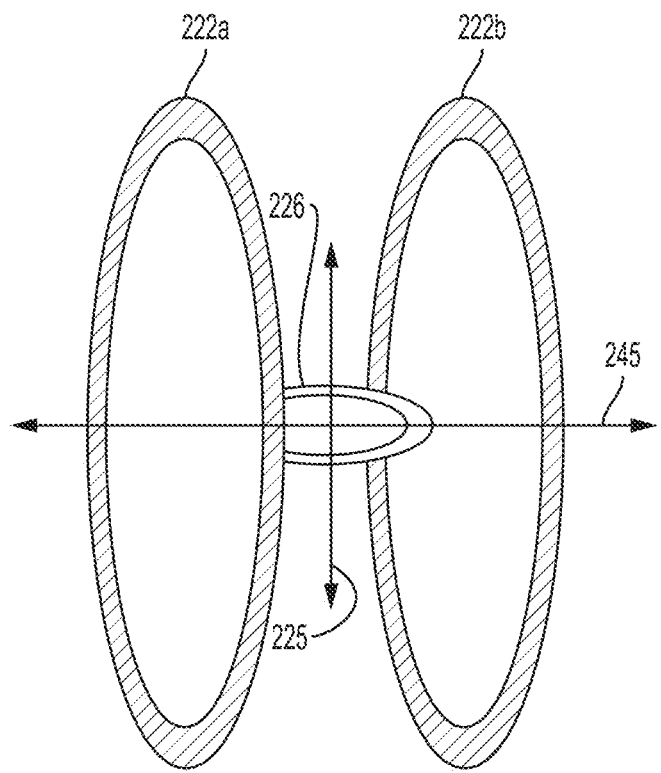

FIGS. 2A and 2B illustrate exemplary bi-planar geometries for a B0 magnet. B0 magnet 222 is schematically illustrated by magnet 222a and 222b arranged substantially parallel to one another to generate a B0 field generally along axis 245 in whichever (direction is desired to provide a field of view between the magnets 222a and 222b (i.e., a region between the magnets wherein the homogeneity of the B0 field is suitable for MRI). This bi-planar arrangement allows for the production of a generally "open" magnetic resonance imaging system. An RF coil (or multiple RF coils) is schematically illustrated as RF coil 226, which is/are arranged to generate a pulsed oscillating magnetic field generally along axis 225 (i.e., the principal axis of RF coil 226) to stimulate an MR response and to detect MR signals. Exemplary RF coil 226 is arranged to detect the MR signal component oriented substantially along the principal axis 225 (i.e., linearly polarized components of the MR signal aligned with the coil's principal axis). As discussed above, the relatively low operational frequencies of low-field MRI allow for coil designs that are not suitable for use in the high-field context. The inventors have developed RF coil designs that improve the ability of the coils to transmit RF pulse sequences and/or to detect emitted MR signals, some of which are discussed in further detail below. The inventors have further developed techniques for optimizing the arrangement of conductor(s) for an RF coil according to a desired criteria using magnetic synthesis, some examples of which are also described in further detail below.

Figure 3A:
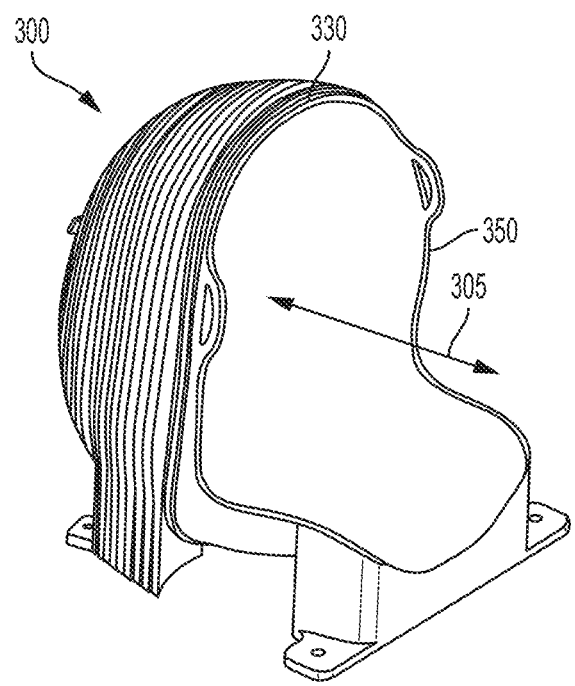
FIGS. 3A and 3B illustrate exemplary head coils, in accordance with some embodiments.
Figure 3B:
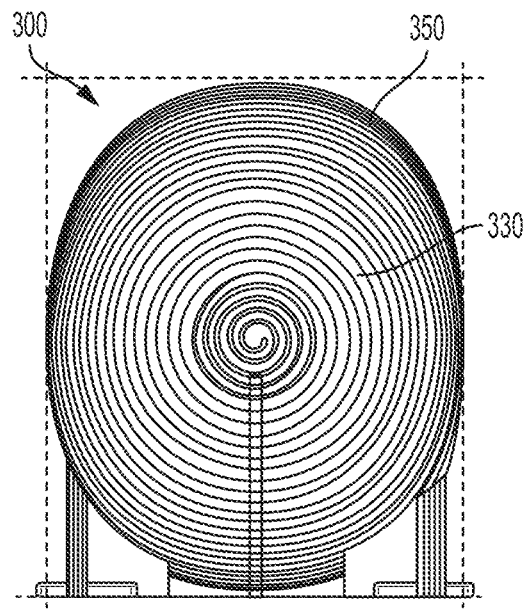

FIGS. 3A and 3B illustrate several views of a radiofrequency (RF) head coil configured to transmit appropriate RF pulse sequences in a low-field MRI system and to detect the emitted MR signals responsive to the RF pulse sequence. Transmit/receive coil 300 may, for example, correspond to RF coil 226 illustrated in FIG. 2 and configured in particular to obtain MR images of the head. As shown, transmit/receive coil 300 includes a substrate 350 formed to accommodate the head of a subject to be imaged. The substrate may be formed with grooves in which conductor 330 is provided (e.g., wound) according to a desired geometry). The substrate includes a helmet portion to accommodate the head and a support base so that a patient can comfortably rest the head within the helmet in a resting position.

As illustrated, conductor 330 is wound about substrate 350 in a spiral geometry so that, when operated, the coil produces a magnetic field in directions along axis 305, and can detect magnetic fields oriented along the same axis. As such, axis 305 corresponds to the principal axis of the coil formed by conductor 330. Conductor 330 comprises a single continuous wire forming a single channel transmit and receive coil. The exemplary transmit/receive coil 300 in FIGS. 3A and 3B has a conducting path of approximately 14 meters. As discussed above, the high frequencies of high-field MRI (e.g., greater than 64 Mhz) require conducting paths of RF coils to be very short to operate correctly (e.g., on the order of centimeters). Thus, the length of the conductor in this exemplary transmit/receive coil is well beyond (by an order of magnitude or more) the limit imposed by the high frequencies of the high-field MRI regime. However, the illustrated configuration is not optimized, and as a result, the performance of the head coil may be sub-optimal resulting in lower quality images.

The inventors have developed RF coil configurations to improve coil efficacy (e.g., improve RF pulses delivered to a subject and/or improve the sensitivity in detecting MR signals emitted in response to RF pulse sequences). As a result, increased signal can be detected resulting in higher SNR, which is a particularly important factor in low-field MRI where MR signals are relatively weak compared to high-field counterparts. The inventors have further developed techniques to determine a generally optimal arrangement (e.g., configuration) of conductors on RF coils to improve the ability of the resulting coil(s) to detect emitted MR signals in the low-field context and/or to transmit RF energy. As discussed in further detail below, the techniques described herein can be applied to any surface of interest to provide RF coils having any desired geometry for any portion or portions of the anatomy (e.g., head, torso, arms, legs, knees, etc.).

Figure 4A:
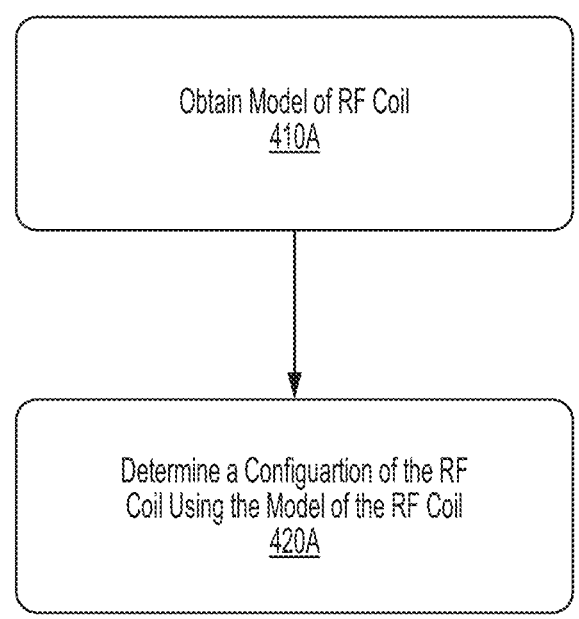
FIGS. 4A and 4B illustrate respective methods of determining a configuration of a radio frequency coil, in accordance with some embodiments.

FIG. 4A illustrates a method of determining an RF coil configuration, in accordance with some embodiments. In act 410, a model of the RF coil is provided. The term "model" refers herein to any mathematical representation of an RF coil or representation from which a representation of an RF coil can be derived. For example, a model of an RF coil may include a geometric representation such as a triangulated mesh or other representation built from geometric primitives. Additionally, the model may be described by implicit surfaces and/or may include other types of suitable mathematical representations or combinations thereof. Suitable models generally allow for magnetic field synthesis to be performed using the model, for example, by allowing the operation of the modeled RF coil to be simulated to synthesize the magnetic fields generated within a region of interest upon simulated operation. A model typically has one or more parameters that, when set to a given set of respective values, characterizes a particular configuration of the model. Varying the values of one or more of the parameters varies the configuration of the model. An optimized RF coil configuration can be derived from an optimized model configuration, for example, by finding a configuration of the model (e.g., the set of one or more parameters describing the model) that is optimal according to a given criteria, as discussed in further detail below.

In act 420A, a configuration for the RF coil is determined using the model of the RF coil. For example, an optimization may be performed using the model to determine a configuration for the RF coil that satisfies at least one constraint and that, when operation of the model is simulated, produces a magnetic field satisfying at least one criteria. According to some embodiments, the at least one criteria for the magnetic field includes magnetic field homogeneity. For example, an optimization may be formulated such that it identifies a configuration for the model that produces a magnetic field within a region of interest that meets a homogeneity criterion (e.g., non-uniformity of less than a specified percentage) when the model of the RF coil is simulated. According to some embodiments, the at least one criteria includes a magnetic field strength criterion. Any suitable criterion or combination of criteria may be used that facilitates determining a desired configuration for the RF coil from an optimized configuration of the model. According to some embodiments, the model configuration and the RF coil configuration are described using different parameters. For example, the model configuration may represent a surface potential having parameters corresponding to current densities, and the RF coil configuration represent the arrangement of a conductor (e.g., wires) in three dimensional space. According to some embodiments, an optimal model configuration may be identified (e.g., by determining an optimal set of parameters according to a given criteria) and an RF coil configuration may be determined from the optimized model configuration. Determining the RF coil configuration may involve a second optimization, but in other embodiments, the RF coil configuration is determined in other ways (e.g., determining an optimal coil configuration may involve multiple stages). According to some embodiments, the optimal RF coil configuration is determined in conjunction with optimizing the model configuration. For example, the model configuration and the RF coil configuration may be similarly parameterized such that the optimal RF coil configuration is generally determined by optimizing the model configuration, depending on how the RF coil is modeled.

As discussed above, an optimization may include finding optimal parameter values that satisfy a given criteria in view of at least one constraint. The at least one constraint may be any constraint or combination of constraints that facilitates a configuration (either a model and/or coil configuration) that meets one or more design specifications for the RF coil. According to some embodiments, the at least one constraint includes resistance of the RF coil configuration. For example, the optimization may enforce a maximum resistance for an RF coil configuration or otherwise minimize coil resistance in determining an optimal configuration with respect to a given criteria. According to some embodiments, the at least one constraint includes inductance of the RF coil. For example, the optimization may enforce a maximum inductance for an RF coil configuration or otherwise minimize coil inductance in determining an optimal configuration with respect to a given criteria. Any other constraint or combination of constraints may additionally or alternatively be used to determine a coil configuration, some examples of which are described in further detail below.

As a result of performing step 420A, a configuration of the RF coil is obtained. As discussed above, a coil configuration may be defined by a set of parameters describing the RF coil. According to some embodiments, the configuration of the RF coil describes the three dimensional geometry of one or more conductors (e.g., describes how one or more conductors are arranged in three-dimensional space). For example, the configuration may describe the number of turns or loops and the spacing between turns of at least one conductor of the RF coil and/or any other description of how the at least one conductor is arranged. The configuration may be any description of how one or more conductors of an RF coil are arranged over a surface of interest and/or any description of characteristics and/or properties of the one or more conductors, as the aspects are not limited in this respect. According to some embodiments, a coil configuration is determined from a model configuration obtained by optimizing one or more parameters of an RF coil model. For example, the RF coil configuration may include parameters that govern the number of turns of the RF coil, the spacing between turns and/or the location of the conductor (e.g., wire(s)) in the coil), etc. In general, the one or more parameters of the RF coil configuration define, at least in part, the distribution and/or arrangement of the physical conductors over the surface of interest of the physical RF coil. Further details in connection with some examples of coil optimization techniques are discussed below.

Figure 4B:
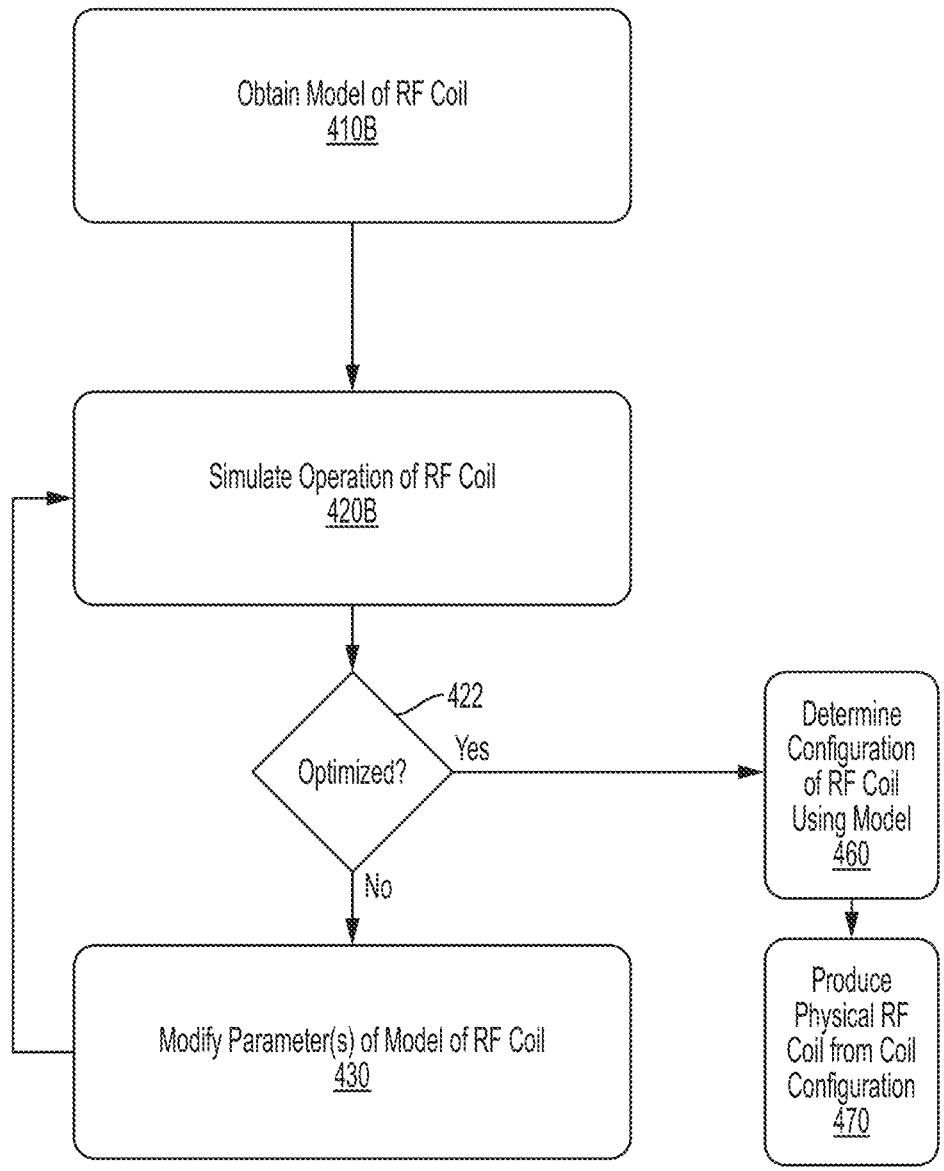

FIG. 4B illustrates a method of optimizing a configuration for an RF coil, in accordance with some embodiments. In act 410B, a model of the RF coil is obtained. The model may be obtained or provided using any of the techniques discussed above in connection with FIG. 2A, or using any suitable technique for providing a representation of the RF coil.

In act 420B, operation of the modeled RF coil is simulated for a particular configuration of the model. For example, given a particular model configuration, the magnetic fields generated by simulating operation of the model are synthesized. According to some embodiments, simulation may involve synthesizing the magnetic fields generated at a set of points within a region of interest by simulating currents on the surface of the model of the RF coil. In act 422, the synthesized magnetic fields are compared to a given criteria to evaluate whether the configuration is satisfactory from an optimization perspective (e.g., whether it satisfies a given criteria). According to some embodiments, the criteria may take the form of a function having one or more constraints and/or one or more variables to be minimized and/or maximized. For example, the optimization of the function may seek to maximize the magnetic field generated within a region of interest while minimizing the inductance and/or resistance of the RF coil (or constraining the inductance and/or resistance to be below respective prescribed values). However, any set of variables in view of any set of constraints may be used, as the techniques described herein are not limited for use with any particular optimization or optimization scheme.

The particular coil design and design constraints may dictate, at least in part, what factors are considered in optimizing the configuration of an RF coil. Non-limiting factors that may be evaluated in an optimization formulation for the design of an RF coil (e.g., in the form of variables to be minimized or maximized, or as constraints) include any one or combination of magnetic field strength, magnetic field homogeneity, coil efficiency/sensitivity, coil inductance, coil resistance, wire length, wire thickness, wire spacing, etc. The relative importance of any one or combination of these factors may be weighted so that an optimal configuration according to given design constraints may be obtained.

If it is determined in act 422 that the solution (e.g., the evaluation of a given function) resulting from simulating the operation of the model with the current configuration is optimal according to a predetermined measure, the process proceeds to act 460, where an RF coil configuration is determined based on the model configuration. For example, the optimized model configuration may be used to determine a coil configuration that, when operated, will produce a magnetic field approximately like the magnetic field simulated from the model configuration. According to some embodiments, the coil configuration is determined from the optimized model configuration by determining wire contours for an RF coil based, at least in part, on the model configuration. For example, a contouring technique, an example of which is discussed below, may be used to determine wire contours for the optimized RF coil, and the wire contours can subsequently be used to generate the actual physical RF coil as illustrated in act 470, further aspects of which are described below. That is, the contours describe a coil configuration and may be used as the pattern with which to arrange the physical conductors of the RF coil.

If it is determined in act 422 that the solution is not optimal according to the predetermined measure (e.g., does not satisfy a given criteria), the process proceeds to act 430, where one or more parameters of the model may be modified to produce an updated model configuration. In optimizing the model configuration, the process returns to act 420 to simulate the operation of the RF coil using the updated model configuration, and the process iterates until the optimum configuration is determined (e.g., the set of one or more parameters governing the model configuration are optimized according to a given criteria). The manner in which the configuration is updated for the next iteration can be chosen in accordance with any suitable optimization scheme. By repeating acts 420, 422, and 430, the configuration of the model of the RF coil may be optimized according to some measure characterized by the criteria (e.g., by optimization of a suitable function). From the final model configuration, a generally optimal RF coil configuration may be obtained. It should be appreciated that optimizing a model configuration and/or an RF coil configuration need not result in a global or absolute optimal solution, but need only converge to some sufficient measure of "optimal." As such, for a given model and formulation, there may be numerous "optimal" solutions.

Figure 5:
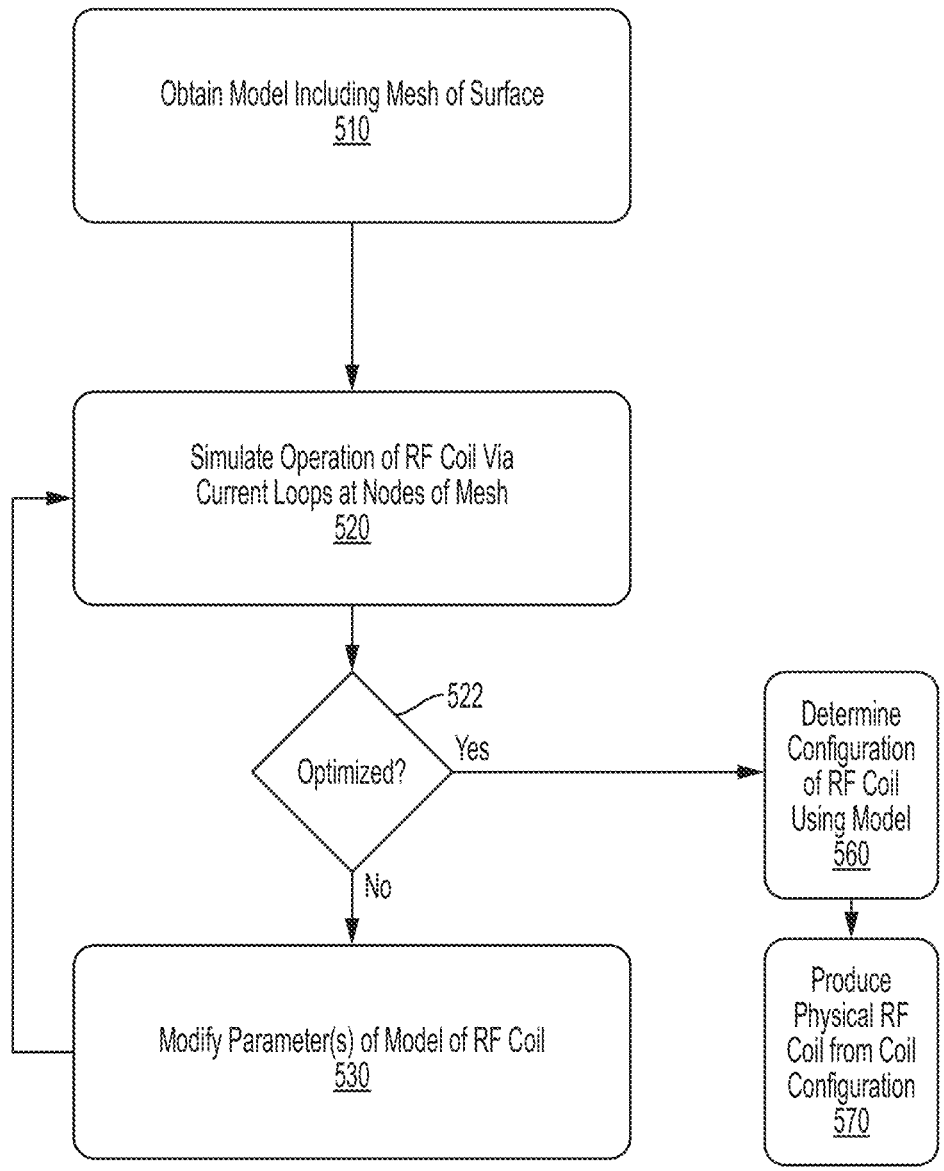
FIG. 5 illustrates a method of determining a configuration of a radio frequency coil using a model of the radio frequency coil that includes a mesh, in accordance with some embodiments.
Figure 6A:
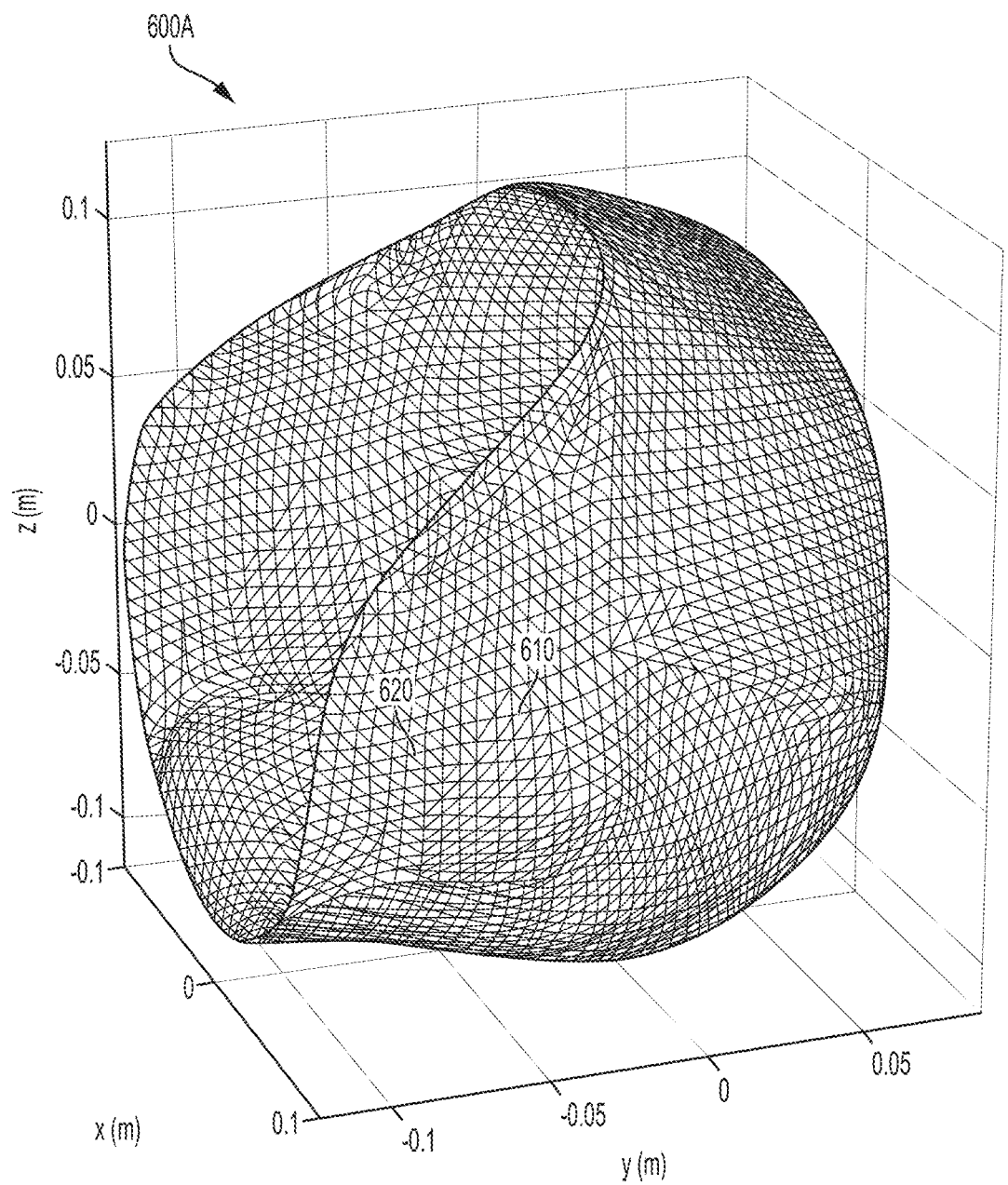
FIG. 6A illustrates an exemplary triangular mesh for use in a model of an exemplary head coil, in accordance with some embodiments.
Figure 6B:
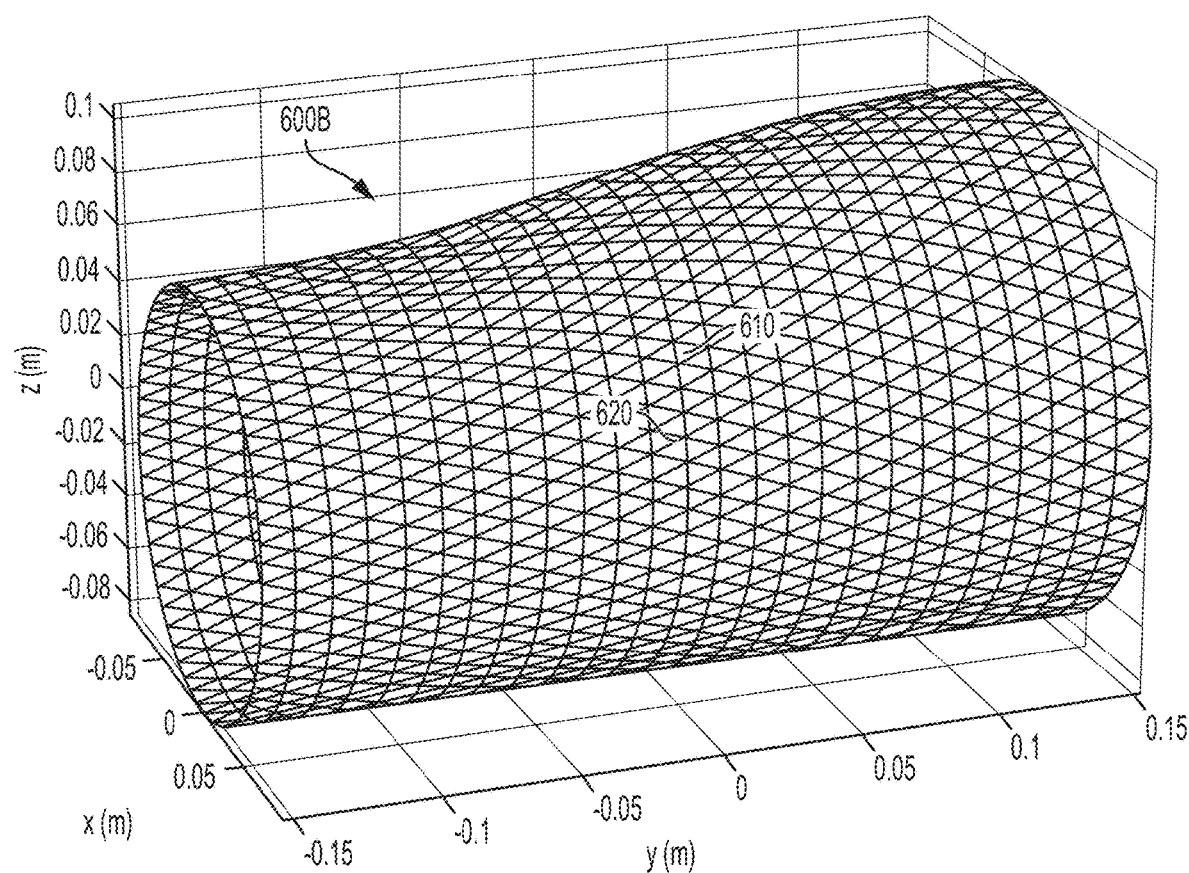
FIG. 6B illustrates an exemplary triangular mesh for use in a model of an exemplary leg coil, in accordance with some embodiments.

FIG. 5 illustrates an example implementation of the general method described in FIG. 4, in accordance with some embodiments. In act 510, a model of an RF coil is provided using a three-dimensional mesh of a surface corresponding to a region of interest to which RF energy is to be provided and MR signals are to be detected (e.g., the field of view of a low-field MRI system). According to some embodiments, the mesh comprises a plurality of surface elements connected by nodes at the vertices of the surface elements. Non-limiting examples of a meshes having triangular surface elements that may be used as a basis for a model of an RF coil in accordance with some embodiments are shown in FIGS. 6A and 6B. In particular, FIG. 6A illustrates an exemplary mesh 600A corresponding to a head coil. Mesh 600A is formed by a plurality of triangles (e.g., triangle 610) connected by sharing sides with one or more adjacent triangles. Each triangle vertex or node (e.g., node 620) is shared by one or more adjacent triangles, although any suitable configuration of surface elements may be used to form a mesh. In some embodiments, the mesh comprises approximately 1000-4000 triangles, though it should be appreciated that any suitable number of triangles may be used, and the number and/or shape of triangles in the mesh may depend, at least in part, on the surface being modeled.

FIG. 6B illustrates an exemplary mesh 600B corresponding to an RF coil adapted for imaging the leg, for example, the knee or other portion thereof. Like the mesh in FIG. 6A, the desired surface is triangulated to form a plurality of triangles (e.g., triangle 610) interconnected at shared vertices or nodes (e.g., node 620). It should be appreciated that that the exemplary surfaces illustrated in FIGS. 6A and 6B are merely illustrative and a mesh can be defined for any arbitrary geometry using any desired primitive. That is, surface elements having any geometric shape (e.g., triangles, squares, hexagons, octagons, etc.) may be used to define a mesh over any surface. It should be further appreciated that using a mesh is merely one example of a geometric representation that may be suitable for use in providing a model of an RF coil.

A mesh, such as those illustrated in FIGS. 6A and 6B, provides a flexible representation to model an RF coil, as any arbitrary surface can be represented using a mesh, thus facilitating the modeling of an RF coil for any desired portion of the anatomy of the human body, including, but not limited to the head, neck, torso, one or more appendages or portions thereof (e.g., arms, legs, hands, feet or portions thereof), and/or any combination of anatomical portions to produce an RF coil optimized for use with any desired portion of the human body.

Referring again to FIG. 5, in act 520, operation of the model of the RF coil may be simulated. For example, using the example triangular meshes 600A or 600B illustrated in FIGS. 6A and 6B, operation of the model may be simulated, at least in part, by simulating current loops about each node in the mesh (e.g., by simulating current loops through adjacent triangles around their shared nodes) and computing the magnetic field generated by the respective current loops at designated target points selected within a region of interest. Specifically, a number of target points (e.g., 100-1000 designated points on the interior of the triangular mesh) may be selected at which to compute the magnetic fields resulting from simulating current loops about the nodes of the triangular mesh. Generally speaking, the target points are selected and distributed in a manner so as to suitably characterize the magnetic fields throughout the region of interest. The region of interest may, for example, be associated with the field of view of the imaging system, but may correspond to other regions of interest as well.

According to some embodiments, current loops are simulated at each node in the mesh and the resulting magnetic field generated by each of the current loops at each target point is determined to obtain information regarding the effect of each current loop on each of the target points. For example, simulating operation of the model in this manner can be used to obtain a matrix of data corresponding to the magnetic field generated at each of the target points in response to each respective current loop that is simulated. This data can in turn be operated on by a suitable optimization algorithm, examples of which are described in further detail below. According to some embodiments, the strength of each of the current loops forms, at least in part, a set of parameters that are varied during optimization. That is, a suitable optimization algorithm selects the strength for each of the current loops to, for example, maximize or minimize a given function (e.g., a potential function defined on the surface of the mesh by the current loops) or other suitably formulated optimization to achieve desired magnetic field characteristics at each of the target points in the region of interest.

Figure 7A:
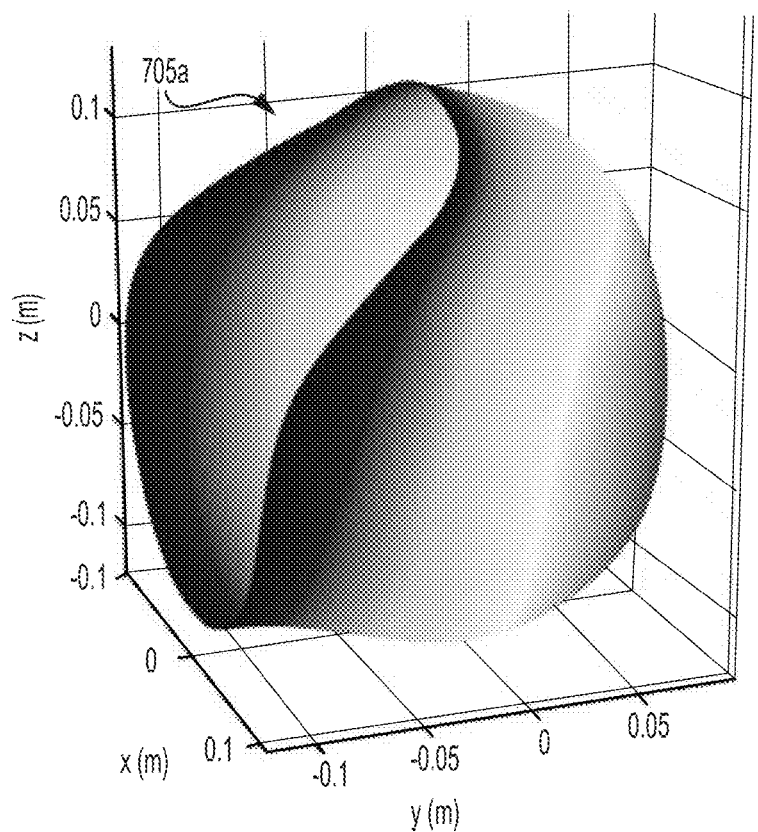
FIG. 7A illustrates an optimized model configuration for an exemplary head coil, in accordance with some embodiments.
Figure 7B:
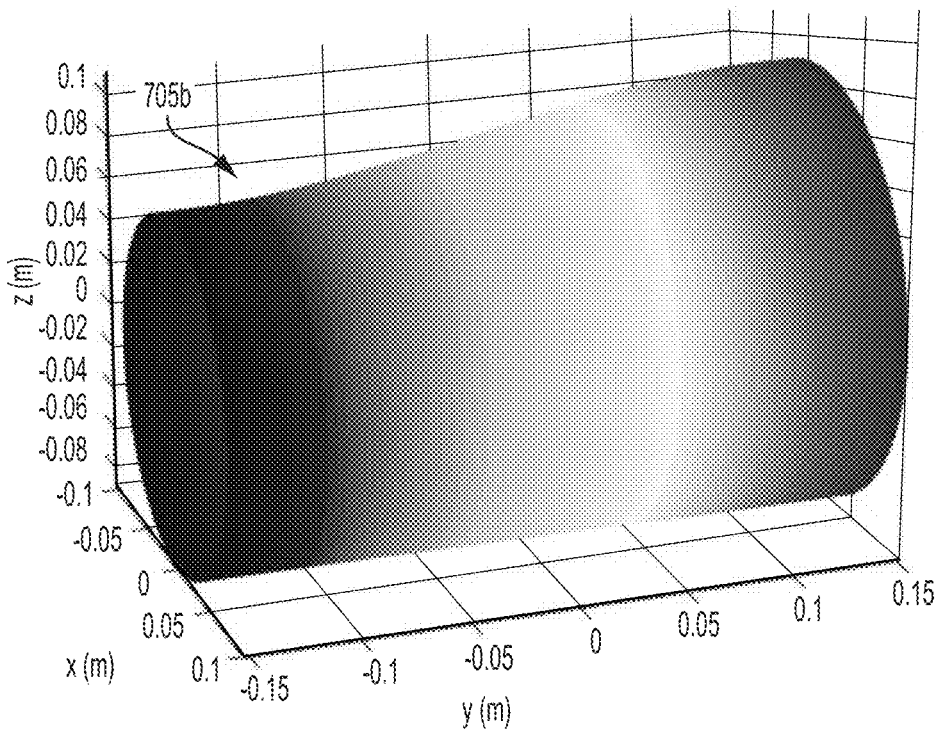
FIG. 7B illustrates an optimized model configuration for an exemplary leg coil, in accordance with some embodiments.

Following simulation of the operation of the RF coil using surface current loops, the example process of FIG. 5 proceeds in a similar manner as discussed above in connection with the example process of FIG. 4. For example, according to some embodiments, operation of the model may be performed by simulating current loops around the nodes of the surface elements (e.g., vertices of the triangular mesh) to optimize a potential function defined on the surface of the mesh. In such an example optimization, iterating through acts 520, 522 and 530 shown in FIG. 5 results in an optimized surface potential achieved, at least in part, by varying the strengths of the current loops simulated over the triangulated mesh until the magnetic field generated satisfies a given criteria. FIGS. 7A and 7B illustrate model configurations 705a and 705b, respectively. In the exemplary embodiments illustrated in FIGS. 7A and 7B, the model configuration is characterized, in part, by surface potentials that have been optimized using techniques described herein. In particular, the shading in FIGS. 7A and 7B depicts the magnetic scalar surface potential (e.g., the stream function of the current density, as discussed in further detail below in connection with the exemplary optimization illustrated in FIG. 12), the value of which are determined during the optimization. From this surface potential function, a coil configuration may be determined, as discussed in further detail below. In the exemplary embodiments illustrated in FIGS. 7A and 7B, the surface potential function corresponds to the integrated current densities over the surface, obtained, at least in part, by varying the current strength parameter of the current loops at the nodes in the mesh until simulation of the model configuration has been optimized to satisfy a given criteria in view of one or more constraints.

Figure 8A:
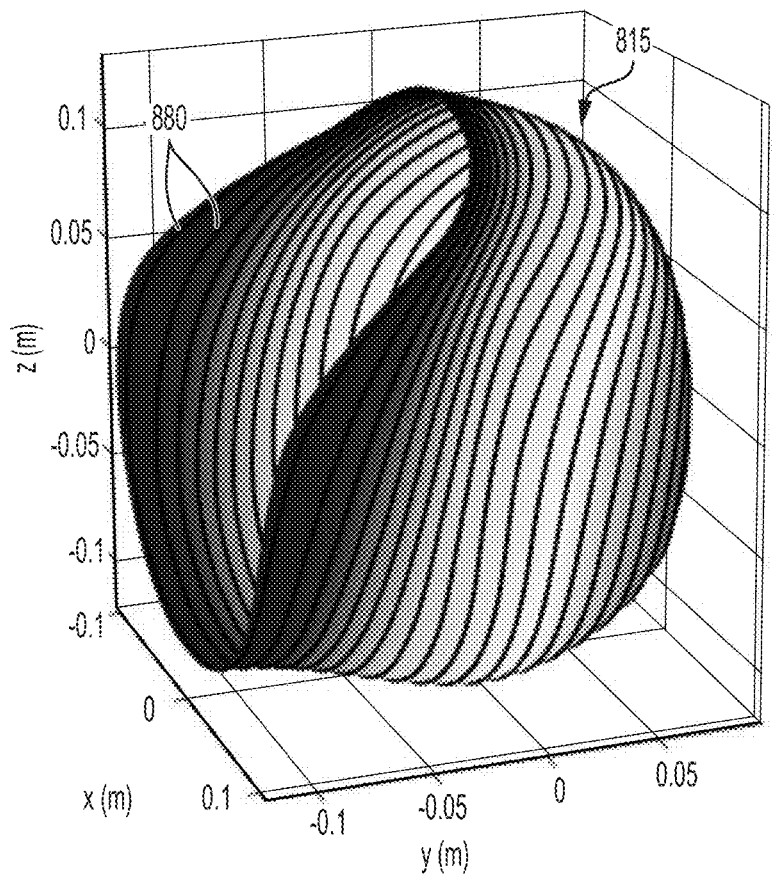
FIGS. 8A and 8B illustrate an exemplary coil configuration determined from the optimized model configuration illustrated in FIG. 7A, in accordance with some embodiments.
Figure 8B:
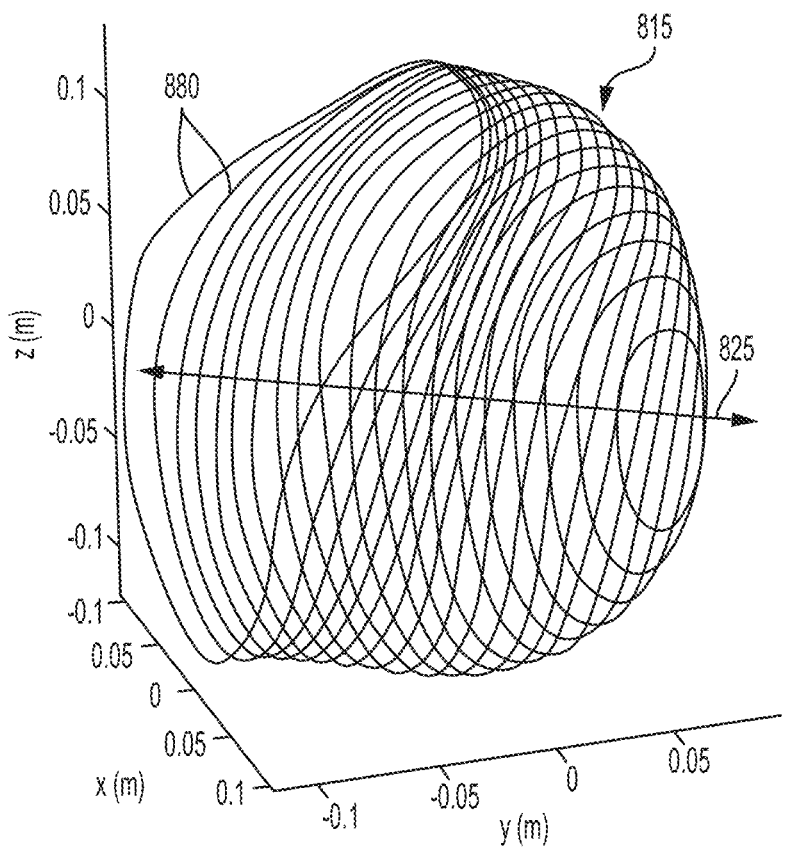

In act 560, an RF coil configuration may be determined from the model configuration. For example, the model configuration 705a and 705b (e.g., a potential function) illustrated in FIGS. 7A and 7B may be converted into contours indicating the arrangement of the conductors for an RF head coil and leg coil, respectively. FIGS. 8A and 8B illustrate a coil configuration 815 characterized by contour lines (e.g., exemplary contour lines 880) for the conductor(s) of a head coil determined from the model configuration 705a illustrated in FIG. 7A. For example, for the exemplary coil configurations illustrated in FIGS. 8A and 8B, the contour lines are selected so as to produce the current densities (i.e., the differential of the surface potential function illustrated in FIGS. 7A and 7B) of the optimized model configuration. Because the contour lines of a coil configuration represent the current paths of a coil that may ultimately be realized by a single conductor (e.g., a single conductor wound to form a plurality of turns or loops in accordance with the contours of the coil configuration), each contour line has the same current. Thus, to achieve the varying current densities described by the model configuration, the spacing of the contour lines are varied accordingly. Specifically, regions of higher current density will produce contours that are spaced closer together while regions of lower current density will produce contours that are spaced further apart. Thus, a coil configuration may be determined from a model configuration by finding contour lines of equal potential over the surface potential function of the model configuration (e.g., contour lines that pass through equal scalar values of the surface potential functions illustrated in FIGS. 7A and 7B). Determining a coil configuration from a model configuration in this manner may be achieve, at least in part, using any suitable contouring or level set algorithm.

FIG. 8A illustrates coil configuration 815 overlaid on the model configuration from which the contours were determined, and FIG. 8B illustrates coil configuration 815 by itself. The contour lines for the conductor of the RF coil are selected to produce substantially the magnetic field generated when simulating the model using the optimized model configuration. In this manner, a generally optimal coil configuration 815 may be determined. That is, the exemplary coil configuration 815, characterized by the arrangement of the contours in space, defines a conductor pattern optimized according to a desired criteria. As illustrated, the contours of the coil configuration 815 have a principal axis 825, substantially aligned with the longitudinal axis of the body. Principal axis 825 is also an exemplary reference axis about which the coil configuration forms a plurality of turns.

Figure 9A:
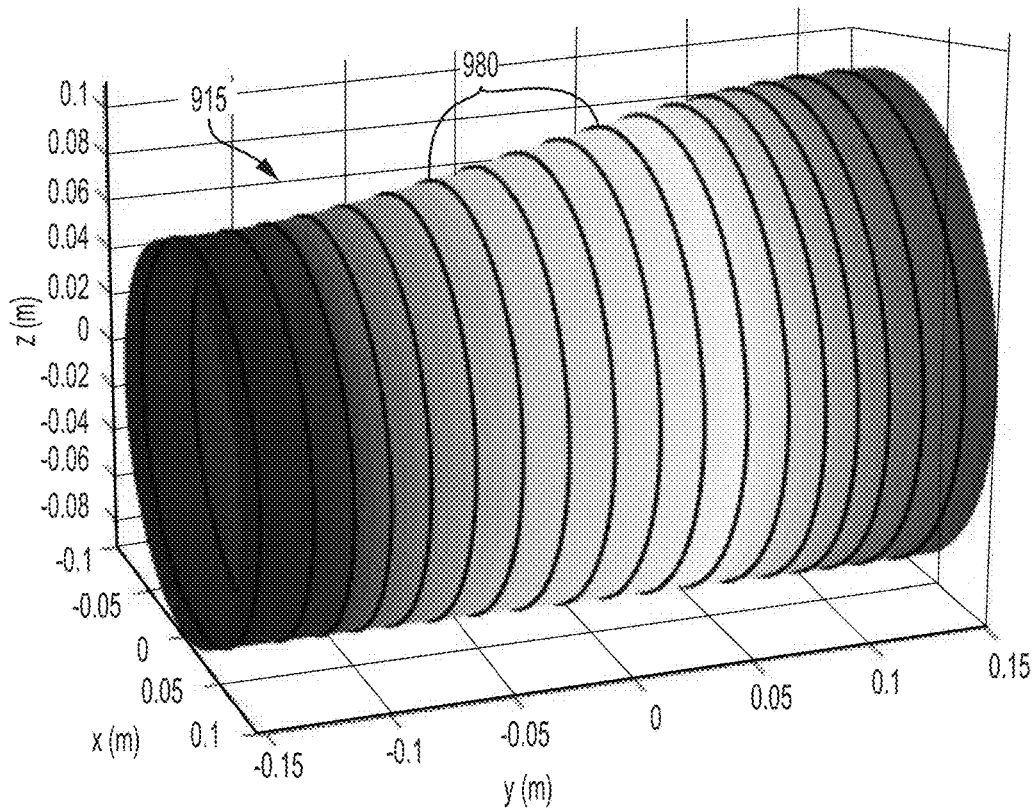
FIGS. 9A and 9B illustrate an exemplary coil configuration determined from the optimized model configuration illustrated in FIG. 7B, in accordance with some embodiments.
Figure 9B:
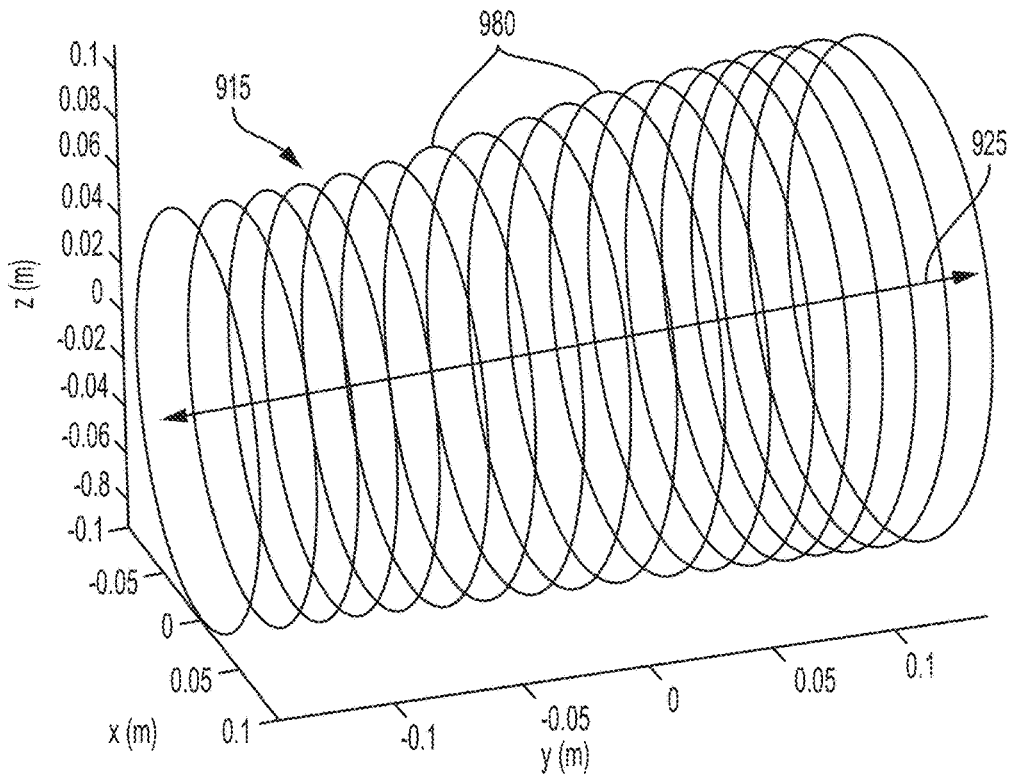

As illustrated in FIGS. 8A and 8B, in the resulting RF coil configuration, the spacing between the contours (e.g., the spacing between turns in the conductor of the RF coil are non-uniform with contours being more closely spaced towards the base of the RF coil configuration. Thus, in contrast to the coil illustrated in FIG. 3 having a configuration based on human intuition that has substantially uniform spacing between the turns of the conductor of the coil across the helmet surface, the optimized coil configuration illustrated in FIGS. 8A and 8B has non-uniform spacing between numerous contours such that the resulting RF coil will have non-uniform spacing between numerous turns or loops of the conductor forming the RF coil, a configuration that provides an optimal solution that is unlikely to be arrived at using human intuition alone or by empirical trial and error. Additionally, while the coil configuration in FIG. 3 has substantially regular contours, the optimized coil configuration results in multiple irregular contours. Thus, the optimization produces a configuration solution unlikely to be arrived at when relying on human intuition alone. FIGS. 9A and 9B illustrate an optimized RF leg coil configuration 915 determined from the model configuration 705b illustrated in 7B, the coil configuration forming a plurality of turns about a principal axis 925, which is substantially aligned with the longitudinal axis of the target anatomy (e.g., the patient's leg) when the target anatomy is positioned within the coil.

Figure 10A:
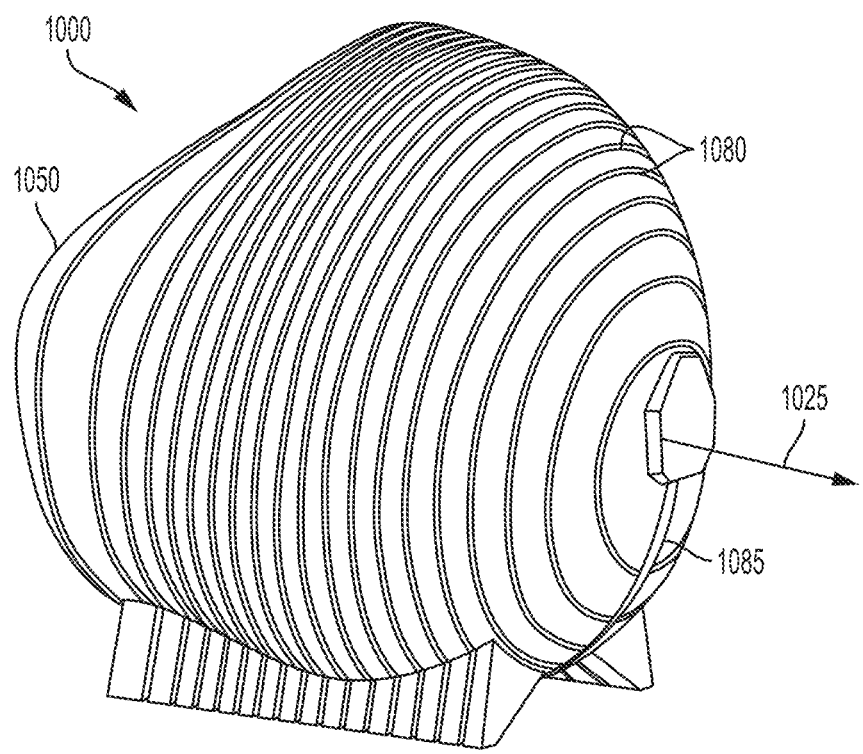
FIGS. 10A and 10B illustrate views of a support surface having grooves to accommodate a conductor in accordance with the coil configuration illustrated in FIGS. 8A and 8B.
Figure 10B:
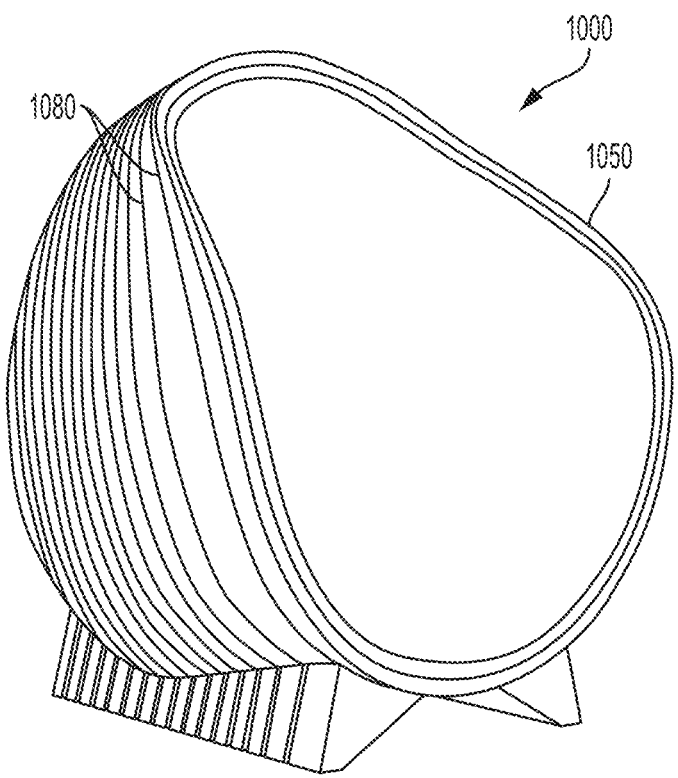

An RF coil configuration (e.g., the exemplary coil configurations illustrated in FIGS. 8A, 8B, 9A and 9B) may then be used to produce an RF coil in accordance with the determined configuration. For example, to produce an RF coil the RF coil configuration typically will need to be transferred to a support structure, for example, a helmet to be worn by a subject for the head coil configuration 815 illustrated in FIGS. 8A and 8B. According to some embodiments, an RF coil configuration is used to produce an RF coil by applying contours of the RF coil configuration to a substrate, which is in turn used to fix the arrangement of the conductor over the surface of the RF coil. FIGS. 10A and 10B illustrate different views of a geometrical rendering of a helmet 1000 with grooves (e.g., grooves 1080) formed in a substrate 1050 corresponding to the locations computed for the conductor during the exemplary optimization described in the foregoing. For example, grooves 1080 may be provided in correspondence to the contours of coil configuration 815 determined from model configuration 705a. In particular, the contours of a coil configuration may be mapped to the surface of a support structure or substrate to provide the locations at which to apply the coil conductor (e.g., locations to provide grooves for the coil conductor). The dimensions of the grooves (e.g., the width and depth of the grooves) may be chosen so as to accommodate the conductor to be used to form the radio frequency coil. This surface, once rendered (e.g., from the surface mesh and optimized coil configuration), can then be manufactured (e.g., using a 3D printer) to quickly and cost effectively produce a helmet for an RF head coil, for example, for use in low-field MRI. As illustrated in FIG. 10A, a groove 1085 is provided to connect the grooves 1080 corresponding to the contours for the conductor (e.g., corresponding to the contours of the coil configuration obtained from an optimized model configuration). Groove 1085 allows a single conductor to be wound about substrate 1150 within the provided grooves to provide a plurality of turns of the conductor, as discussed in further detail below. When a conductor is positioned within the grooves, the conductor will form a plurality of turns about principle axis 1025, as illustrated in FIG. 10A. When a patient's head is positioned within helmet 1000, the principle axis may be directed in substantial alignment with the longitudinal axis of the patient's body.

Figure 11:
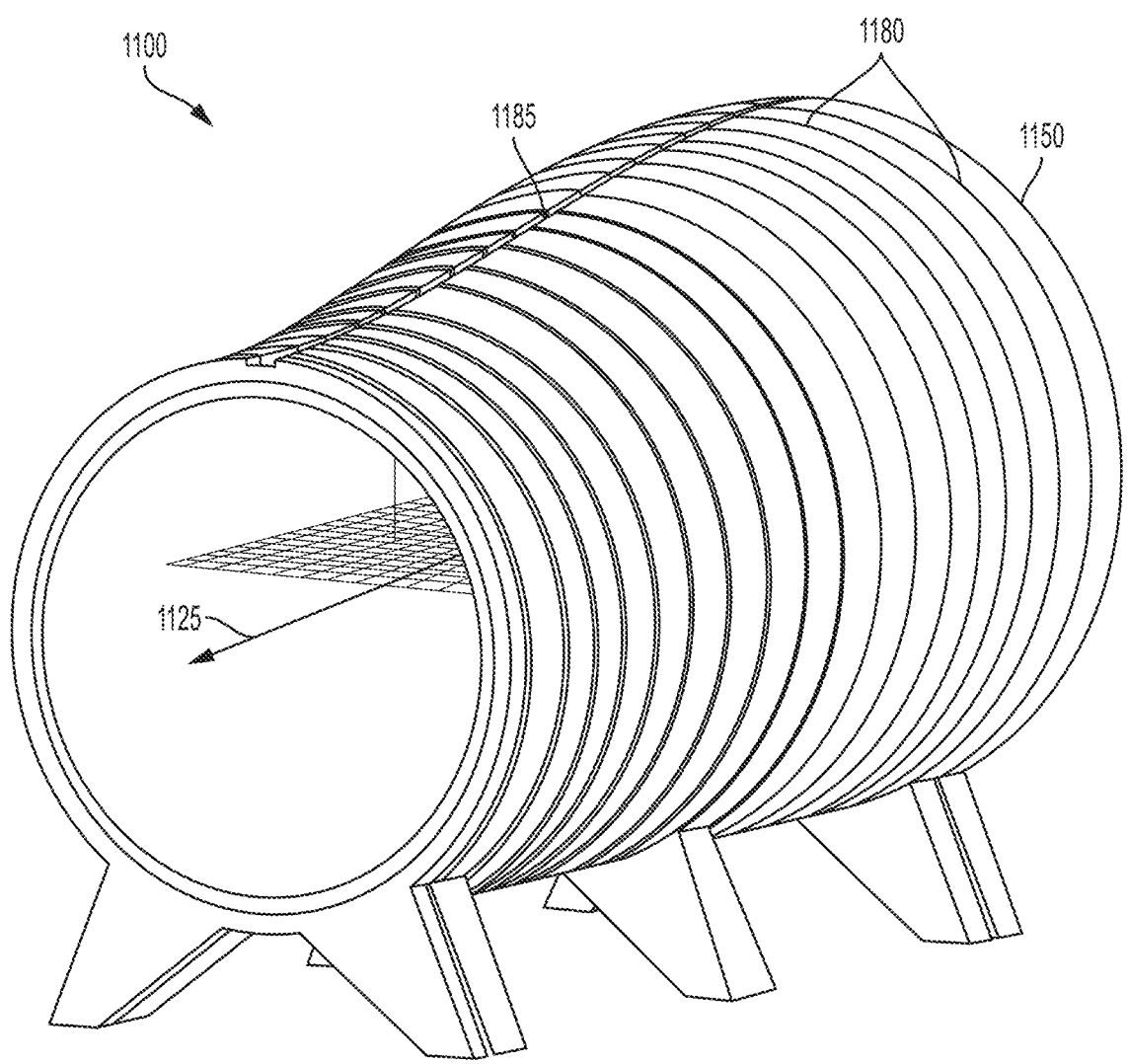
FIG. 11 illustrates a support surface having grooves to accommodate a conductor in accordance with the coil configuration illustrated in FIGS. 9A and 9B.

FIG. 11 illustrates an exemplary substrate or support 1100 to which the RF coil configuration 915 in FIGS. 9A and 9B has been applied to produce the support for a leg coil. In particular, support 1100 comprises grooves (e.g., grooves 1180), formed in substrate 1150, corresponding to the contours of the exemplary RF coil configuration 915 illustrated in FIGS. 9A and 9B. Support 1100 includes groove 1185 provided to connect grooves 1180 to facilitate positioning a conductor continuously within grooves 1180 in a plurality of turns in accordance with a desired coil configuration. When a conductor is positioned within the grooves, the conductor will form a plurality of turns about principle axis 1125.

Once a support structure is produced (e.g., helmet 1000, support 1100 or other geometry configured for particular anatomy), the conductor (e.g., wire) can be applied to the structure (e.g., by positioning the conductor within the grooves) to produce an RF coil with an optimized coil configuration. For example, a single conductor may be positioned within grooves formed in a support structure manufactured in accordance with the geometry of the respective RF coil (e.g., a wire may be placed within grooves 1080, 1180 illustrated in FIGS. 10 and 11, respectively) to produce, at least in part, an RF coil with improved transmit/receive properties. It should be appreciated that a coil configuration can be applied to a support structure using an suitable technique and is not limited to providing grooves in the substrate support structure. That is, a conductor may be coupled to a support structure according to a desired coil configuration in any suitable manner, as the aspects are not limited in this respect. An RF coil produced using an optimized coil configuration may exhibit increased sensitivity to emitted MR signals, improving the SNR of a low-field MRI system. Further examples of RF coils manufactured using techniques described herein are discussed in detail below.

The ease of which such support structures can be manufactured facilitates producing custom RF coils for particular individuals and/or particular parts of the body. In connection with customizing RF coils for particular individuals, measurements of the particular individual may be obtained using lasers or other range finding equipment and/or via manual measurements using, for example, calipers to take measurements of important dimensions of the portion of anatomy being imaged. The measurements and/or range data may be used to create a surface for use in modeling an RF coil (e.g., the measurement data may be used to render a mesh corresponding to the geometry of the anatomy of interest for the specific patient). Optimization techniques described herein may then be performed to locate an optimal RF coil configuration, which in turn can be used to produce (e.g., via 3D printing) a support for the optimal coil configuration that is customized for the particular patient. As a result, optimized coil configurations can be determined and the corresponding coil produced relatively quickly and efficiently for any arbitrary geometry of interest.

As discussed above, the design of an RF coil may involve meeting certain design constraints and/or requirements. According to some embodiments, coil inductance and/or coil resistance are evaluated to constrain the optimization of the RF coil configuration. As discussed above, to operate correctly, RF transmit/receive coils are resonated. Thus, an increase in inductance requires an increase in capacitance in the tuning circuit coupled to the coil to achieve resonance. Increased resistance impacts the quality (Q) factor of the coil by increasing the bandwidth of the coil's resonance, rendering the coil less effective in stimulating an MR effect and less sensitive in detecting emitted MR signals. A particular system may have design requirements specifying inductance and/or resistance for the coil (e.g., to achieve a coil having a specified Q factor or to match a specified tuning circuit, etc.). Thus, by evaluating coil inductance and/or coil resistance (e.g., by minimizing or setting limits on their values) an RF coil configuration can be optimized given the specified design constraints.

According to some embodiments, a regularization scheme is utilized that includes additional terms corresponding to one or more design constraints (e.g., coil resistance, coil inductance, field homogeneity, etc.). For example, coil inductance and/or coil resistance may be included as additional terms in the optimization. In connection with the example RF coil model illustrated in FIG. 6, coil resistance and/or inductance may be computed for each of the simulated current loops. As a result, data corresponding to magnetic field strength and one or more additional constraints such as coil resistance or inductance may be generated. For example, a magnetic field strength matrix may be computed as a first term and a coil resistance matrix may be computed as a second term, wherein the optimization operates to achieve desired magnetic field characteristics while minimizing coil resistance. It should be appreciated that additional terms for any desired constraint may be included in the optimization. The selected terms can be weighted as desired so that the optimization produces desired values (e.g., the values for the function on the surface of the mesh that produce an optimal result in view of the specified constraints).

It should be appreciated that any number or types of constraints may be included in the optimization to meet the requirements of a particular design. For example, a given design may require the use of a wire of given thickness or width. To prevent the optimization from selecting a configuration where wires are positioned too close together (e.g., a solution where the spacing between wires (e.g., turns of the conductor) at one or more locations on the surface is less than the width of the wire), a term may be included in the optimization that imposes a minimum spacing between wire forming the conducting path(s) of the coil. Coil resistance constraints may be implemented by including a term in the optimization corresponding to wire length for designs using wire conductors with fixed thickness, as discussed in further detail below.

An example implementation of a method for determining a configuration of an RF coil is described in further detail below in connection with the illustrative and non-limiting process illustrated in FIG. 12. It should be appreciated that the below described implementation is merely one example of how to optimize an RF coil configuration and that any other suitable techniques may be used, as determining a configuration for an RF coil using a model of the RF coil is not limited to any particular implementation. In act 1210, a surface geometry to be modeled is received. As discussed above, any arbitrary surface geometry may be used for generating an RF coil in accordance with the techniques described herein. In act 1212, a model of the surface geometry is created. In this exemplary model, the surface geometry may be considered as a thin conducting surface S, defined at a point r' by the unit normal vector to the surface; n̂(r'). The current flowing on S is represented at r' by the current density vector J (r'). When the current density is constrained to the surface S and is divergence free, a potential function, the stream-function may be defined over the surface S. The current density on the surface S generates magnetic field B(r) over a region of interest V separated from the surface S. The relationship between the generated magnetic field B(r) and the current density on the surface S may be stated as:

$$dB(r) = \frac{\mu_0 I d1 \times (r' - r)}{4\pi r^3}. \tag{1}$$

Optimization may be performed, at least on part, by solving the inverse problem to find the current density J (r') on the surface S that will provide a given magnetic field B(r) over the region of interest V. To solve this inverse problem, the problem may be discretized. For the surface S, the current density J (r') may be discretized using a mesh defined by a set of flat triangular surface elements with nodes at the corners of the surface elements (e.g., as illustrated in FIG. 6). As discussed above, shapes of surface elements other than triangles may alternatively be used to form the mesh used to discretize the surface S. A stream function ψ(r') of the current density may be discretized as a set of basis functions for each node $I_n$ of the mesh as:

$$\psi(r') \approx \sum_{n=1}^{N} I_n \psi_n(r'). \tag{2}$$

In (2), $\psi_n$ (r') is the stream-function basis-function for the nth node of the mesh. The above example stream function for a node describes a current loop flowing on the surface S through all triangle elements of the mesh that share the node. Nodes on the edge of the mesh may be forced to have the same stream function value to prevent current from flowing in and out of the edge. In the inverse solution, the stream function values at each node of the mesh act as free parameters that can be optimized using the techniques described herein.

The process then proceeds to act 1214, where the magnetic field B(r) in the region of interest V is discretized. The magnetic field may be discretized by defining a set of target points that reside within the region V. The target points may have any position in space other than on the surface S, and together define the target region of interest V. In some embodiments, described in more detail below, the set of target points may include first target points corresponding to a first region in which a maximum magnetic field is desired and second target points corresponding to a second region in which a minimum (e.g., zero) magnetic field is desired. For example, the first target points may be located in a volume inside of the surface S, whereas the second target points may be located outside of the surface S. The inclusion of the second target points enables the design of RF coils providing shielding benefits in addition to optimizing the coil design to provide a desired magnetic field in a region to be imaged, for example, the field of view of a low-field MRI system.

Figure 12:
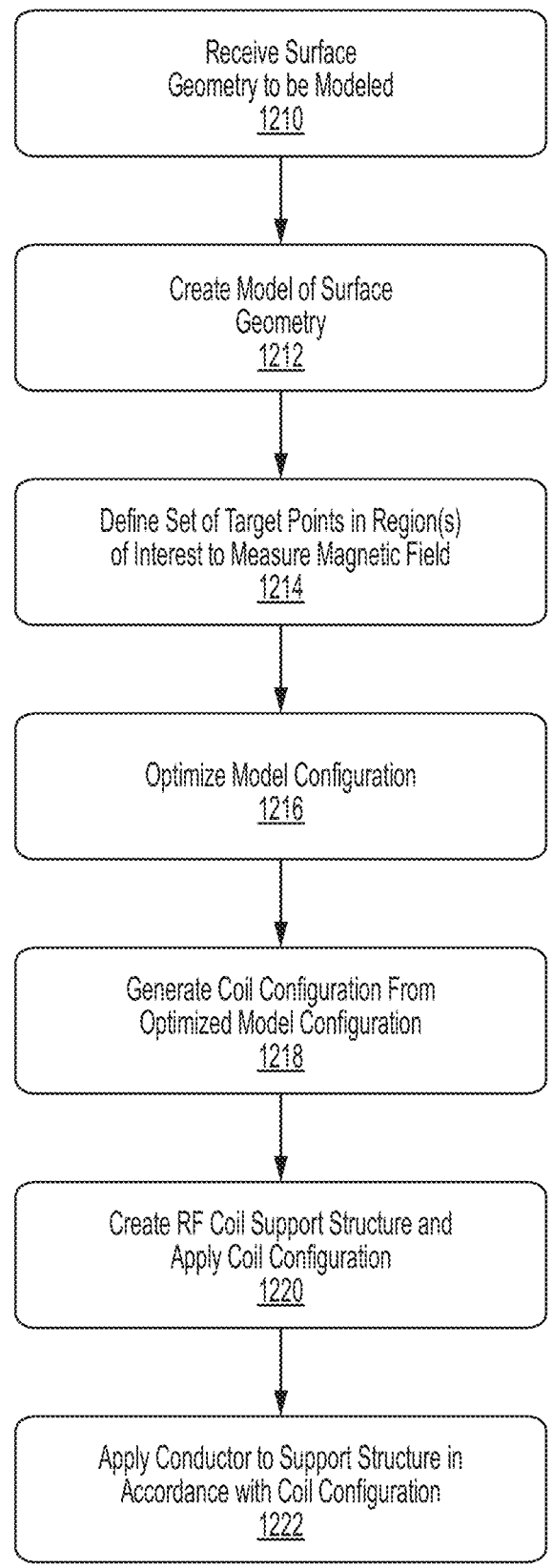
FIG. 12 illustrates a method of determining a coil configuration and applying the coil configuration to a support structure, in accordance with some embodiments.

The process of FIG. 12 then proceeds to act 1216, where the model configuration is optimized by, for example, determining the optimum values for the current density on the surface S as modeled by the stream function at each node of the mesh for the desired magnetic field at the set of target points. In addition to the desired magnetic field, some embodiments also include other parameters desired to be minimized during optimization, such as the stored energy (inductance) in the coil or resistive power dissipation in the coil. Boundary conditions may also be imposed as constraints during optimization. For example, to conserve current over the surface S, the condition that the potential be the same for all points along an edge of the surface may be imposed via one or more constraints. For example, to conserve current of the surface of the head coil illustrated in FIG. 6A, a condition that the potential be the same for points along the single edge may be enforced as a constraint in the optimization. Similarly, points along the edges on either end of the leg coil surface illustrated in FIG. 6B may also be constrained to have equal potential to other points along the same edge, though the potentials along the two edges are allowed to be different. It should be appreciated that a surface may be formed from any number of separate surface, each of which may have any number of edges. An exemplary function U to be minimized using a suitable optimization scheme may be expressed as follows:

$$U = \frac{1}{2}\sum_{k=1}^{K}(B(r_k) - B^t(r_k))^2 + \frac{\alpha}{2}\sum_{n=1}^{N}\sum_{m=1}^{N}I_nI_mL_{mn} + \frac{\beta}{2}\sum_{n=1}^{N}\sum_{m=1}^{N}I_nI_mR_{mn}. \quad (3)$$

In (3), the first term describes the difference between the measured field and the target field, the second term models the inductance $L_{min}$, and the third term models the coil resistance $R_{min}$. The inductance and resistance terms can be weighted using regularization terms $\alpha$ and $\beta$ determined based on desired features of the RF coil being designed. In some embodiments, the minimum of the function U may be identified by differentiating the function with respect to $I_n$ to produce a linear system of equations that can be consolidated into a matrix equation: ZI=b, where the matrix Z is calculated by the differentiating optimization and the vector b contains the magnetic field values. This matrix equation may then be inverted to solve for I, which contains the stream function values $I_n$ at each of the nodes n of the mesh. The nodal stream function values $I_n$ can then be linearly combined to reconstruct the stream function of the current density over the surface S. Thus, the above described optimization of a surface potential function may be used to determine an optimized model configuration, for example, the optimized model configurations 705a and 705b illustrated in FIGS. 7A and 7B, respectively. However, it should be appreciated that the above described method is merely exemplary, and any function and constraints may be optimized to obtain an optimized model configuration and will depend on the nature and characteristics of the model and the requirements of the design.

According to some embodiments, additional constraints may be added to the optimization problem including, but not limited to, requiring a minimum spacing of wires (e.g., between adjacent turns of the conductor(s)) and/or reducing the total length of the coil conductor (e.g., wire length). As another example, in the context of multi-channel receive coils (e.g., for performing parallel MRI), a further constraint that minimizes the mutual inductance between a given coil and another coil may be included in the optimization scheme (e.g., a constraint that requires or seeks to reduce the mutual inductance between pairs of coils to zero or satisfactorily close to zero). Such a constraint facilitates the design of multiple receive coil arrays that are substantially decoupled from each other during receive operations.

Introduction of additional constraints into the optimization may complicate or compromise the ability to solve the matrix equation above using a simple inversion technique. Accordingly, some embodiments minimize the function U using a convex optimization technique rather than matrix inversion. For example, optimization of the coil design may be achieved by using Tikhonov regularized minimization of the root-mean-squared (RMS) residual to minimize $\|B_\psi - b_t\|_2 + \alpha\|\psi\|_2$, where $b_t$ is the target field and a is a regularization parameter. In embodiments using a convex optimization, any suitable convex optimization solver may be used, as the aspects are not limited in this respect. It should be appreciated that other optimization techniques may also be suitable, including, but not limited to, gradient descent, genetic algorithms, particle swarm, simulated annealing, Monte Carlo techniques, etc.

Returning to the process of FIG. 12, after an optimum solution for the model configuration has been determined, the process may proceed to act 1218, where the stream function for the current density output from act 1216 is used to generate a coil configuration, for example, a representation of conductor contours that, when supplied with a current, produce the desired magnetic fields for the optimized coil design. In some embodiments, a contouring technique is used to determine the position of conductor(s) (e.g., wire(s)) on the surface S for the optimized coil configuration. Contouring may be performed in any suitable way. For example, each element (e.g., a triangle) of the mesh used to approximate the surface S may be transformed into parametric (u, v) space by linear transformation. The values of the stream-function at the corners of the element (e.g., for a triangle element ($\psi_1$, $\psi_2$, $\psi_3$)) may be used to define a plane of the stream-function in the element in (u,v, $\psi$) space. The intersection of this plane with planes of constant $\psi$, representing the contour levels $\psi C_n$, gives the equation of the conductor paths in that element. The portion of these lines that are within the u and v limit of the unit element are the wire paths of that element. The process may be carried out for all elements and transformed back into (x,y,z) space, with the result being the conductor paths of the coil configuration. In some embodiments, constraints are added during contouring to constrain the solution based on one or more physical properties, such as the width dimension of the conductor (e.g., the cross-sectional diameter of the wire), as discussed above.

Once the conductor paths for the RF coil are known, the process of FIG. 12 proceeds to act 1220, where a support structure for the RF coil is generated and the coil configuration applied to the support structure. In some embodiments, a three-dimensional (3D) printer or other suitable device may be used to generate the support structure for optimized RF coil designs, as discussed above. The support structure may include one or more channels, grooves or conduits corresponding to the location of the conductor paths resulting from determining the configuration of the RF coil (e.g., the conductor paths resulting from contouring the optimized stream function values discussed above). That is, the coil configuration may be used to determine the location of grooves configured to accommodate the coil conductor in accordance with the coil configuration. The support structure may be provided in other ways to facilitate applying one or more conductors according to the RF coil configuration determined via optimization. The process then proceeds to act 1222, where conductor(s) (e.g., a wire) is/are provided along the paths on the support structure to create an RF coil based on the optimized configuration. An appropriate resonant circuit may then be coupled to the coil to produce an RF coil optimally configured for performing transmit and/or receive, for example, as part of a low-field MRI system. In particular, the coil may be tuned to resonate at a target frequency in the low-field regime.

As discussed above, in the low-field context, the relatively low transmit frequencies allow the length of the conductors to be substantially increased with respect to the conductor lengths in the high-field regime. For example, the conductor path illustrated in the exemplary RF coil configuration applied to the support structure illustrated in FIGS. 10A and 10B is approximately 4 meters in length, which exceeds the maximum length restrictions in the high-field context by an order of magnitude or more. According to some embodiments, the conductor length is greater than 1 meter, greater than 2 meters, greater than 4 meters, greater than 7 meters, greater than 10 meters, etc. Accordingly, transmit/receive coils that operate optimally according to desired criteria may be designed and produced relatively simply and cost effectively and may operate with relatively high efficiency.

In addition to the flexibility of design afforded by increased conductor length, the substantial relaxation of this constraint allows the RF coil to be formed using a single conductor, wound in multiple turns, using single strand wire of suitable gauge or multi-stranded wire such as a Litz wire. For example, the configuration illustrated in FIGS. 10A and 10B comprises 20 turns or loops for the conductor. However, any number of turns can be selected or determined via an optimization and may depend on the geometry of the coil and desired operating characteristics thereof. Generally speaking, increasing the number of turns or loops of the coil conductor increases the sensitivity of the coil. However, the inventors have recognized that at a certain point, increasing the number of turns may in fact degrade performance of the RF coil. In particular, a coil comprising multiple turns or loops will resonate without being tuned (self-resonate) at least partially due to a parasitic capacitance arising from the relationship of the conductor between the multiple turns or loops in the coil. The effect of the self-resonance is to reduce the Q-factor of the coil and degrading its performance. This effect may be particularly deleterious when the self-resonance approaches the frequency at which the RF coil is tuned to resonate (i.e., the target resonant frequency of the coil corresponding to the strength of the B0 field of the MRI system). Because the frequency of the self-resonance decreases as the number of turns increases, this phenomena may place an effective limit on the number of turns of the conductor before the coil performance degrades unsatisfactorily. According to some embodiments, the number of turns of the conductor of the coil is limited to ensure that the frequency of the self-resonance is at least twice that of the frequency of the target resonance to which the RF coil is tuned. According to some embodiments, the number of turns of the conductor of the coil is limited to ensure that the frequency of the self-resonance is at least three times that of the frequency of the target resonance to which the RF coil is tuned, and according to other embodiments, the number of turns of the conductor of the coil is limited to ensure that the frequency of the self-resonance is at least five times that of the target resonance.

The limit on the number of turns needed to ensure that the frequency of the self-resonance is a desired distance away from the frequency of the target resonance depends on a number of factors, including the geometry and size of the coil (e.g., the geometry of a head coil may result in a different limit than the geometry of a leg coil to achieve the same separation of the self-resonance and target resonance frequencies), and the type of conductor being used (e.g., the gauge of the wire, whether the wire is single or multi-stranded, etc.). It should be appreciated that the limitation on the number of turns can be selected to any number depending on the requirements of the coil, including placing no limitation on the number of turns of the conductor of the coil.

Figure 13A:
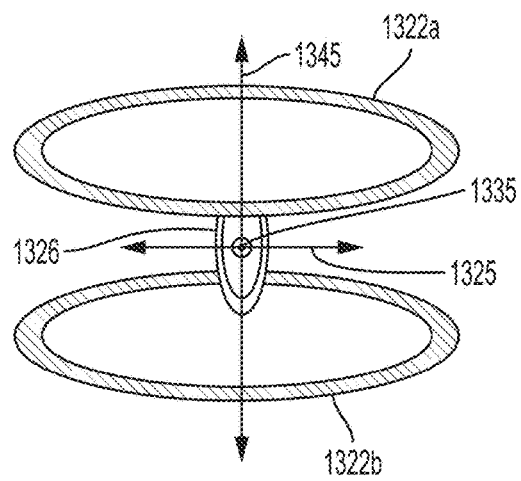
FIG. 13A illustrates a B0 magnet arranged in a bi-planar geometry.
Figure 13B:
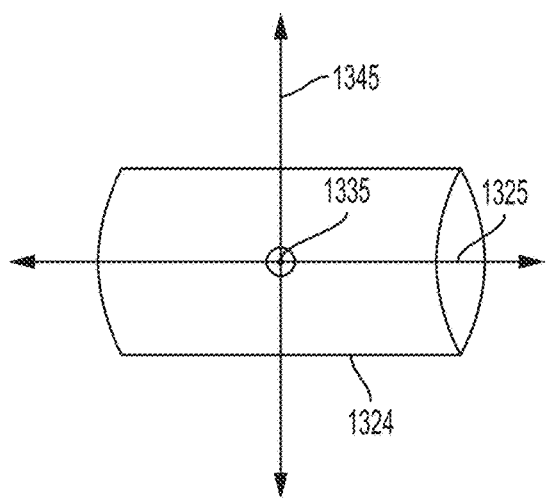
FIG. 13B illustrates a B0 magnet arranged in a cylindrical geometry.
Figure 13C:
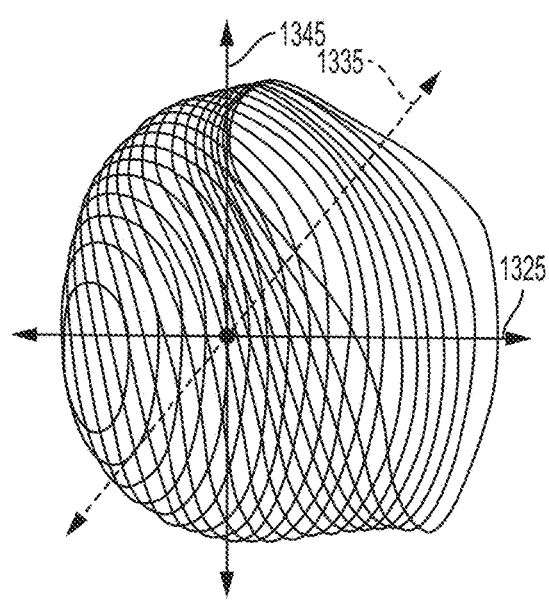
FIG. 13C illustrates a coil configuration for a head coil depicted with a set of orthogonal axes.
Figure 13D:
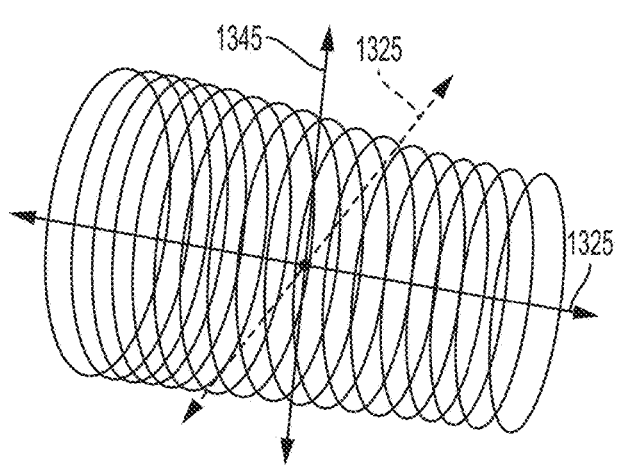
FIG. 13D illustrates a coil configuration for a leg coil depicted with a set of orthogonal axes.

The inventors have developed transmit/receive coil configurations that improve the efficacy of the coil in transmitting RF pulses and/or detecting MR signals emitted in response. As discussed above, the exemplary coils described in the foregoing are configured to detect the linearly polarized components of MR signals oriented along the principal axis of the coil (e.g., axis 1325 illustrated in FIG. 13A). However, the circularly polarized MR signals emitted, for example, in the configuration illustrated in FIG. 13A, also include linearly polarized components oriented in an orthogonal direction illustrated by axis 1335 (into and out of the plane of the drawing) that are not detected by the exemplary coils discussed in the foregoing. For example, as illustrated in FIGS. 13C and 13D, the exemplary head coil and the exemplary leg/knee coil configurations described in the foregoing are configured to detect MR signal components oriented along axis 1325, but not MR signal components oriented along axis 1335. FIG. 13B illustrates a B0 magnet 1324 having a cylindrical geometry oriented in the same coordinate frame as the planar B0 magnet illustrated in FIG. 13A. For example, B0 magnet may be a solenoid electromagnet that produces a B0 field along axis 1325. As such, exemplary coil configurations illustrated in FIGS. 13C and 13D are generally not useable in such a configuration because the principal axes of the coil configurations are aligned with the B0 field. The inventors have appreciated that RF coils can be configured to detect MR signal components oriented along axis 1335 and/or axis 1345 and such configurations can, but need not, be optimized using the same techniques described in the foregoing. As such, RF coils can be configured to detect MR signals using any B0 magnet geometry (e.g., planar, cylindrical, solenoid, etc.) by configuring the RF coil to have a principal axis oriented appropriately relative to the direction of the B0 field.

Figure 14A:
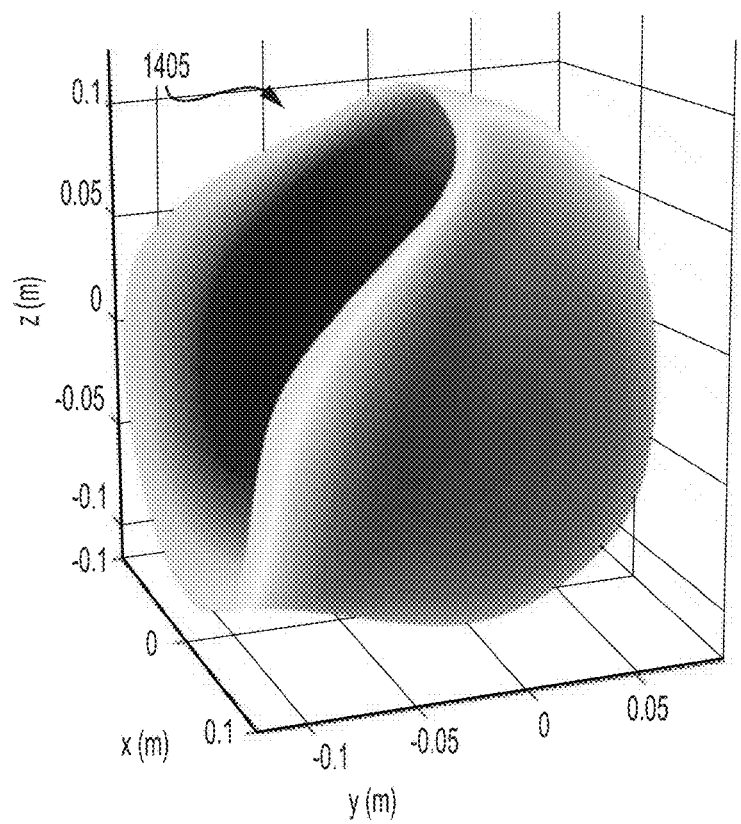
FIGS. 14A and 14B illustrate a model configuration and a coil configuration determined therefrom, respectively, for a head coil, in accordance with some embodiments.
Figure 14B:
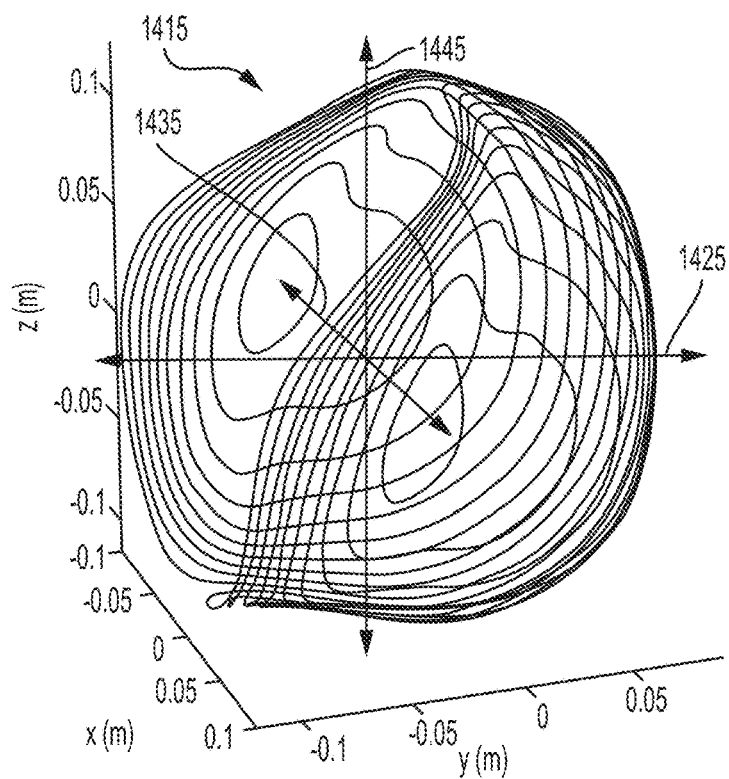
Figure 15A:
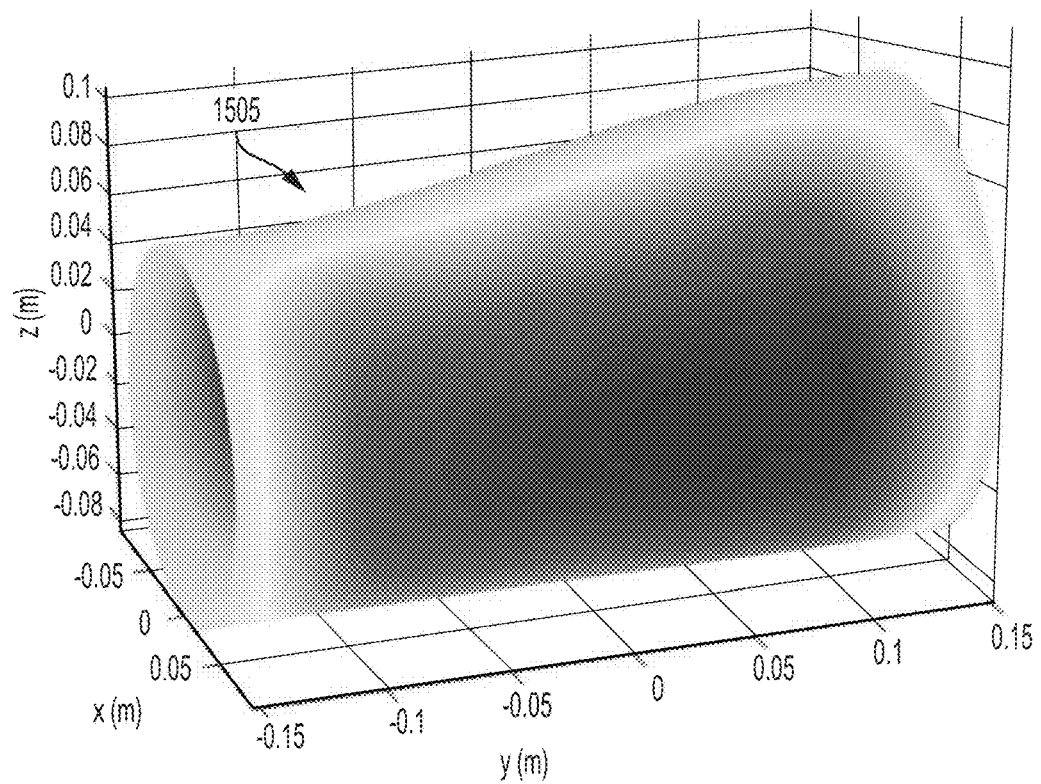
FIGS. 15A and 15B illustrate a model configuration and a coil configuration determined therefrom, respectively, for a leg coil, in accordance with some embodiments.
Figure 15B:
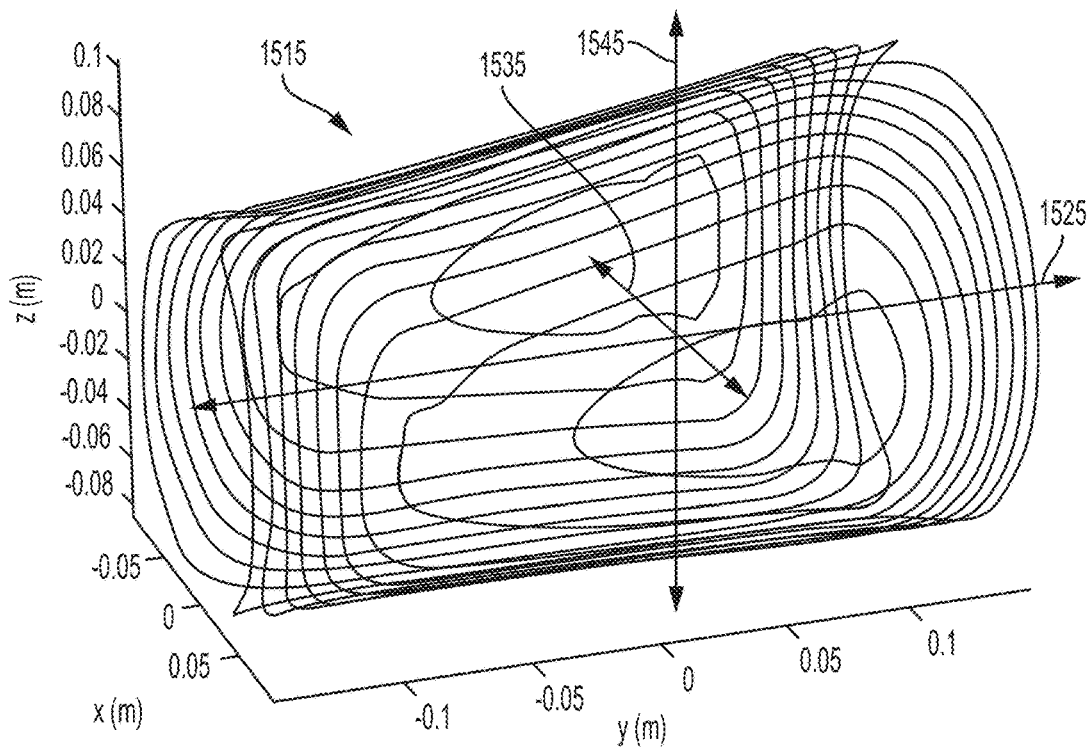

By way of illustration, FIGS. 14A and 14B illustrate an exemplary model configuration 1405 and RF coil configuration 1415 determined therefrom adapted (e.g., optimized) to detect MR signal components oriented along the principal axis 1435 of a head coil, and FIGS. 15A and 15B illustrate an exemplary model configuration 1505 and RF coil configuration 1515 determined therefrom adapted (e.g., optimized) to detect MR signal components along the principal axis 1535 of a leg/knee coil. The principal axes 1435 and 1535 also correspond to an exemplary reference axis (it should be appreciated that there are multiple reference axes) about which the respective configuration form a plurality of turns. As shown, the principle axes 1435 and 1535 are substantially orthogonal to the longitudinal axis of the target anatomy when the target anatomy is positioned within the respective coils.

Figure 16A:
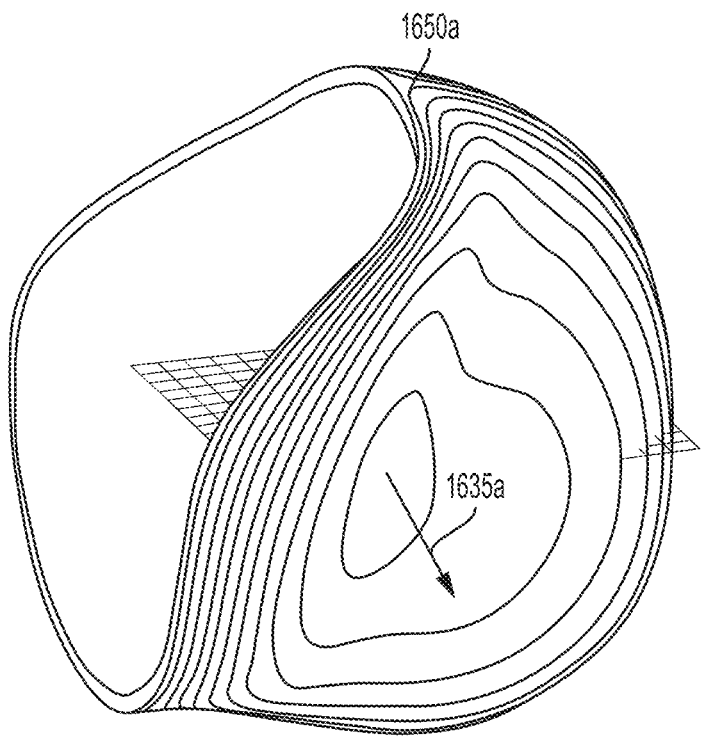
FIGS. 16A and 16B illustrate coil configurations applied to a substrate for a head coil and a leg coil, respectively, in accordance with some embodiments.
Figure 16B:
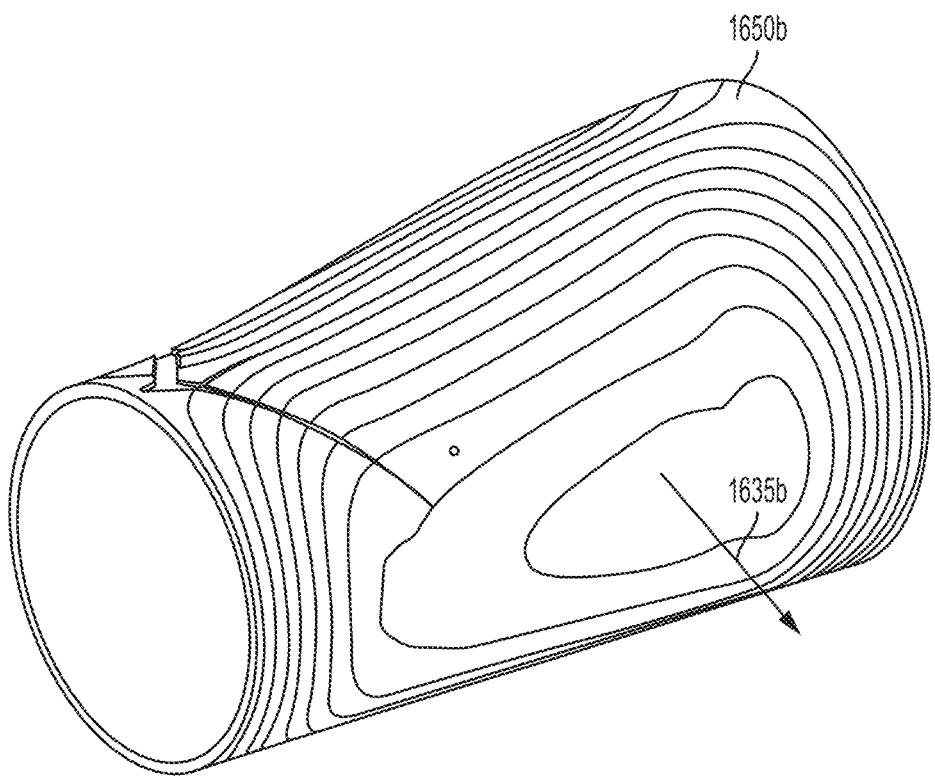

As illustrated in FIGS. 14B and 15B, the principal axes 1435 and 1535 are orthogonal to axes 1445 and 1545, respectively, along which a B0 field may be oriented, for example, a B0 field generated by a bi-planar B0 magnet. As also illustrated in FIGS. 14B and 15B, the principal axes 1435 and 1535 are orthogonal to axes 1425 and 1525, respectively, along which a B0 field may be oriented, for example, a B0 field generated by a solenoid B0 magnet. Thus, the coil configurations 1415 and 1515 may be used to produce coils to transmit RF pulses and/or detect MR signals in a number of B0 magnet geometries. In a similar or same manner as discussed above, the exemplary RF coil configurations 1415 and 1515 may then be applied to a support substrate by producing grooves or other structures to accommodate conductors of the coil (e.g., exemplary head coil substrate 1650a and leg coil substrate 1650b illustrated in FIGS. 16A and 16B, respectively) in accordance with the respective coil configuration and positioning a conductor (e.g., a wire) within the grooves or otherwise affixing the conductor to the substrate in the arrangement described by the coil configuration (e.g., the contours of the exemplary coil configurations 1415 and 1515, respectively), thus forming a plurality of turns about exemplary reference axis 1635a and 1635b, corresponding also to the principle axes of the respective coils.

Figure 17:
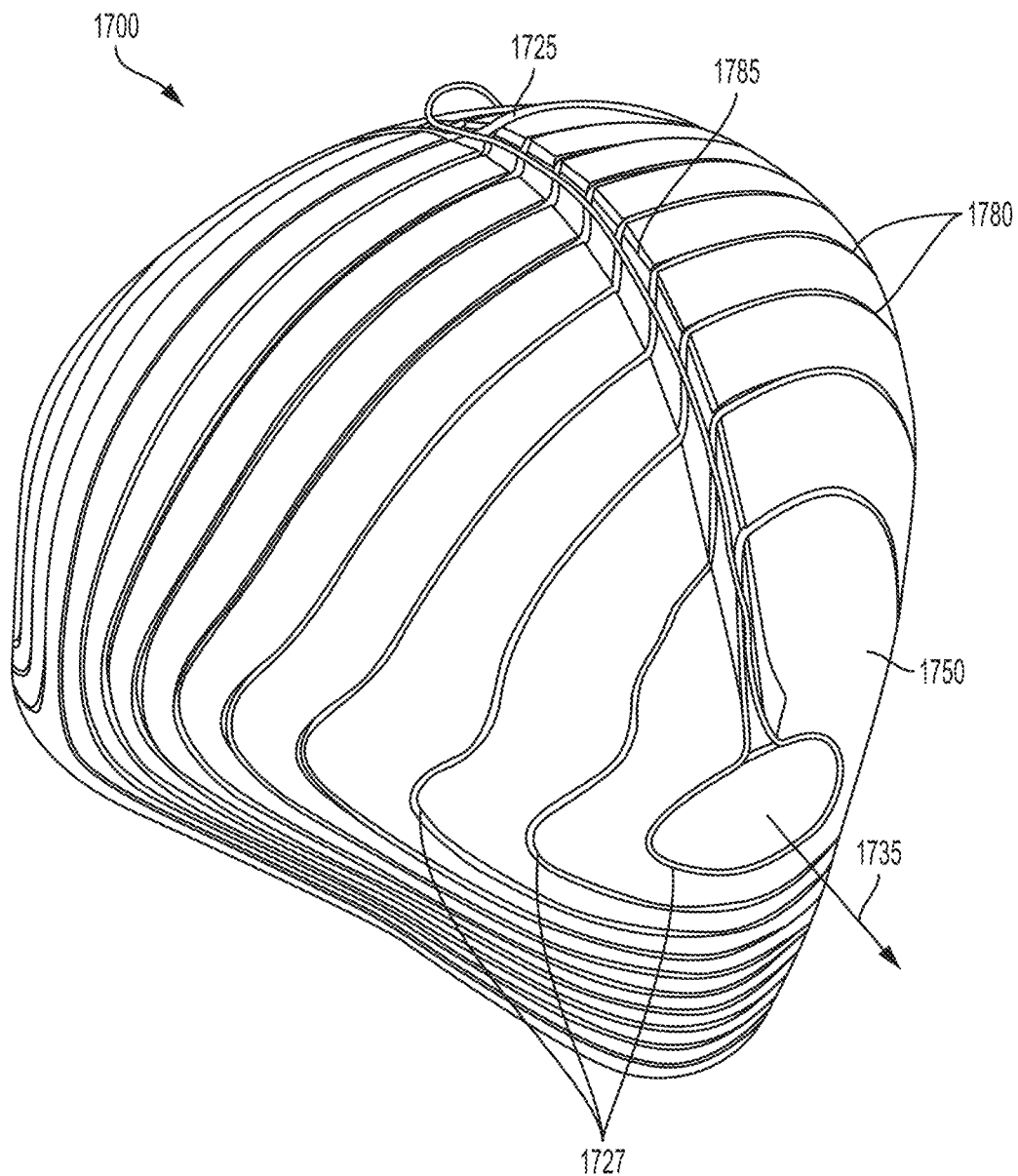
FIG. 17 illustrates a conductor applied to a substrate in accordance with a coil configuration, in accordance with some embodiments.

FIG. 17 illustrates an exemplary head coil in which a conductor is positioned within grooves formed in a support substrate in the form of a helmet configured to accommodate a person's head to, for example, obtained one or more images of the patient's brain. In particular, head coil 1700 includes a substrate 1750 having grooves or channels 1780 arranged according to a desired coil configuration in which a conductor 1725 is placed to form a plurality of turns or loops (e.g., illustrative turns 1727) of the coil. Groove 1785 is provided to connect grooves 1780 so that conductor 1725 can be wound about the support substrate from one contour or loop to the next in accordance with a desired coil configuration. Exemplary head coil 1700 comprises 20 turns (10 turns on each hemisphere) formed by the conductor loops of the coil configuration about principal and exemplary reference axis 1735. As discussed above, the relatively long conductor lengths that can be used in the low field context allow a single conductor to be wound about the surface of interest in accordance with a desired coil configuration. It should be appreciated that according to some embodiments, a coil configuration is applied using a plurality of conductors, which may be independent of one another or connected together. According to some embodiments, conductor 1725 is formed from a suitable gauge wire. For example, conductor 1725 may be a single stranded wire or may be a multi-stranded wire such as a Litz wire. It should be appreciated that conductor 1725 may be any suitable conductor, as the aspects are not limited for use with any particular type of conductor.

As discussed in the foregoing, the inventors have recognized that multiple coil configurations can be used in conjunction to improve the SNR of an RF coil. For example, a pair of coils configured to have different principal axes may be used to obtain dual measurements of MR signals. According to some embodiments, an RF transmit/receive component is provided comprising a first coil and a second coil configured to have respectively orthogonal or substantially orthogonal principal axes to improve the SNR of the RF component. For example, the exemplary head coil configurations adapted to detect MR signal components oriented along the principal axis 1325 of the exemplary coil configuration illustrated in FIG. 13B) and the exemplary head coil configurations adapted to detect MR signal components oriented along the principal axis 1435 of the exemplary coil configuration illustrated in FIG. 14B), respectively, can be used together to detect MR signal components oriented along both principal axes. By utilizing such a dual coil arrangement, the SNR of MR signal detection may be improved, as discussed in further detail below.

Figure 18A:
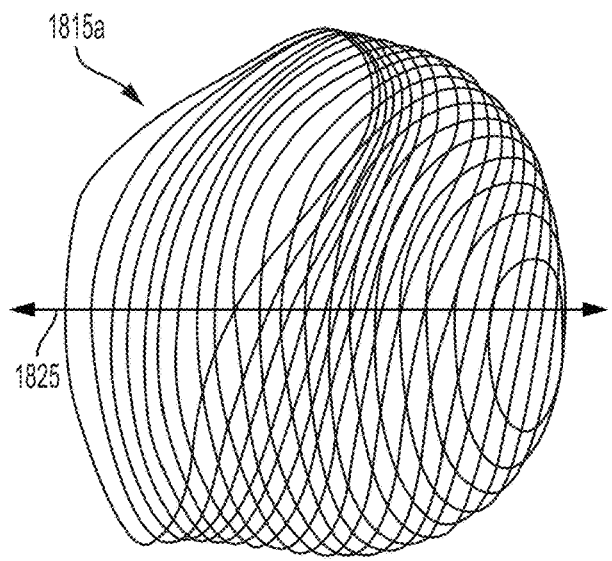
FIGS. 18A and 18B illustrate coil configurations for a head coil having principle axes substantially orthogonal to one another, in accordance with some embodiments.
Figure 18B:
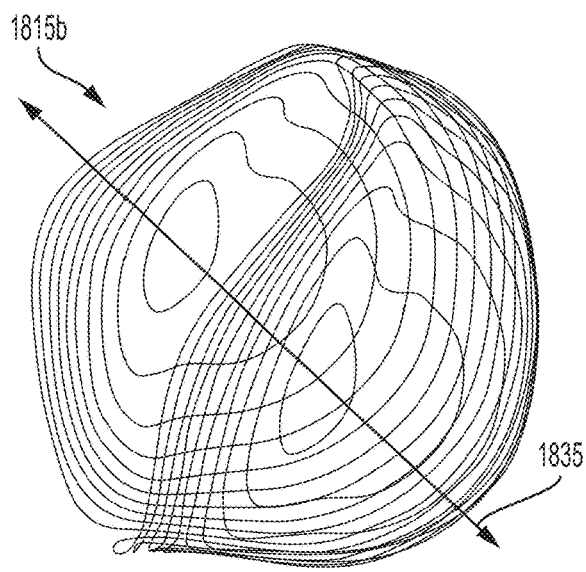
Figure 18C:
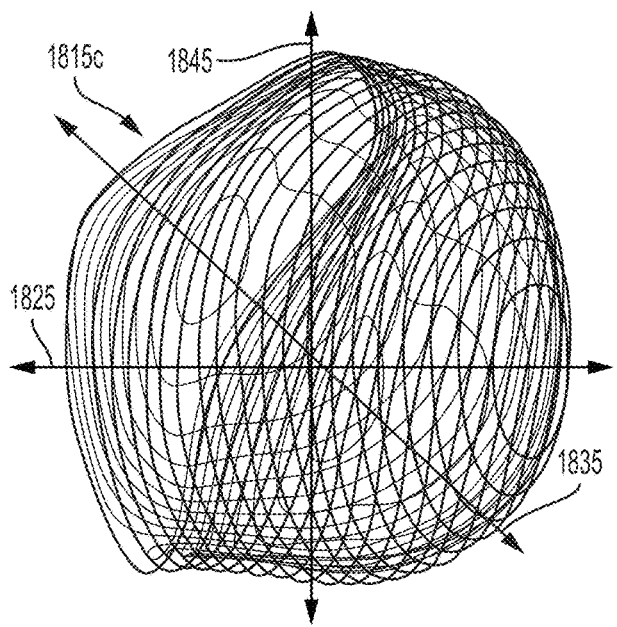
FIG. 18C illustrates the combined coil configurations illustrated in FIGS. 18A and 18B, in accordance with some embodiments.

By way of example, FIGS. 18A and 18B illustrate coil configurations that can be combined to provide a head coil capable of detecting MR signal components oriented along multiple axes, in accordance with some embodiments. In particular, FIG. 18A illustrates an exemplary coil configuration 1815a arranged to detect MR signal components oriented substantially along principal axis 1825 and FIG. 18B illustrates an exemplary coil configuration 1815b arranged to detect MR signal components oriented substantially along principal axis 1835 orthogonal to principal axis 1825. FIG. 18C illustrates a multiple coil configuration 1815c, produced by combining coil configurations 1815a and 1815b, arranged to detect MR signal components oriented substantially along principal axes 1825 and 1835.

Figure 19A:
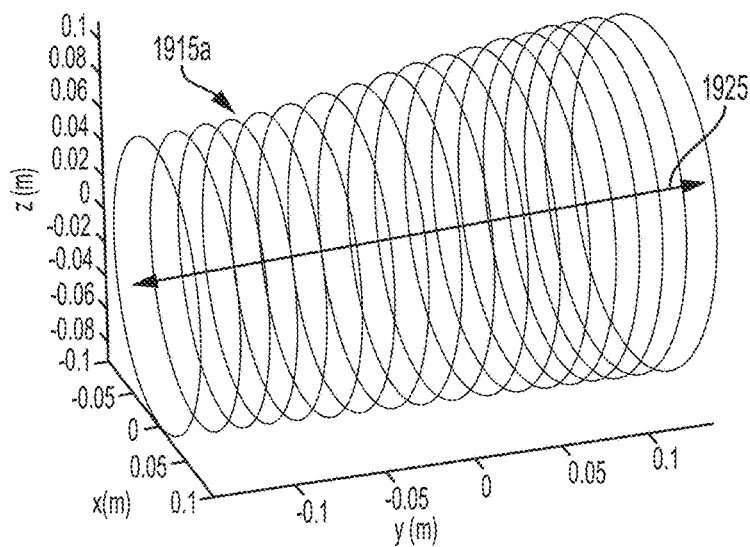
FIGS. 19A and 19B illustrate coil configurations for a leg coil having principle axes substantially orthogonal to one another, in accordance with some embodiments.
Figure 19B:
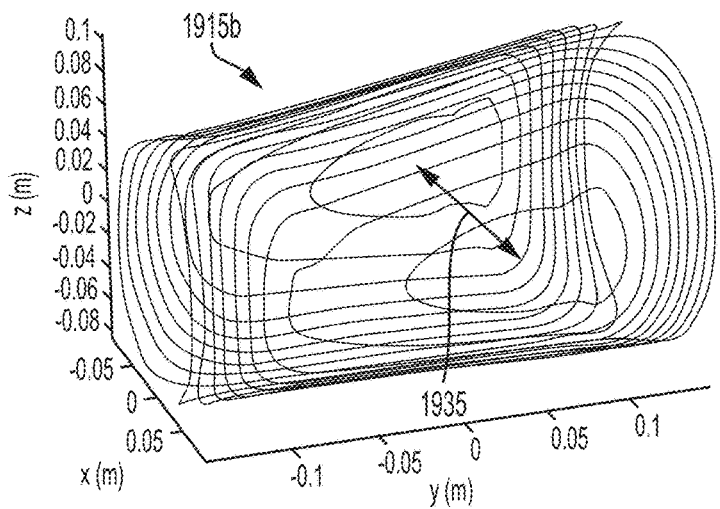
Figure 19C:
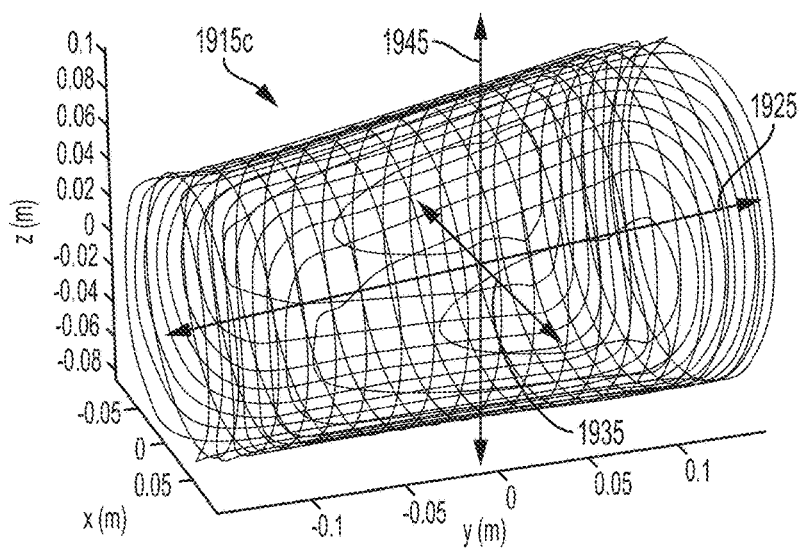
FIG. 19C illustrates the combined coil configurations illustrated in FIGS. 19A and 19B, in accordance with some embodiments.

As a further example, FIGS. 19A and 19B illustrate exemplary coil configurations 1915a and 1915b configured to detect MR signal components oriented along orthogonal principal axes 1925 and 1935, respectively, which may be combined to form coil configuration 1915c illustrated in FIG. 19C to provide a multiple coil configuration arranged to detect MR signal components oriented along multiple orthogonal axes. By configuring multiple coils to detect MR signal components oriented along substantially orthogonal axes, inductive coupling between the coils can be optimally avoided. Using dual coils configured with mutually orthogonal principal axes may, according to some embodiments, boost the SNR of MR signal detection by the square root of two. In particular, each of the dual coils may obtain an independent measurement of the same MR signal shifted in phase by 90°, resulting in a square root of two SNR improvement.

Figure 20:
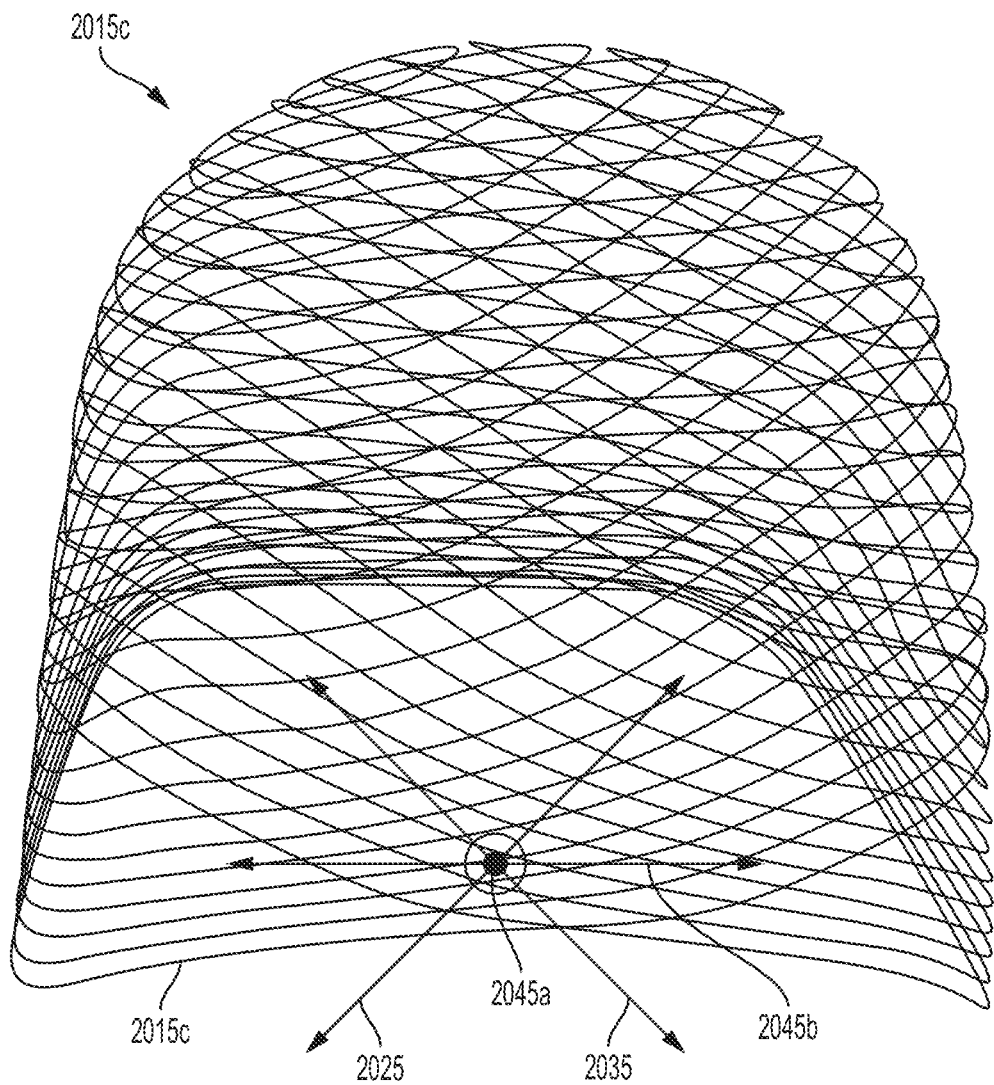
FIG. 20 illustrates combined coil configurations for a head coil having principal axes substantially parallel to one another, in accordance with some embodiments.

In the example coil configurations illustrated in FIGS. 18C and 19C, the dual coil configurations are oriented substantially orthogonal to one another and orthogonal to a B0 field. That is, the principal axes of the dual coils are orthogonal to one another and orthogonal to axis 1845, 1945 along which the B0 field is aligned. However, the inventors have recognized that other arrangements may also be used. For example, FIG. 20 illustrates a combined coil configuration 2015c for an exemplary head coil comprising coil configuration 2015a having conductor(s) arranged to detect MR signal components generally oriented along axis 2025 and coil configuration 2015b having conductor(s) arranged to detect MR signal components generally oriented along axis 2035. In the example configuration illustrated in FIG. 20, axes 2025 and 2035 are orthogonal to one another and at 45° relative to axis 2045a and 2045b, in which directions possible B0 fields may be generated, for example, by a low-field MRI device. It should be appreciated that other configurations are also possible, as the aspects are not limited in this respect. For example, a plurality of coils may be configured to detect MR signals in directions that are not orthogonal. However, in such cases, care should be taken to produce coils configurations having suitably low mutual inductance. The inventors have recognized that the optimization techniques described herein may be used to determine coil configurations in which the mutual inductance between the coils is minimized, as discussed in further detail below. In this way, a plurality of coils may be utilized that do not have orthogonal relationships with one another.

To apply a plurality of coil configurations (e.g., the exemplary coil configurations 1815c, 1915c, 2015c, etc.) to provide an RF transmit/receive component comprising multiple coils (e.g., a pair of quadrature coils), the inventors have appreciated that the conductor(s) forming the coil for respective configurations may be offset from one another. To separate a pair of coils arranged about a region of interest, the conductors of the coils may be offset from one another relative to the region of interest. For example, the conductor of a first coil may be arranged about the region of interest and the conductor of a second coil may be arranged about the region of interest at a distance further away from the region of interest. According to some embodiments, a support structure comprises an inner substrate layer having a surface about a region of interest to which a first coil is applied and an outer substrate layer having a surface about the region of interest to which a second coil is applied. The inner substrate layer and the outer substrate layer may be, for example, offset from one another in directions normal to the substrate surfaces to which the coils are applied. In this respect, the outer substrate layer is provided over the inner substrate layer with respect to the region of interest. Some non-limiting examples of a dual coil radio frequency component having a first coil provided in a first substrate layer of a support structure and a second coil provided in a second substrate layer of the support structure offset from the first substrate layer are described in further detail below. It should be appreciated, however, that multiple coils may be applied in other manners, as the aspects are not limited in this respect.

Figure 21:
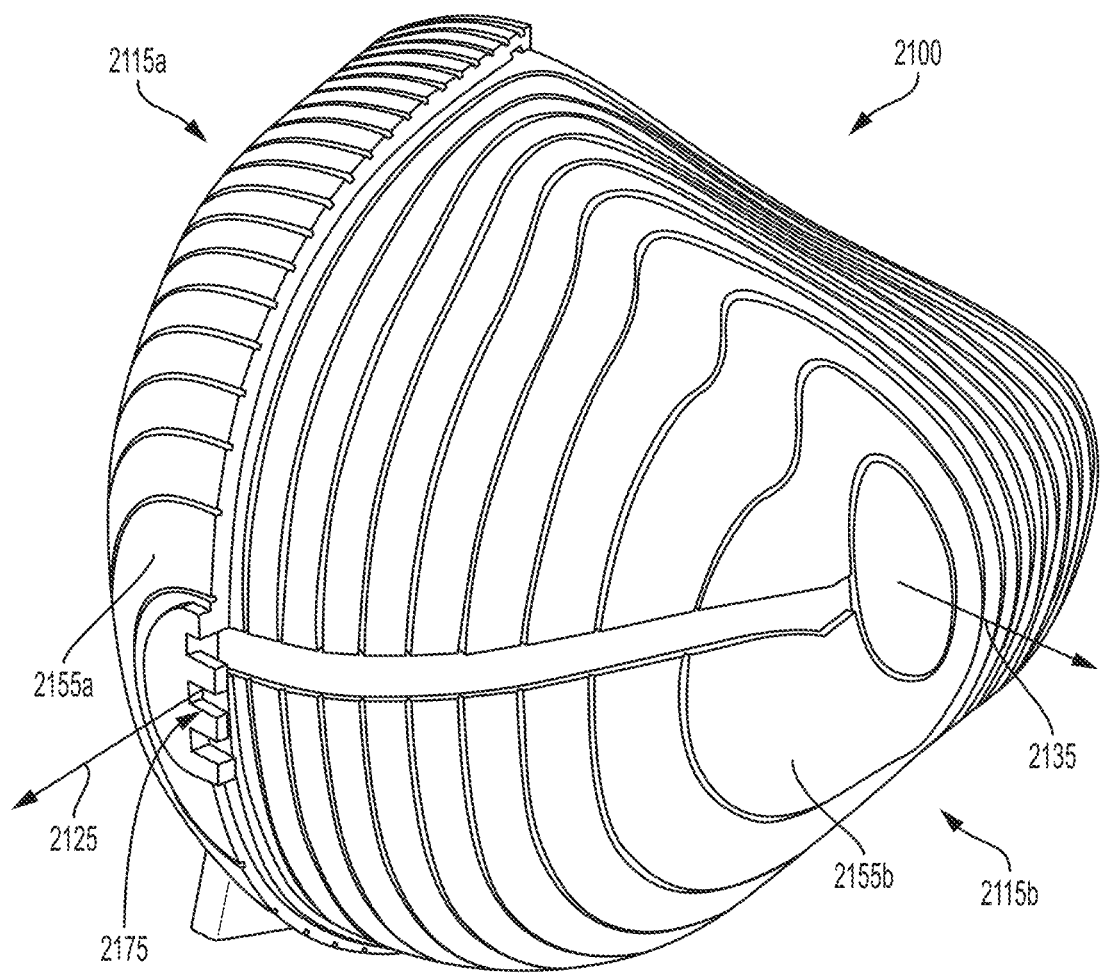
FIG. 21 illustrates exemplary coil configurations for a head coil applied to separate substrate layers of a support structure, in accordance with some embodiments.

By way of example of a dual coil radio frequency component, FIG. 21 illustrates a helmet 2100 to which a pair of coil configurations are applied to respective substrate layers of the helmet. In particular, coil configuration 2115a (e.g., a coil configuration similar to or the same as coil configuration 1815a illustrated in FIG. 18A) is applied to an outer substrate layer 2155a of the support structure of helmet 2100 via grooves adapted to accommodate the coil conductor arranged in accordance with the corresponding coil configuration. Substrate layer 2155a is illustrated in FIG. 21 with one of the hemispheres removed to illustrate the inner substrate layer underneath. In this respect, coil configuration 2115b (e.g., a coil configuration similar to or the same as coil configuration 1815b illustrated in FIG. 18B) is applied to an inner substrate layer 2155b of the support structure of helmet 2100 via grooves adapted to accommodate the coil conductor arranged in accordance with the corresponding coil configuration. As shown in FIG. 21, the direction of the offset of outer substrate layer 2155a from inner substrate layer 2155b is normal to the substrate surfaces and, in this illustrative example, outer substrate layer 2155a overlays inner substrate layer 2155b.

As shown by exemplary helmet 2100, the inner and outer substrate layers form respective surfaces about a region of interest within the helmet. When the helmet is worn by a patient and operated within an appropriate B0 field of an MRI system, the region of interest will include the field of view of the MRI system (i.e., the region of the B0 field having sufficient homogeneity to perform MRI). Thus, the exemplary substrate layers 2155a and 2155b illustrated in FIG. 21 are offset from one another relative to the region of interest, with outer substrate layer 2155a being arranged farther away from the region of interest than inner substrate layer 2155b. Consequently, when operated within a suitable B0 field of an MRI system, the coil applied to outer substrate layer 2155a will be farther away from the field of view than the coil applied to inner substrate layer 2155b. When a conductor is positioned within the grooves of substrate layer 2155a, the conductor forms a plurality of turns about principle axis 2125 (e.g., aligned with the longitudinal axis of the body), and when a conductor is positioned within the grooves of substrate layer 2155b, the conductor forms a plurality of turns about principle axis 2135 (e.g., substantially orthogonal to the longitudinal axis of the body).

When arranged in close proximity, coils provided in separate layers may exhibit capacitive coupling. This capacitive coupling between coils provided in separate layers may be reduced or avoided by increasing the distance between the coils in the different layers in the direction of the normal to the surface of the support structure. For example, by increasing the offset of the coil in the outer layer in the direction of the surface normal, capacitive coupling can be reduced or eliminated. However, increased offsets also generally decrease the sensitivity of the coil in the outer layer due to the increased distance from the region of interest, so the offset can be chosen to appropriately balance capacitive coupling and coil sensitivity as appropriate and/or desired. Alternately, or in addition to, decoupling networks may be included to reduce or eliminate the capacitive coupling between coils provided in separate layers.

In FIG. 21, openings or slots 2175 may be provided to facilitate connection of the hemispheres of outer layer 2155a and/or to accommodate the terminal ends of the coil conductor(s), once positioned within the grooves, to facilitate connection to the transmit and/or receive circuitry that operates the RF head coil. In this manner, multiple coil configurations may be applied to a support structure to produce an RF head coil having improved SNR.

Figure 22A:
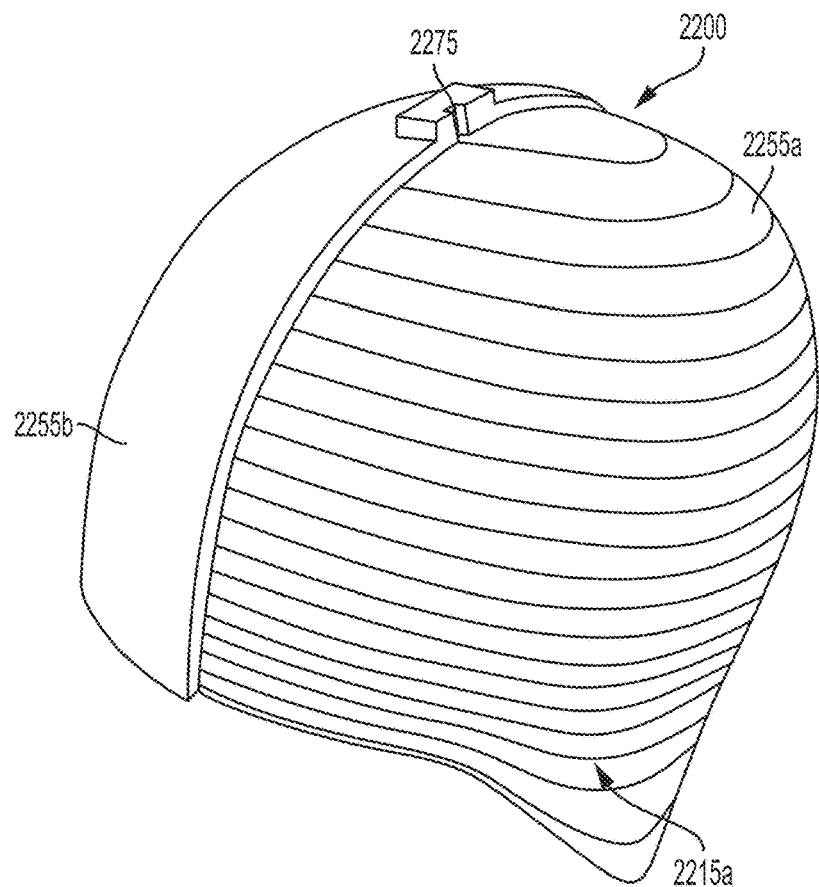
FIGS. 22A and 22B illustrate views of separate substrate layers of a support structure to which exemplary coil configurations for a head coil are applied, in accordance with some embodiments.
Figure 22B:
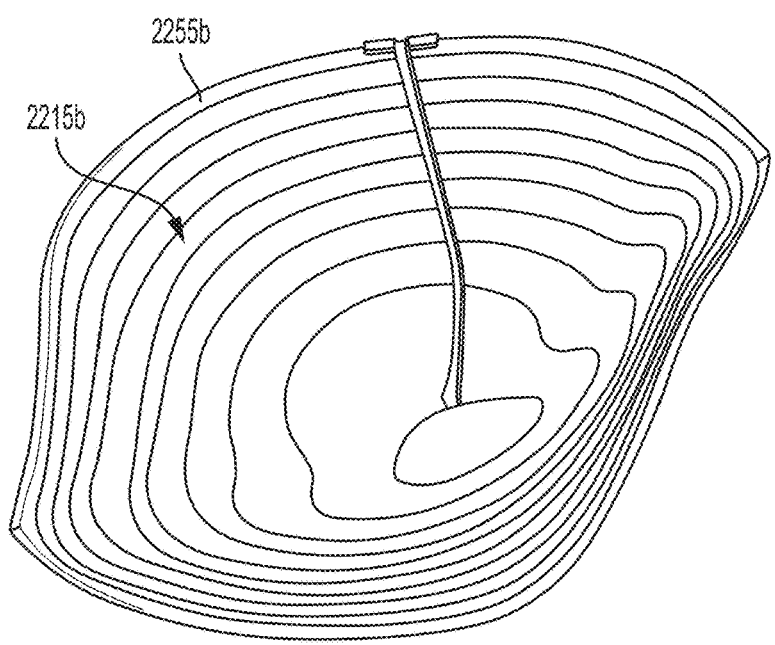

FIGS. 22A and 22B illustrate an alternative technique for applying multiple coil configurations to a support structure for a helmet 2200. In FIG. 22A, coil configuration 2215a (e.g., a coil configuration similar to or the same as coil configuration 1815a illustrated in FIG. 18A) is applied to an inner substrate layer 2255a of the support structure of helmet 2200 via grooves adapted to accommodate the coil and position the conductor in accordance with the corresponding coil configuration. FIG. 22B illustrates a hemisphere of an outer substrate layer 2255b removed to show inner substrate layer 2255a in FIG. 22A and to illustrate coil configuration 2215b applied to the inside surface of outer substrate layer 2255b. In particular, coil configuration 2215b (e.g., a coil configuration similar to or the same as coil configuration 1815b illustrated in FIG. 18B) is applied to the inside of outer layer 2255b (e.g., on the concave side of the outer layer) via grooves adapted to accommodate and position the coil conductor in accordance with the corresponding coil configuration. Opening 2275 is configured to accommodate the conductor terminals for connection to the transmit and/or receive circuitry and also may be adapted to attach the two portions of outer layer 2255b. It should be appreciated that either coil configuration may be applied to the inner or outer layers in FIGS. 21 and 22 and the choice of the arrangements shown are merely for illustration. In addition, it should be appreciated that coil configurations can be applied to either the concave or convex side of either the inner or outer substrate layers, and the arrangement illustrated is shown to illustrate that coil configurations can be applied to either side of a substrate surface.

Figure 23A:
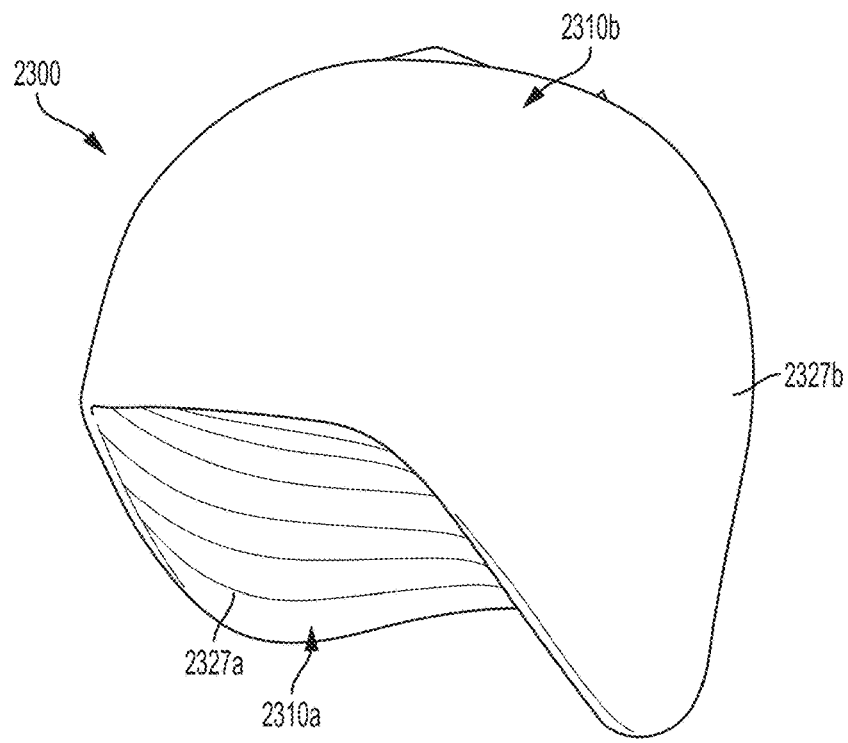
FIGS. 23A and 23B illustrate views of a head coil having conductors arranged according to respective coil configurations having principal axes substantially orthogonal to one another.
Figure 23B:
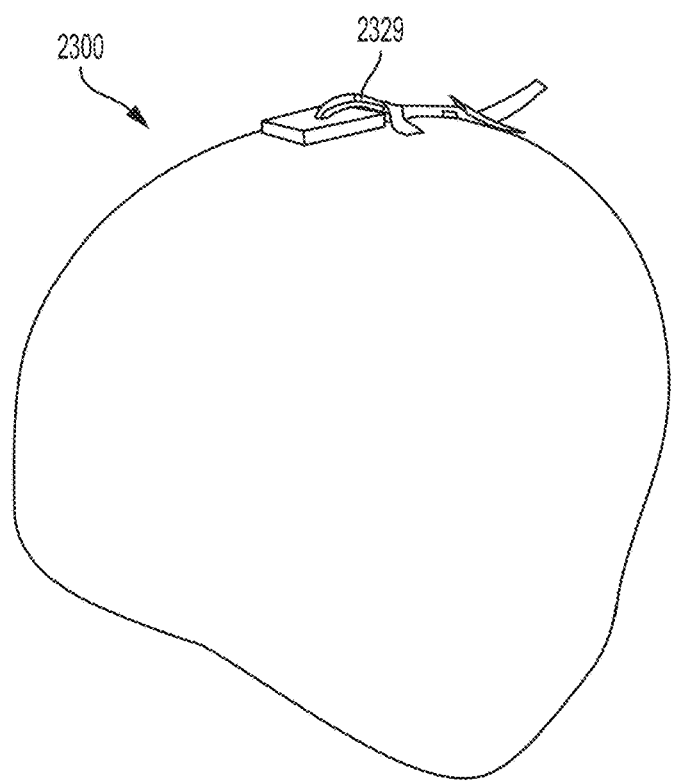

FIGS. 23A and 23B illustrate an RF head coil 2300 comprising a first RF coil 2310a formed by conductor 2327a arranged according to a first configuration (e.g., by positioning conductor 2327a within grooves patterned in an inner layer according to configuration 2215a illustrated in FIG. 22) and a second RF coil 2310b formed by conductor 2327b arranged according to a second configuration (e.g., by positioning conductor 2327b within grooves patterned in an outer layer according to configuration 2215b illustrated in FIG. 22), as shown in FIG. 23A. FIG. 23B shows the terminal end of conductors 2327a and 2327b emerging from the opening in the support structure of head coil 2300 for connection to the transmit and/or receive circuitry so that the RF head coil can be operated, for example, to obtain one or more MRI images (e.g., one or more images of a patient's brain). For example, RF head coil 2300 may be connected to a low-field MRI system to acquire MR signals with improved SNR, thus improving the quality of the acquired images.

It should be appreciated that providing conductors for an RF coil by providing grooves, channels or conduits according to a desired configuration is merely one example of producing an RF coil that may be suitable, for example, when producing supports structures using 3D printing or similar techniques. However, any method or technique may be used to provide a conductor according to a desired configuration to produce an RF coil. For example, one or more conductors may be encapsulated within support structure material in a molding process or other fabrication process, or one or more conductors may be affixed to a support structure in other ways such as by fasteners, adhesives, etc. Any suitable technique for providing conductors in accordance with a desired configuration may be used, as the aspects are not limited in this respect.

Figure 24:
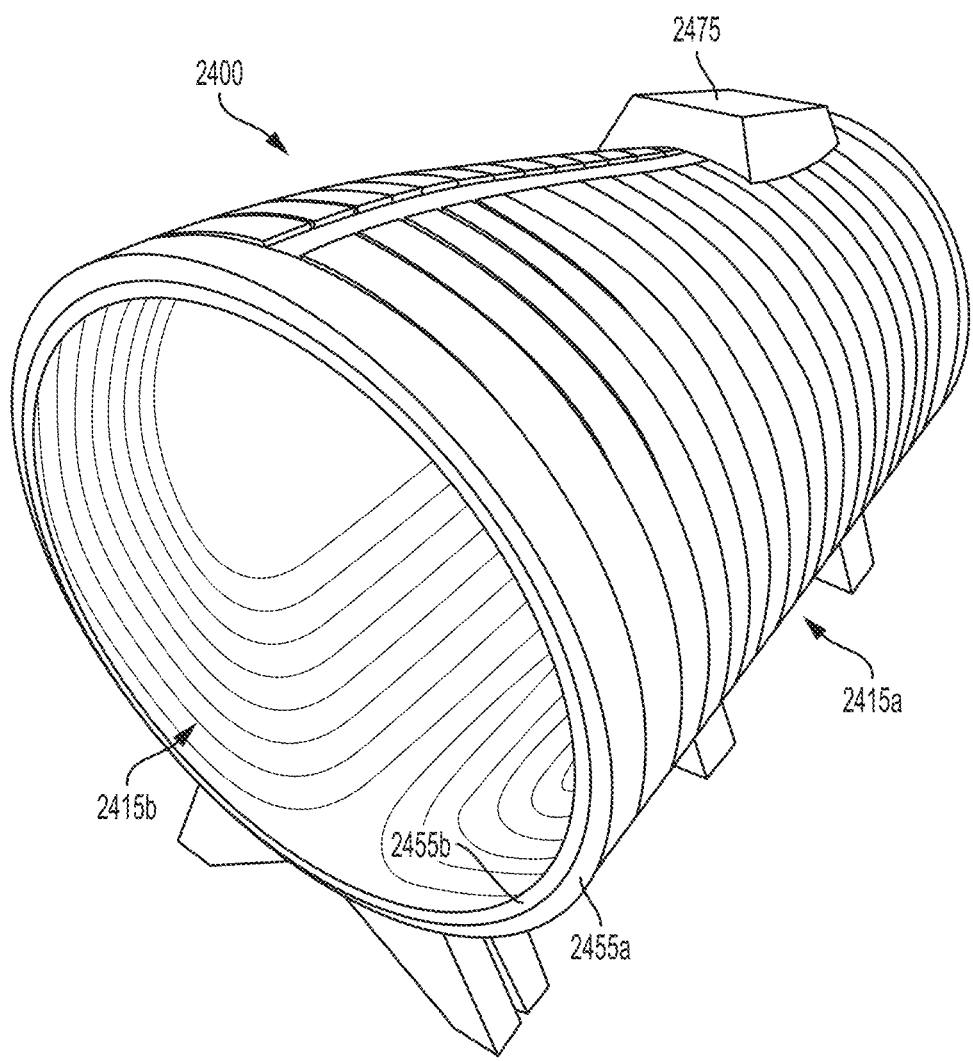
FIG. 24 illustrates exemplary coil configurations for a leg coil applied to separate substrate layers of a support structure, in accordance with some embodiments.

FIG. 24 illustrates a support structure 2400 for a leg coil to which a pair of coil configurations are applied. In particular, coil configuration 2415a (e.g., a coil configuration similar to or the same as coil configuration 1915a illustrated in FIG. 19A) is applied to an outer layer 2455a of the support structure 2400 via grooves adapted to accommodate and fix the coil conductor position in accordance with the corresponding coil configuration. Coil configuration 2415b (e.g., a coil configuration similar to or the same as coil configuration 1915b illustrated in FIG. 19B) is applied to an inner layer 2455b of the support structure 2400 via grooves adapted to accommodate and fix the coil conductor position in accordance with the corresponding coil configuration. Structure 2475 provides a mechanism to route the terminal ends of the conductors, once positioned within the grooves of the coil configurations, for connection to the transmit and/or receive circuitry to operate the RF coil. In this manner, multiple coil configurations may be applied to a support structure to produce an RF leg coil having improved SNR.

Figure 25:
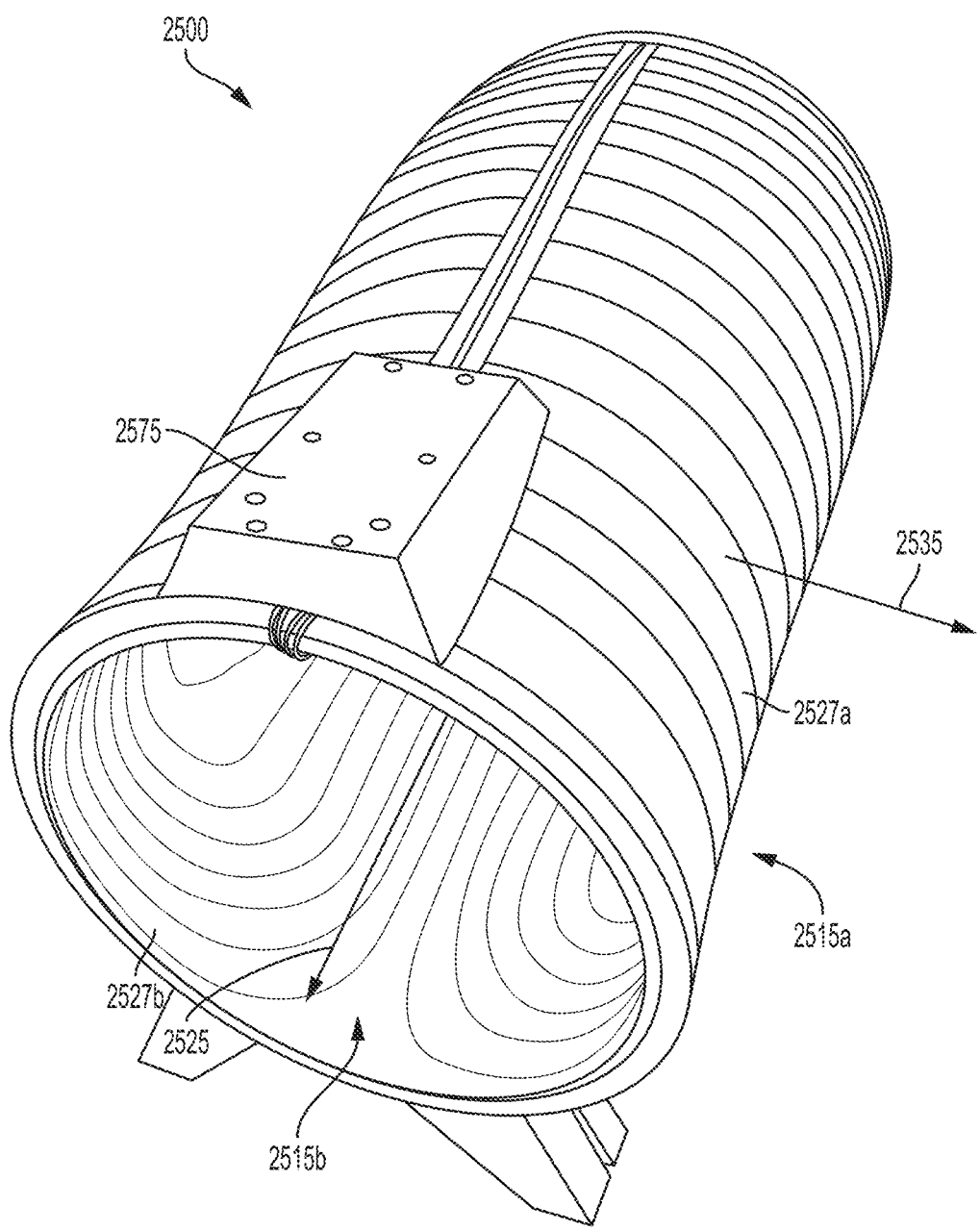
FIG. 25 illustrates a leg coil having conductors arranged according to respective coil configurations having principal axes substantially orthogonal to one another.

FIG. 25 illustrates an exemplary RF coil 2500 adapted for the leg comprising a first RF coil 2510a formed by conductor 2527a arranged according to a first configuration (e.g., by positioning conductor 2527a in an outer layer according to configuration 1915a illustrated in FIG. 19A) to form a plurality of turns about exemplary reference axis 2525 (e.g., the principal axis substantially aligned with the longitudinal axis of a leg positioned within the coil), and a second RF coil 2510b formed by conductor 2527b arranged according to a second configuration (e.g., by positioning conductor 2527b in an inner layer according to configuration 1915b illustrated in FIG. 19B) to form a plurality of turns about exemplary reference axis 2535 (e.g., the principal axis substantially orthogonal to the longitudinal axis of a leg positioned within the coil). RF coil 2500 may be used to obtain one or more images of a portion of the leg, for example, one or more images of the knee as part of a low-field MRI system. Connector 2575 routes the terminal ends of conductors 2527a and 2527b and provides connections to electrically connect the conductors to the transmit and/or receive circuitry of, for example, a low-field MRI system. It should be appreciated that the above described techniques may be used to produce RF coils for any portion of the anatomy and the exemplary head and leg coils depicted are merely examples to illustrate methods and apparatus developed by the inventors and discussed herein.

In embodiments having a radio frequency component comprising multiple coils, one or both of the coils may be used to transmit RF pulses to a region of interest to cause an MR response. For example, in some embodiments, only one of a plurality of coils is used as a transmit coil and each of the plurality of coils is used as a receive coil. According to some embodiments, each of the plurality of coils is used as a transmit coil and as a receive coil. As such, a plurality of coils may be used in any arrangement to provide a transmit/receive component of a magnetic resonance imaging system, for example, a low-field MRI system.

In embodiments that include a plurality of coils (e.g., RF transmit/receive components that utilize a pair of coils in a quadrature relationship, as illustrated by exemplary RF coils 2300 and 2500 illustrated in FIGS. 23 and 25), MR signals will produce electrical signals in each of the plurality of coils. These signals may be combined to improve SNR in any number of ways. For example, the electrical signals may be combined in the analog or digital domain. In the analog domain, electrical signals produced in each of the plurality of coils may be phase shifted appropriately and combined. For example, using the exemplary coils described above, the electrical signals produced in each of the pair of coils from corresponding MR signals will be 90° out of phase as a result of the orthogonality of the respective configurations. As such, electrical signals of one of the coils may be phase shifted by 90° and combined with electrical signals produced by the other coil to obtain a combined signal having increased SNR. In the digital domain, MR signals may be obtained over separate channels (e.g., separate signals may be obtained from each of the coils) and digitized. The digitized signals may then be processed digitally and combined in the digital domain by phase shifting the digitized signals. One advantage to obtaining separate signals and processing them in the digital domain is the ability to perform noise correction on the individual signals before combining them. However, MR signal components detected by multiple coils may be combined and processed in any suitable way, as the aspects are not limited in this respect.

As discussed above, the coil configurations of a radio frequency component comprising multiple coils may be optimized using the techniques described in the foregoing, for example, using magnetic synthesis to determine a coil configuration that is generally optimal with respect to one or more parameters. According to some embodiments, mutual inductance between multiple coils may be included as a term in an optimization scheme to minimize the mutual inductance between the coils. A mutual inductance term may be particularly beneficial in embodiments where the coil configuration are not oriented orthogonal to one another (e.g., coil configuration having principal axes that are not orthogonal to one another), either by design or because orthogonality cannot be achieved to the extent desired. Minimizing (or eliminating) mutual inductance between coils facilitates radio frequency components with improved SNR and/or sensitivity, thus improving the quality of MR signal detection.

A low-field MRI system may include a radio frequency component provided in accordance with any one or combination of the techniques described in the foregoing to facilitate acquiring clinically useful images at low-fields. For example, a low-field MRI system may include a B0 magnet 122 configured to produce a low-field B0 magnetic field and a transmit/receive component 125 may be optimized to increase the sensitivity and/or configured to improve the SNR of MR signal detection using any one or combination of techniques described herein to facilitate acquiring clinically useful images of desired portion(s) of the anatomy.

The inventors have further appreciated that a coil may be operated so that the coil produces more than one type of magnetic field in an MRI system. For example, the inventors have developed systems that drive one or more coils in a multifunction capacity to generate one or more gradient magnetic fields and to generate and/or receive one or more RF magnetic fields. According to some embodiments, a multifunction coil is configured to operate as at least one transmit/receive coil and as at least one gradient coil. The inventors have further recognized that the optimization techniques described herein may be employed to optimize a configuration of such a multifunction coil. Further details on the design and optimization of multifunction coils are provide below.

Figure 26A:
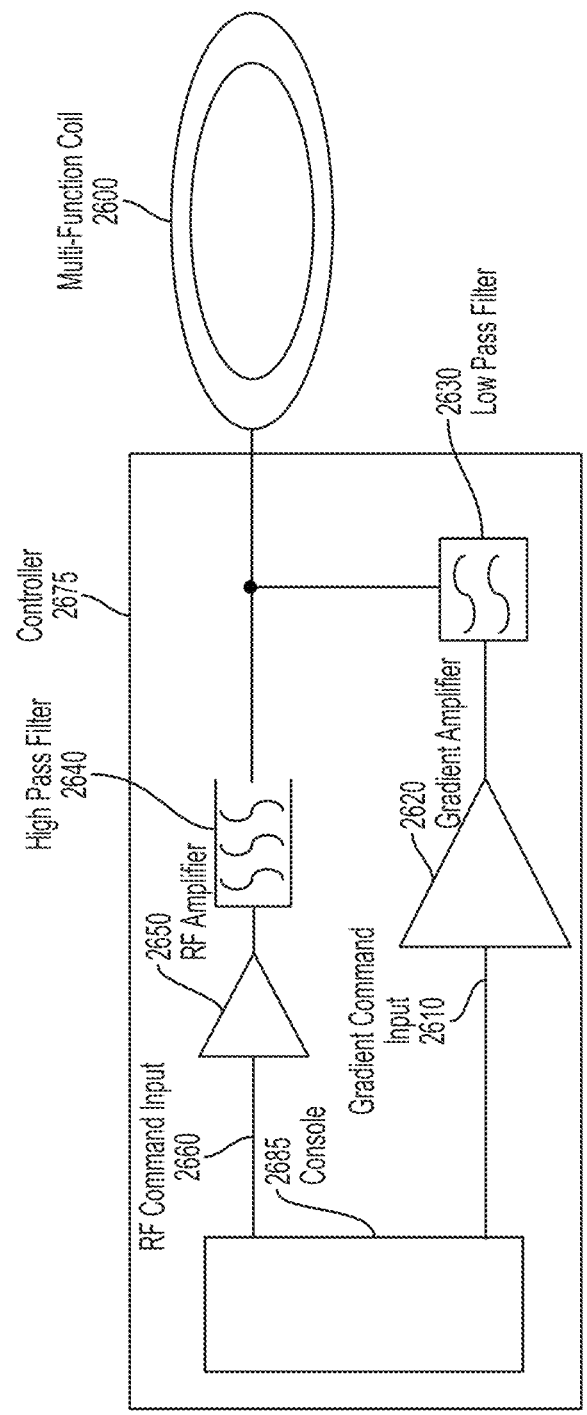
FIGS. 26A and 26B illustrate a controller configured to operate a multifunction coil, in accordance with some embodiments.

FIG. 26A illustrates a system configured for producing a multifunction coil operated to generate multiple types of magnetic fields, in accordance with some embodiments. The exemplary system schematically depicted in FIG. 26A comprises a controller 2675 coupled to a coil 2600 to cause the coil to generate at least a gradient magnetic field and an RF magnetic field. According to some embodiments, controller 2675 comprises gradient amplifier 2620 coupled to coil 2600 via low pass filter 2630. In operation, a console 2685 may issue gradient command input 2610 to cause gradient amplifier 2620 to drive coil 2600 to produce one or more gradient fields in accordance with a desired pulse sequence (e.g., a pulse sequence designed to acquire MR data for use in producing one or more images). In this manner, coil 2600 can be operated as a gradient coil (e.g., Gx, Gy, etc.), for example, in a low-field MRI system.

Figure 26B:
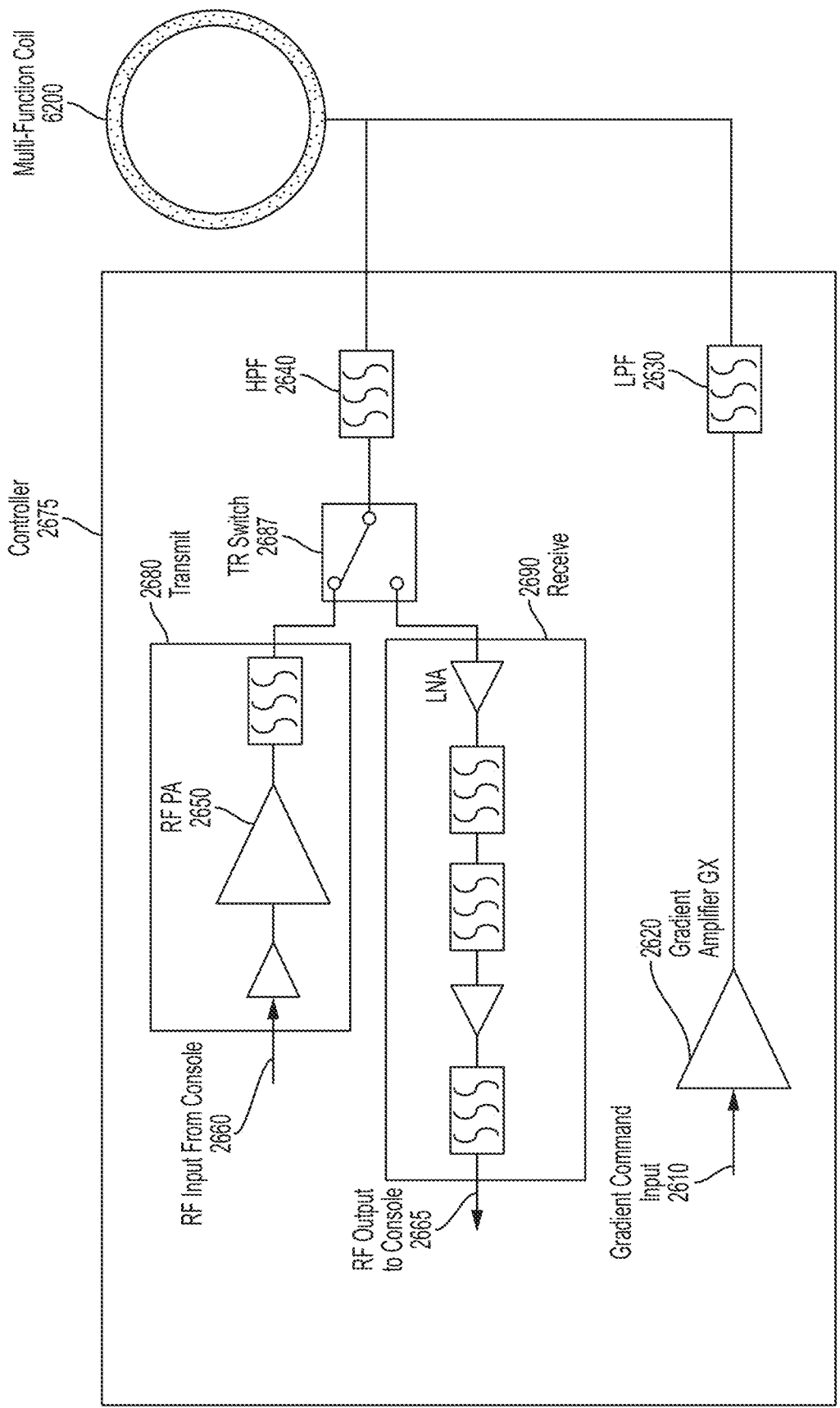

Controller 2675 further comprises RF amplifier 2650 coupled to coil 2600 via high pass filter 2640. Console 2685 may also issue RF command input 2660 to cause RF amplifier 2650 to drive coil 2600 to produce RF magnetic fields in accordance with the desired pulse sequence. By doing so, coil 2600 can also be operated as an RF coil. Controller 2675 may, according to some embodiments, also utilize coil 2600 to detect MR signals emitted in response to the RF magnetic fields generated by coil 2600 so that coil 2600 can be operated as a RF transmit coil and an RF receive coil. For example, FIG. 26B illustrates a multifunction coil 2600 driven by controller 2675 with both a transmit path 2680 and receive path 2690 to enable use of multifunction coil 2600 as both a transmit and receive coil. T/R switch 2687 switches between transmit path 2680 and receive path 2690 to allow multifunction coil to be selectively operated to produce RF magnetic fields and to detect MR signals emitted in response to an RF transmit cycle.

It should be appreciated that coil 2600 may be used as an RF receive coil with or without also operating coil 2600 as an RF transmit coil and vice versa. Thus, controller 2675 is configured to operate coil 2600 as both a gradient coil and an RF coil so that coil 2600 can provide multiple functions in an MRI system, such as a low-field MRI system. It should be appreciated that the controller illustrated in FIGS. 26A and B is merely exemplary and may include further components and/or may exclude one or more of the components illustrated, as a suitable controller for implementing a multifunction coil may include any combination of components configured to cause a coil to generate multiple types of magnetic fields.

According to some embodiments, a multifunction coil (e.g., coil 2600) is operated as a Gx gradient coil and as an RF transmit/receive coil. According to some embodiments, a multifunction coil is operated as a Gy gradient coil and as an RF transmit/receive coil. It should be appreciated that more than one multifunction coil may be utilized in an MRI system. For example, according to some embodiments, a first multifunction coil is configured to operate as a Gx gradient coil and a second multifunction coil is configured to operate as a Gy gradient coil, with both first and second multifunction coils also operating as RF transmit/receive coils. Multiple multifunction coils operated in this manner can be used to implement multiple transmit/receive channels that can be used to improve SNR, reduce acquisition times, or both. For example, MR data obtained from multiple receive coils may be combined to increase SNR. When both Gx and Gy gradient coils are also used as receive coils, a 90 degree phase difference will exist between the respective receive channels (i.e., because the Gx and Gy gradient coils are substantially orthogonal to one another as well as substantially orthogonal to the B0 magnetic field). This quadrature relationship can be exploited to boost SNR by as much as the square root of two. Alternatively, or in addition to increasing SNR, multiple transmit/receive coils may be used to perform parallel MR to reduce the acquisition time needed to obtain MR data for generating one or more images.

Figure 27:
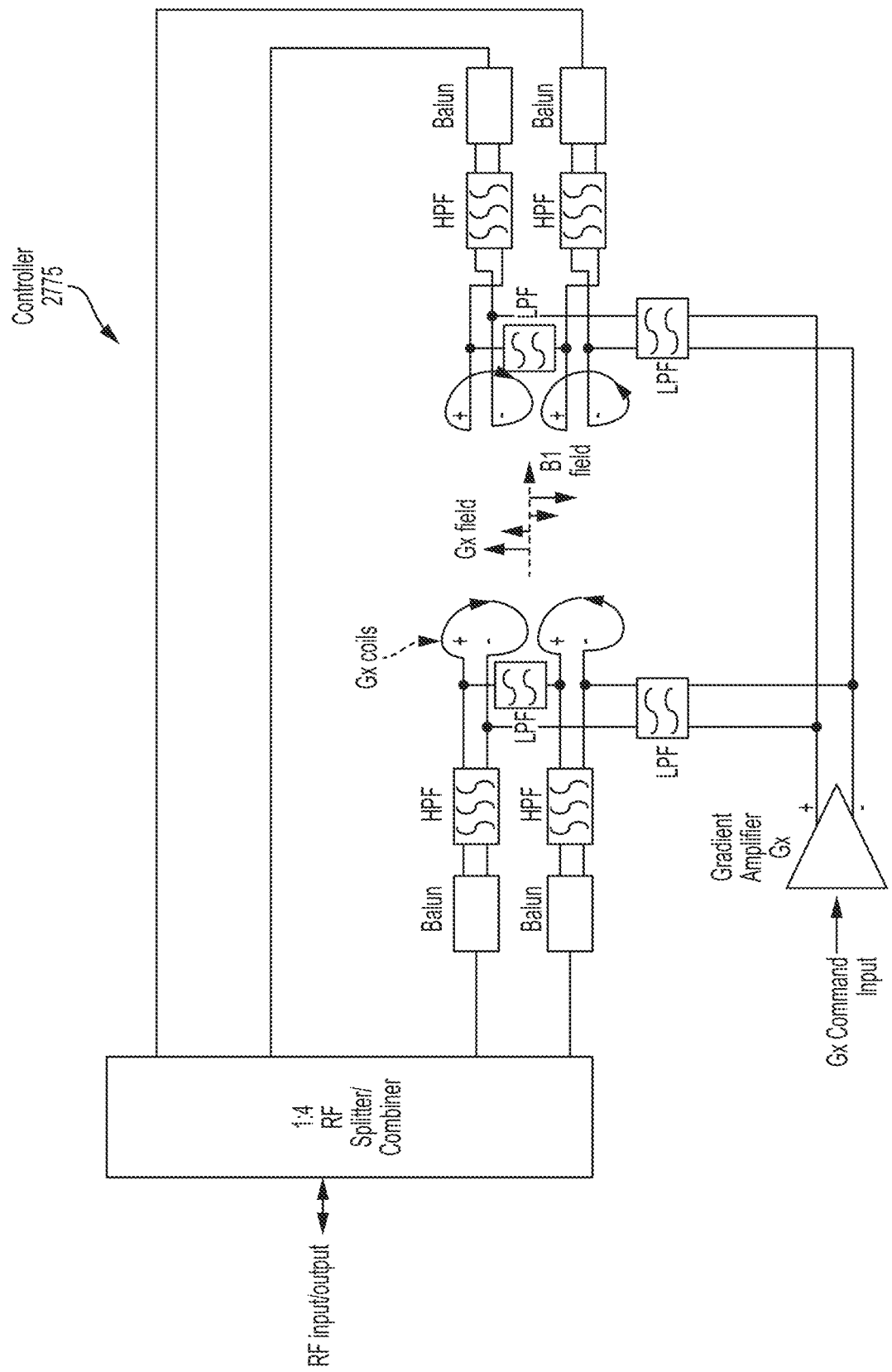
FIG. 27 illustrates a controller configured to operate a multifunction coil using a particular geometry for a gradient coil, in accordance with some embodiments.

FIG. 27 illustrates a system for providing a multifunction coil in connection with a specific configuration for a gradient coil set. It should be appreciated that while the gradient coil set illustrated in FIG. 27 is labeled as a Gx gradient coil set, this is not a limitation as the same techniques can equally be applied to a Gy gradient coil set. In FIG. 27, the gradient coil set is configured as coil pairs, with each pair having coils connected with opposite polarity, or using 180 degree in-line phase shifter circuits, such that they are driven 180 degrees out of phase. In FIG. 27, exemplary controller 2775 is configured to utilize the gradient coil set to also operate as an RF coil to transmit and/or receive RF magnetic fields. According to some embodiments, the gradient coil set is operated as a single RF coil. One technique to achieve this is to treat the gradient coil set as a single continuous coil by coupling, in addition to each high pass filter, a respective balun to a 1:4 RF splitter/combiner. In this way, a gradient coil set of the configuration illustrated in FIG. 27 can also be driven as a transmit and/or receive coil. Alternatively, each coil in the gradient coil set can be treated separately from the RF perspective by driving each coil with a respective RF amplifier and high pass filter so that the gradient coil set can be operated as four separate transmit and/or receive coils.

The inventors have appreciated that multifunction coil techniques may facilitate reduced cost and/or reduced size low-field MRI systems. For example, techniques described herein can be applied to the low-field MRI systems for imaging the head illustrated in FIGS. 22A-C of the '652 Application. These systems include a head component (e.g., a helmet) configured to accommodate the head of the person being imaged. The head component may have incorporated therein one or more coils of the low-field MRI system (e.g., a B0 magnet, one or more gradient coils, one or more transmit/receive coils, etc.). The inventors have recognized that the illustrated head imaging systems can be produced with at least one coil incorporated or housed in the head component that is configured to produce at least two types of magnetic fields (i.e., the head component can house one or more multifunction coils). According to some embodiments, the head component comprises a coil configured to transmit and/or receive RF magnetic fields and to generate at least one gradient magnetic field. As discussed in the foregoing, such a multifunction coil may be achieved by coupling a controller to the multifunction coil to operate the coil as both an RF coil and a gradient coil (e.g., by coupling a first amplifier and high pass filter to the coil to drive the coil to generate and/or receive RF magnetic fields and coupling a second amplifier and a low pass filter to the coil to drive the coil to generate at least one gradient magnetic field). In this manner, one or more multifunction coils may be utilized to generate both transmit RF pulses and gradient pulses in accordance with a desired pulse sequence, and detect MR signals emitted in response.

By utilizing the above described techniques to implement a multifunction coil, the cost of the resulting system may be reduced as a single coil can be used to produce more than one type of magnetic field for the MRI system. Additionally, a multifunction coil can reduce the footprint of the system and/or facilitate designs where the space available for incorporating the system's magnetics is limited (e.g., in the head imaging systems discussed above). Another benefit of some embodiments described above relates to the ability to implement multiple transmit and/or receive channels using the gradient coils of the MRI system.

The inventors have appreciated that the optimization techniques described herein may be applied to generally optimize the configuration of a multifunction coil. As discussed above, an optimization can be formulated that determines a coil configuration that meets one or more constraints and that, when simulated, produces a magnetic field that satisfies one or more criteria. By formulating an optimization to include regularization terms for both gradient and RF coils, a coil configuration can be determined that can produce both gradient and RF magnetic fields that meet specified criteria. Thus, the optimization techniques described herein can be applied to produce single function and multifunction coils alike.

U.S. patent application Ser. No. 14/845,949 ('949 Application), filed Sep. 4, 2015 and entitled "Noise Suppression Methods and Apparatus" describes, among other subject matter, techniques for using auxiliary sensors to facilitate characterization of the noise environment of a low-field MRI system to suppress noise received by one or more RF receive coils, which application is herein incorporated by reference in its entirety. The techniques described in the '949 Application allow a magnetic resonance imaging system (e.g., a low-field MRI system) to be operated outside a shielded room, facilitating production of MRI systems that can be operated in arbitrary environments so that MRI can be used in numerous situations where conventional MRI cannot. Any of the noise cancellation techniques described in the '949 Application can be used in connection with coil configurations described herein. Moreover, the inventors have appreciated that the optimization techniques described herein can also be applied to determine an optimal configuration of one or more auxiliary sensors (e.g., an auxiliary coil) for use in noise suppression. In particular, one or more criteria and/or one or more constraints corresponding to desired operation of an auxiliary coil may be incorporated into the optimization scheme described in the foregoing to determine a coil configuration for the auxiliary coil. As further discussed in the '949 Application, some embodiments include using a RF coil both as an auxiliary coil and as a primary coil and, in this respect, represents another example of a multifunction coil. The optimization techniques described herein may also be used to determine a configuration for a multifunction coil configured to operate both as a primary and auxiliary coil or additionally as a gradient coil as well.

As discussed above, optimization techniques described herein may be used to optimize a configuration for a head coil disposed on a surface of a helmet adapted to accommodate a patient's head. The inventors have appreciated that one or more auxiliary coils may be positioned on or proximate the helmet to facilitate noise suppression. For example, the head coil may be configured to optimally detect MR signals emitted from the patient within a field of view located within the helmet. One or more auxiliary coils may be positioned proximate (or on) the helmet so that it responds to the noise environment but does not respond to MR signals emitted from the field of view. The noise signal from the one or more auxiliary coils may be used to suppress noise in the MR signals detected by the head coil, for example, using any of the techniques described in the '949 Application.

As discussed above, and in detail in the '949 Application, one or more auxiliary coils may be used to detect the noise environment but not MR signals emitted from the field of view of an MRI system. This is typically achieved by positioning one or more auxiliary coils proximate a primary coil (e.g., the main receive coil of the MRI system) so that the auxiliary coil is responding to as similar a noise environment as the primary coil as possible, yet is located outside the detection range of emitted MR signals so that the auxiliary coil does not respond to emitted MR signals. In this manner, the one or more auxiliary coils characterizes substantially the same noise environment as the primary coil, but does not respond to MR signals so that the noise environment, as characterized by the one or more auxiliary coils, can be used to suppress noise detected by the primary coil. However, when positioned proximate one another in this manner, the primary coil and the auxiliary coil may inductively couple such that the one or more auxiliary coils has a response to MR signals emitted from the field of view even though it is outside the range of the MR signals because of the inductive coupling with the primary coil. Because the auxiliary coil response includes MR signal content as well, the described noise suppression techniques will operate to suppress the MR signal content detected by the primary coil, thereby reducing SNR instead of increasing SNR as intended.

The inventors have appreciated that the optimization techniques described herein may be utilized to generate a configuration for an auxiliary coil that reduces or eliminates inductive coupling with the primary coil. Using this technique, an auxiliary coil can be positioned proximate a primary coil while avoiding deleterious inductive coupling. According to some embodiments, a configuration of one or more auxiliary coils is optimized to reduce or eliminate inductive coupling with a primary coil. For example, the optimization scheme may incorporate one or more terms that define a region over which the auxiliary coil is sensitive to noise, which region excludes the region where MR signals can be detected directly, and one or more terms that operate to minimize inductive coupling between one or more auxiliary coils and a primary coil (e.g., one or more terms that cause the resulting configuration to, when operated in conjunction with the primary coil, suppress or cancel mutual inductance between coils). According to some embodiments, a configuration for a primary coil and one or more auxiliary coils can be optimized together so that the resulting primary coil has generally optimal performance with respect to specified criteria for receive coil operation and the resulting one or more auxiliary coils operates with minimal or no inductive coupling with the primary coil.

It should be appreciated that the techniques described herein can be applied to determine a coil configuration optimized for any portion of the human anatomy and the illustrated head coils are merely exemplary. In particular, the optimization techniques described herein are agnostic with respect to the particular surface on which a coil configuration is optimized. As such, the techniques described herein can be applied to any surface that can be modeled. For example, using a triangular mesh to model the surface, virtually any surface can be triangulated and, as such, there are no meaningful limitations on the geometry of an RF coil to which these techniques can be applied. Accordingly, a configuration for RF coils for any portion of the anatomy can be determined using techniques described herein, including, but not limited to head coils, coils for the torso, arms, legs, hands, feet, etc., or any combination thereof. In addition, the optimization techniques can be applied to any combination of multifunction coils for any desired part of the anatomy.

Having thus described several aspects and embodiments of the technology set forth in the disclosure, it is to be appreciated that various alterations, modifications, and improvements will readily occur to those skilled in the art. Such alterations, modifications, and improvements are intended to be within the spirit and scope of the technology described herein. For example, those of ordinary skill in the art will readily envision a variety of other means and/or structures for performing the function and/or obtaining the results and/or one or more of the advantages described herein, and each of such variations and/or modifications is deemed to be within the scope of the embodiments described herein. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

The above-described embodiments can be implemented in any of numerous ways. One or more aspects and embodiments of the present disclosure involving the performance of processes or methods may utilize program instructions executable by a device (e.g., a computer, a processor, or other device) to perform, or control performance of, the processes or methods. In this respect, various inventive concepts may be embodied as a computer readable storage medium (or multiple computer readable storage media) (e.g., a computer memory, one or more floppy discs, compact discs, optical discs, magnetic tapes, flash memories, circuit configurations in Field Programmable Gate Arrays or other semiconductor devices, or other tangible computer storage medium) encoded with one or more programs that, when executed on one or more computers or other processors, perform methods that implement one or more of the various embodiments described above. The computer readable medium or media can be transportable, such that the program or programs stored thereon can be loaded onto one or more different computers or other processors to implement various ones of the aspects described above. In some embodiments, computer readable media may be non-transitory media.

The terms "program" or "software" are used herein in a generic sense to refer to any type of computer code or set of computer-executable instructions that can be employed to program a computer or other processor to implement various aspects as described above. Additionally, it should be appreciated that according to one aspect, one or more computer programs that when executed perform methods of the present disclosure need not reside on a single computer or processor, but may be distributed in a modular fashion among a number of different computers or processors to implement various aspects of the present disclosure.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that convey relationship between the fields. However, any suitable mechanism may be used to establish a relationship between information in fields of a data structure, including through the use of pointers, tags or other mechanisms that establish relationship between data elements.

The above-described embodiments of the present invention can be implemented in any of numerous ways. For example, the embodiments may be implemented using hardware, software or a combination thereof. When implemented in software, the software code can be executed on any suitable processor or collection of processors, whether provided in a single computer or distributed among multiple computers. It should be appreciated that any component or collection of components that perform the functions described above can be generically considered as a controller that controls the above-discussed function. A controller can be implemented in numerous ways, such as with dedicated hardware, or with general purpose hardware (e.g., one or more processor) that is programmed using microcode or software to perform the functions recited above, and may be implemented in a combination of ways when the controller corresponds to multiple components of a system.

Further, it should be appreciated that a computer may be embodied in any of a number of forms, such as a rack-mounted computer, a desktop computer, a laptop computer, or a tablet computer, as non-limiting examples. Additionally, a computer may be embedded in a device not generally regarded as a computer but with suitable processing capabilities, including a Personal Digital Assistant (PDA), a smartphone or any other suitable portable or fixed electronic device.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible formats.

Such computers may be interconnected by one or more networks in any suitable form, including a local area network or a wide area network, such as an enterprise network, and intelligent network (IN) or the Internet. Such networks may be based on any suitable technology and may operate according to any suitable protocol and may include wireless networks, wired networks or fiber optic networks.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively.

What is claimed is:

1. A radio frequency component configured for magnetic resonance imaging (MRI), the radio frequency component comprising:
    a first coil configured to generate magnetic field components, the first coil including a first conductor arranged in a plurality of turns having non-uniform spacing; and
    a second coil configured to be responsive to magnetic resonance signal components,
    wherein the first and second coil are tuned to resonate at a frequency corresponding to a $B_0$ field having a field strength of less than or equal to 0.1 T.

2. The radio frequency component of claim 1, wherein the first and second coil are tuned to resonate at a frequency corresponding to a $B_0$ field having a field strength of less than or equal to 0.1 T and greater than or equal to 50 mT.

3. The radio frequency component of claim 2, wherein the plurality of turns includes 5 turns.

4. The radio frequency component of claim 1, wherein a configuration of the first coil is determined by performing at least one optimization that determines a value for at least one parameter of a model of the radio frequency component.

5. The radio frequency component of claim 4, wherein the non-uniform spacing is determined using the at least one optimization.

6. The radio frequency component of claim 4, wherein a number of turns in the plurality of turns is determined based, at least in part, on performing the at least one optimization using the model of the radio frequency component.

7. The radio frequency component of claim 1, wherein the first coil is tuned to resonate at a target frequency, and wherein a number of turns in the plurality of turns are limited so that a self-resonance of the first conductor is at a frequency at least twice the target frequency.

8. The radio frequency component of claim 1, wherein the first conductor is arranged in a three-dimensional geometry about a region of interest in accordance with a coil configuration of the first conductor in the three-dimensional geometry.

9. The radio frequency component of claim 8, wherein the magnetic field components, generated by the first coil, cause a magnetic resonance response from the region of interest.

10. The radio frequency component of claim 1, wherein each of the plurality of turns comprises a conductive path provided 360° or substantially 360° about a reference axis.

11. The radio frequency component of claim 1, wherein the first conductor has a length of at least 1 meter.

12. An apparatus, comprising:
- a radio frequency component configured for magnetic resonance imaging (MRI), the radio frequency component comprising;
  - a first coil configured to generate magnetic field components, the first coil including a first conductor arranged in a plurality of turns having non-uniform spacing;
  - a second coil configured to be responsive to magnetic resonance signal components; and
- a support structure configured to accommodate a portion of a body of a patient, the support structure having grooves configured to accommodate the first conductor and the second conductor.

13. The apparatus of claim 12, wherein the first coil is configured to generate magnetic field components to cause a magnetic resonance response from a region of interest.

14. The apparatus of claim 12, wherein a configuration of the first coil is determined by performing at least one optimization that determines a value for at least one parameter of a model of the radio frequency component.

15. The apparatus of claim 12, wherein the radio frequency component is a head coil, and wherein the support structure comprises a helmet formed to accommodate a human head.

* * * * *